(12) United States Patent
Mosler et al.

(10) Patent No.: US 8,821,436 B2
(45) Date of Patent: Sep. 2, 2014

(54) DUAL CONTAINER FLUID TRANSFER DEVICE

(75) Inventors: Theodore J. Mosler, Raleigh, NC (US);
Bryan J. Peters, Raleigh, NC (US);
David L. Foshee, Apex, NC (US);
Nathan R. Snell, Raleigh, NC (US)

(73) Assignee: Yukon Medical, LLC, Morrisville, NC (US)

( * ) Notice: Subject to any disclaimer, the term of this patent is extended or adjusted under 35 U.S.C. 154(b) by 215 days.

(21) Appl. No.: 12/896,393

(22) Filed: Oct. 1, 2010

(65) Prior Publication Data
US 2011/0087164 A1    Apr. 14, 2011

Related U.S. Application Data

(63) Continuation-in-part of application No. PCT/US2009/039215, filed on Apr. 1, 2009.

(60) Provisional application No. 61/201,964, filed on Dec. 17, 2008, provisional application No. 61/133,179, filed on Jun. 26, 2008, provisional application No. 61/072,543, filed on Apr. 1, 2008.

(51) Int. Cl.
*A61M 5/32* (2006.01)
*A61M 37/00* (2006.01)

(52) U.S. Cl.
USPC .............................. 604/82; 604/411

(58) Field of Classification Search
CPC ............... A61M 5/162; A61M 2005/1623; A61M 39/26; A61J 1/12; A61J 1/10; A61J 1/2096; A61J 1/1475; A61J 1/2089; A61J 1/20; A61J 1/2093; A61J 2001/2013; A61J 2001/1468; A61J 2001/2082; A61J 2001/2075; A61J 2001/2037
USPC ....................... 604/82–92, 411–416, 246–256
See application file for complete search history.

(56) References Cited

U.S. PATENT DOCUMENTS 2,584,397 A     2/1952  Pitman
4,175,559 A    11/1979  Kreb
(Continued)

FOREIGN PATENT DOCUMENTS

EP    0 570 939 B1    11/1993
EP    0 521 460 B1     9/1995
(Continued)

OTHER PUBLICATIONS

The International Bureau of WIPO, International Preliminary report on Patentability and Writing Opinion for International Application No. PCT/US2009/039215, dated Oct. 5, 2010.
(Continued)

*Primary Examiner* — Matthew F Desanto
(74) *Attorney, Agent, or Firm* — Christopher J. Knors; Moore & Van Allen PLLC

(57) ABSTRACT

A fluid transfer device is disclosed and described, the device comprising a housing comprising a first piercing assembly associated with the housing, the first piercing assembly adapted for accessing a first container, the first piercing assembly comprising a first piercing member comprising at least one conduit. A second piercing assembly is associated with the housing, the second piercing assembly adapted for accessing a second container, the second piercing assembly comprising a second piercing member comprising at least one conduit.

12 Claims, 51 Drawing Sheets

(56) References Cited

U.S. PATENT DOCUMENTS

| | | | |
|---|---|---|---|
| 4,423,741 A * | 1/1984 | Levy | 600/581 |
| 4,581,014 A * | 4/1986 | Millerd et al. | 604/80 |
| 4,729,401 A | 3/1988 | Raines | |
| 4,759,756 A | 7/1988 | Forman et al. | |
| 4,863,454 A | 9/1989 | LaBove | |
| 4,921,490 A | 5/1990 | Spier et al. | |
| 4,994,029 A | 2/1991 | Rohrbough | |
| 4,997,430 A | 3/1991 | Van Der Heiden et al. | |
| 5,088,996 A | 2/1992 | Kopfer et al. | |
| 5,152,965 A | 10/1992 | Fisk et al. | |
| 5,232,029 A | 8/1993 | Knox et al. | |
| 5,257,650 A | 11/1993 | Fisk et al. | |
| 5,279,576 A | 1/1994 | Loo et al. | |
| 5,297,433 A | 3/1994 | Elgas | |
| 5,304,163 A | 4/1994 | Bonnici et al. | |
| 5,304,165 A | 4/1994 | Haber et al. | |
| 5,329,976 A | 7/1994 | Haber et al. | |
| 5,334,163 A | 8/1994 | Sinnett | |
| 5,352,191 A | 10/1994 | Sunago et al. | |
| 5,423,753 A | 6/1995 | Fowles et al. | |
| 5,445,631 A | 8/1995 | Uchida | |
| 5,464,123 A | 11/1995 | Scarrow | |
| 5,466,220 A | 11/1995 | Brenneman | |
| 5,520,659 A | 5/1996 | Hedges | |
| 5,522,804 A | 6/1996 | Lynn | |
| 5,526,853 A | 6/1996 | McPhee et al. | |
| 5,527,306 A | 6/1996 | Haining | |
| 5,554,128 A | 9/1996 | Hedges | |
| 5,599,302 A | 2/1997 | Lilley et al. | |
| 5,636,660 A | 6/1997 | Pfleiderer et al. | |
| 5,641,010 A | 6/1997 | Maier | |
| 5,685,845 A | 11/1997 | Grimard | |
| 5,743,312 A | 4/1998 | Pfeifer et al. | |
| 5,766,147 A | 6/1998 | Sancoff et al. | |
| 5,776,124 A | 7/1998 | Wald | |
| 5,785,701 A | 7/1998 | Sams et al. | |
| 5,833,213 A | 11/1998 | Ryan | |
| 5,833,674 A | 11/1998 | Turnbull et al. | |
| 5,846,233 A | 12/1998 | Lilley et al. | |
| 5,873,872 A | 2/1999 | Thibault et al. | |
| 5,879,337 A | 3/1999 | Kuracina et al. | |
| 5,890,610 A | 4/1999 | Jansen et al. | |
| 5,989,237 A | 11/1999 | Fowles et al. | |
| 6,019,750 A | 2/2000 | Fowles et al. | |
| 6,021,824 A | 2/2000 | Larsen et al. | |
| 6,022,339 A | 2/2000 | Fowles et al. | |
| 6,063,068 A | 5/2000 | Fowles et al. | |
| D427,308 S | 6/2000 | Zinger | |
| 6,071,270 A | 6/2000 | Fowles et al. | |
| 6,090,092 A | 7/2000 | Fowles et al. | |
| 6,113,571 A | 9/2000 | Zinger et al. | |
| 6,113,583 A | 9/2000 | Fowles et al. | |
| 6,139,534 A | 10/2000 | Niedospial et al. | |
| 6,146,362 A | 11/2000 | Turnbull et al. | |
| 6,149,623 A | 11/2000 | Reynolds | |
| 6,159,192 A | 12/2000 | Fowles et al. | |
| 6,168,037 B1 | 1/2001 | Grimard | |
| 6,209,738 B1 | 4/2001 | Jansen et al. | |
| 6,237,649 B1 | 5/2001 | Moisio et al. | |
| 6,238,372 B1 | 5/2001 | Zinger et al. | |
| 6,269,976 B1 | 8/2001 | DeJonge | |
| 6,343,629 B1 | 2/2002 | Wessman et al. | |
| 6,355,023 B1 | 3/2002 | Roth et al. | |
| 6,364,865 B1 | 4/2002 | Lavi et al. | |
| 6,379,340 B1 | 4/2002 | Zinger et al. | |
| 6,409,708 B1 | 6/2002 | Wessman | |
| 6,453,956 B2 | 9/2002 | Safabash | |
| 6,474,375 B2 | 11/2002 | Spero et al. | |
| 6,475,183 B1 | 11/2002 | Epstein et al. | |
| 6,503,240 B1 | 1/2003 | Niedospial et al. | |
| 6,544,246 B1 | 4/2003 | Niedospial | |
| 6,551,299 B2 | 4/2003 | Miyoshi et al. | |
| 6,558,365 B2 | 5/2003 | Zinger et al. | |
| 6,571,837 B2 | 6/2003 | Jansen et al. | |
| 6,582,415 B1 | 6/2003 | Fowles et al. | |
| 6,598,765 B2 | 7/2003 | Pagel et al. | |
| 6,610,040 B1 | 8/2003 | Fowles et al. | |
| 6,638,244 B1 | 10/2003 | Reynolds | |
| 6,645,171 B1 | 11/2003 | Robinson et al. | |
| 6,645,179 B1 | 11/2003 | Ishikawa et al. | |
| 6,656,433 B2 | 12/2003 | Sasso | |
| 6,663,593 B2 | 12/2003 | Ito | |
| 6,666,852 B2 | 12/2003 | Niedospial | |
| 6,699,229 B2 * | 3/2004 | Zinger et al. | 604/410 |
| 6,719,719 B2 | 4/2004 | Carmel et al. | |
| 6,752,180 B2 | 6/2004 | Delay | |
| 6,817,987 B2 | 11/2004 | Vetter et al. | |
| 6,832,994 B2 | 12/2004 | Niedospial et al. | |
| 6,852,103 B2 | 2/2005 | Fowles et al. | |
| 6,875,203 B1 | 4/2005 | Fowles et al. | |
| 6,875,205 B2 | 4/2005 | Leinsing | |
| 6,890,328 B2 | 5/2005 | Fowles et al. | |
| 6,901,975 B2 | 6/2005 | Aramata et al. | |
| 6,948,522 B2 | 9/2005 | Newbrough et al. | |
| 6,994,315 B2 | 2/2006 | Ryan et al. | |
| 6,997,917 B2 | 2/2006 | Niedospial et al. | |
| 7,074,216 B2 | 7/2006 | Fowles et al. | |
| 7,077,835 B2 | 7/2006 | Robinson et al. | |
| 7,140,401 B2 | 11/2006 | Wilcox et al. | |
| 7,261,698 B2 | 8/2007 | Sampson et al. | |
| 7,294,122 B2 | 11/2007 | Kubo et al. | |
| D561,348 S | 2/2008 | Zinger et al. | |
| 7,326,194 B2 | 2/2008 | Zinger et al. | |
| 7,358,505 B2 | 4/2008 | Woodworth et al. | |
| 7,425,209 B2 | 9/2008 | Fowles et al. | |
| 7,442,189 B2 | 10/2008 | Curutcharry | |
| 7,491,197 B2 | 2/2009 | Jansen et al. | |
| 7,507,227 B2 | 3/2009 | Fangrow | |
| 7,510,548 B2 | 3/2009 | Fangrow | |
| 7,632,261 B2 | 12/2009 | Zinger et al. | |
| 7,806,874 B2 | 10/2010 | Funamura | |
| 7,998,106 B2 * | 8/2011 | Thorne et al. | 604/32 |
| 2001/0021820 A1 | 9/2001 | Lynn | |
| 2002/0066715 A1 | 6/2002 | Niedospial | |
| 2002/0087118 A1 | 7/2002 | Reynolds et al. | |
| 2002/0087144 A1 | 7/2002 | Zinger et al. | |
| 2002/0095121 A1 | 7/2002 | Norton et al. | |
| 2002/0115980 A1 | 8/2002 | Niedospial et al. | |
| 2002/0124905 A1 | 9/2002 | Draughn et al. | |
| 2003/0032935 A1 | 2/2003 | Damiano et al. | |
| 2003/0153895 A1 | 8/2003 | Leinsing | |
| 2003/0199846 A1 | 10/2003 | Fowles et al. | |
| 2004/0024354 A1 | 2/2004 | Reynolds | |
| 2004/0073189 A1 | 4/2004 | Wyatt et al. | |
| 2004/0112457 A1 | 6/2004 | Norton et al. | |
| 2004/0115099 A1 | 6/2004 | Smith | |
| 2004/0199139 A1 | 10/2004 | Fowles et al. | |
| 2004/0210207 A1 | 10/2004 | Amisar et al. | |
| 2004/0225274 A1 * | 11/2004 | Jansen et al. | 604/411 |
| 2004/0249341 A1 * | 12/2004 | Newbrough et al. | 604/87 |
| 2005/0124964 A1 | 6/2005 | Niedospial et al. | |
| 2005/0137523 A1 | 6/2005 | Wyatt et al. | |
| 2005/0137566 A1 | 6/2005 | Fowles et al. | |
| 2005/0148994 A1 | 7/2005 | Leinsing | |
| 2005/0151105 A1 | 7/2005 | Ryan et al. | |
| 2006/0025724 A1 * | 2/2006 | Chen | 604/249 |
| 2006/0025747 A1 | 2/2006 | Sullivan et al. | |
| 2006/0026482 A1 | 2/2006 | Fujisaki | |
| 2006/0030832 A1 | 2/2006 | Niedospial et al. | |
| 2006/0040340 A1 | 2/2006 | Greene | |
| 2006/0089594 A1 | 4/2006 | Landau | |
| 2006/0155257 A1 | 7/2006 | Reynolds | |
| 2006/0184103 A1 | 8/2006 | Paproski et al. | |
| 2006/0224105 A1 * | 10/2006 | Thorne et al. | 604/32 |
| 2007/0032775 A1 | 2/2007 | Niedospial et al. | |
| 2007/0060904 A1 | 3/2007 | Vedrine et al. | |
| 2007/0079894 A1 | 4/2007 | Kraus et al. | |
| 2007/0088252 A1 | 4/2007 | Pestotnik et al. | |
| 2007/0088313 A1 | 4/2007 | Zinger et al. | |
| 2007/0156112 A1 | 7/2007 | Walsh | |
| 2007/0167904 A1 | 7/2007 | Zinger et al. | |
| 2007/0270778 A9 | 11/2007 | Zinger et al. | |
| 2008/0009789 A1 | 1/2008 | Zinger et al. | |
| 2008/0021381 A1 | 1/2008 | Lurvey et al. | |

(56) References Cited

U.S. PATENT DOCUMENTS

| | | |
|---|---|---|
| 2008/0132851 A1 | 6/2008 | Shaw et al. |
| 2008/0140021 A1 | 6/2008 | Richmond |
| 2008/0172024 A1 | 7/2008 | Yow |
| 2008/0249479 A1 | 10/2008 | Zinger et al. |
| 2008/0283741 A1 | 11/2008 | Mukaibatake |
| 2009/0024096 A1 | 1/2009 | Hai et al. |
| 2009/0054834 A1 | 2/2009 | Zinger et al. |
| 2009/0062732 A1 | 3/2009 | Radmer |
| 2009/0082734 A1 | 3/2009 | Walters et al. |
| 2009/0082750 A1 | 3/2009 | Denenburg et al. |
| 2009/0099547 A1 | 4/2009 | Radmer |
| 2009/0177177 A1 | 7/2009 | Zinger et al. |
| 2009/0198217 A1 | 8/2009 | Thorne et al. |
| 2009/0204066 A1 | 8/2009 | Radmer et al. |
| 2009/0216184 A1 | 8/2009 | Radmer et al. |
| 2009/0275895 A1 | 11/2009 | Sie et al. |
| 2009/0299288 A1 | 12/2009 | Sie et al. |

FOREIGN PATENT DOCUMENTS

| | | |
|---|---|---|
| EP | 0 814 866 B1 | 6/2001 |
| EP | 1 192 966 B1 | 4/2002 |
| EP | 0 737 484 B1 | 8/2002 |
| EP | 0 815 886 B1 | 10/2003 |
| EP | 1 145 702 B1 | 5/2010 |
| JP | 57-037260 | 3/1982 |
| JP | 57-038142 | 3/1982 |
| JP | 3-236848 A | 10/1991 |
| JP | 11-503627 T | 3/1999 |
| JP | 2004-257776 A | 9/2004 |
| JP | 2007-301264 A | 11/2007 |
| WO | WO 96/29113 | 9/1996 |
| WO | WO 97/20536 | 6/1997 |
| WO | WO 2004/108192 A1 | 12/2004 |
| WO | WO 2007/000066 A1 | 1/2007 |

OTHER PUBLICATIONS

Japanese Patent Office, Japanese Application No. 2011-503152 Office Action dated Apr. 30, 2013, pp. 1-11.

Chinese Patent Office, Chinese Patent Application No. 2011-503152 Office Action dated Mar. 25, 2014, pp. 1-7.

* cited by examiner

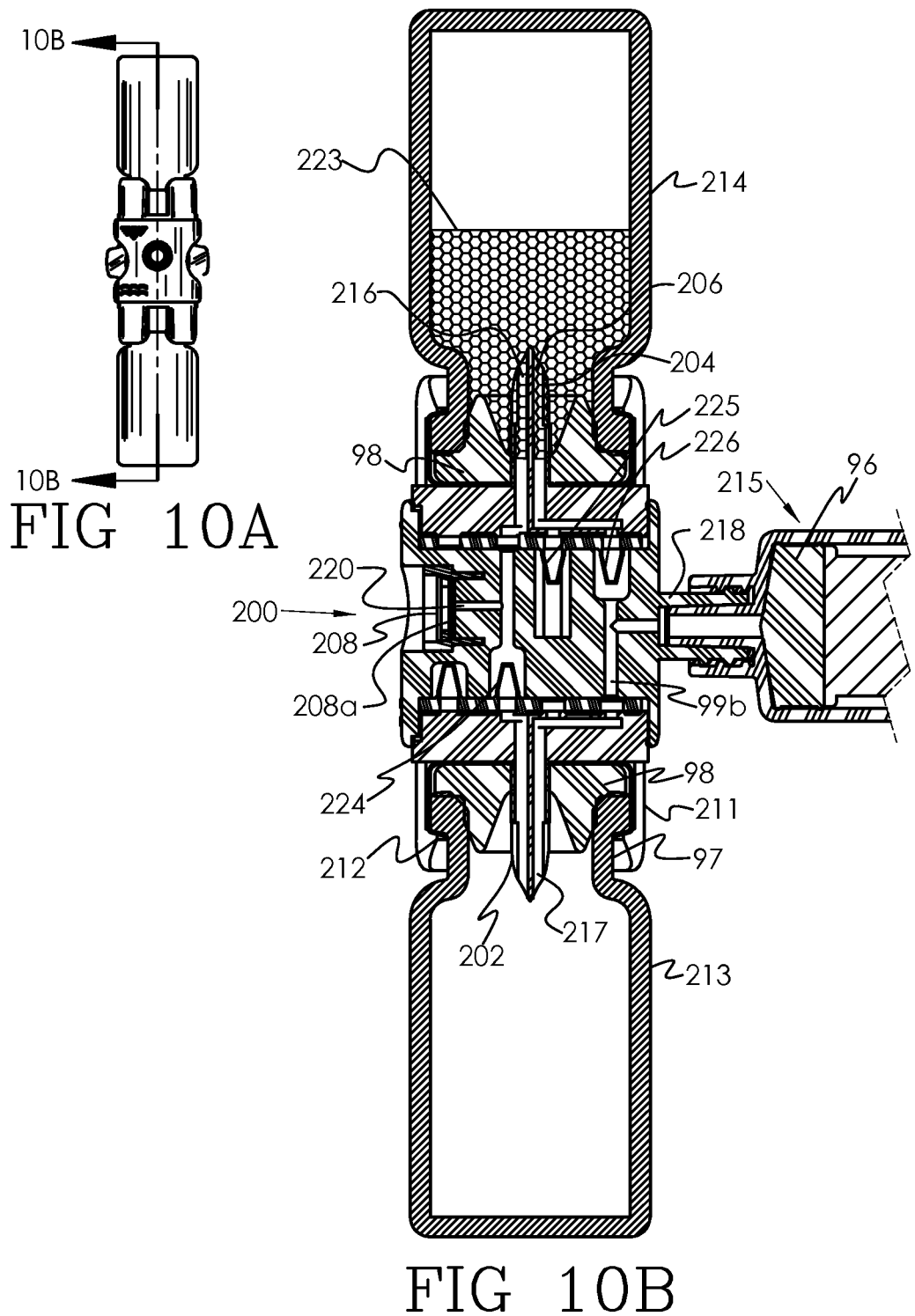

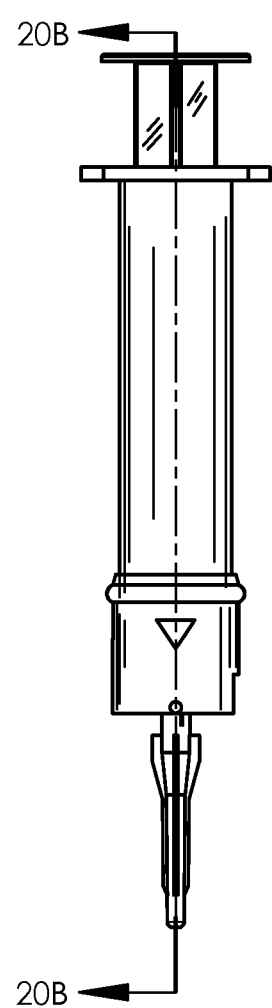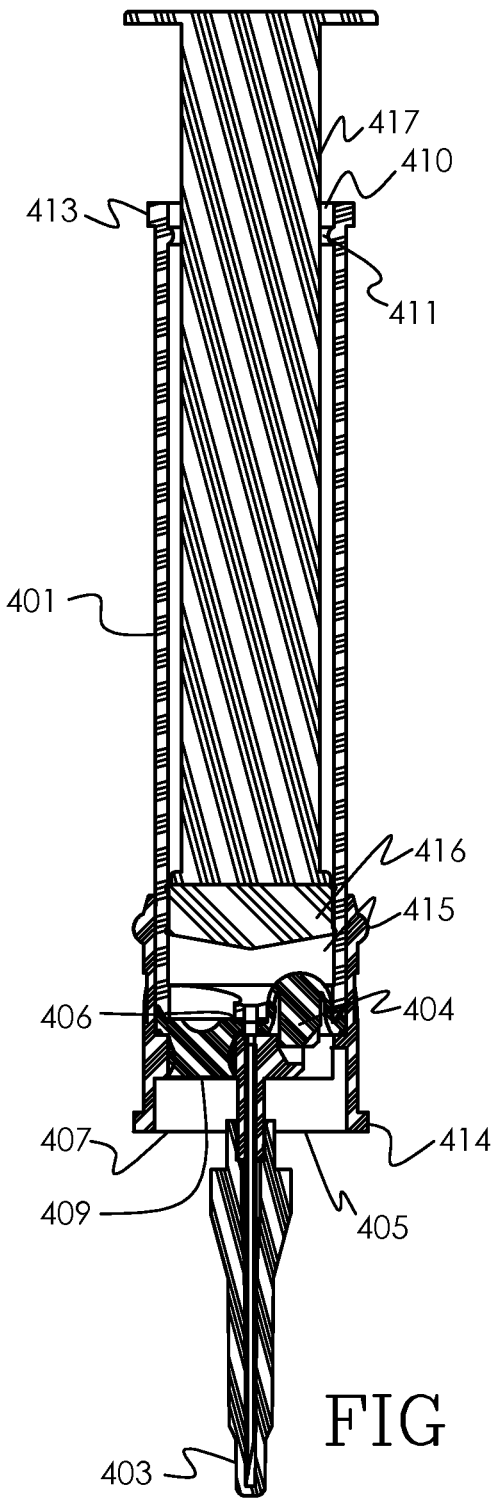
FIG 20A
FIG 20B

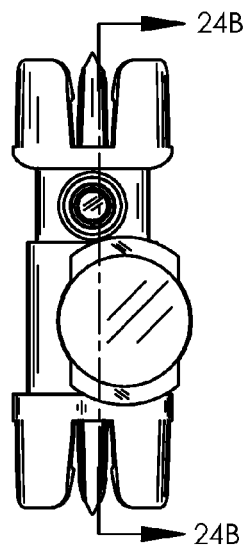
FIG 24A
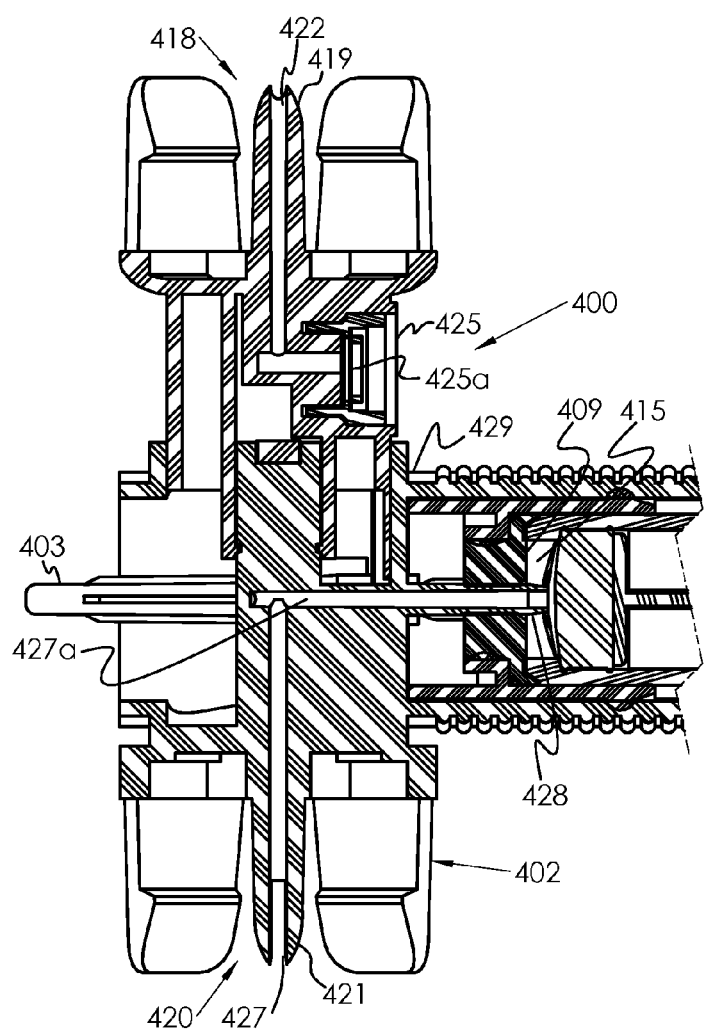
FIG 24B
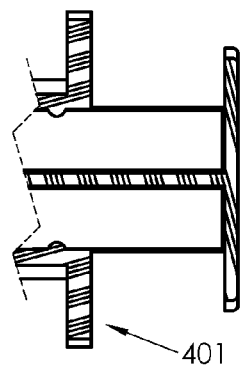

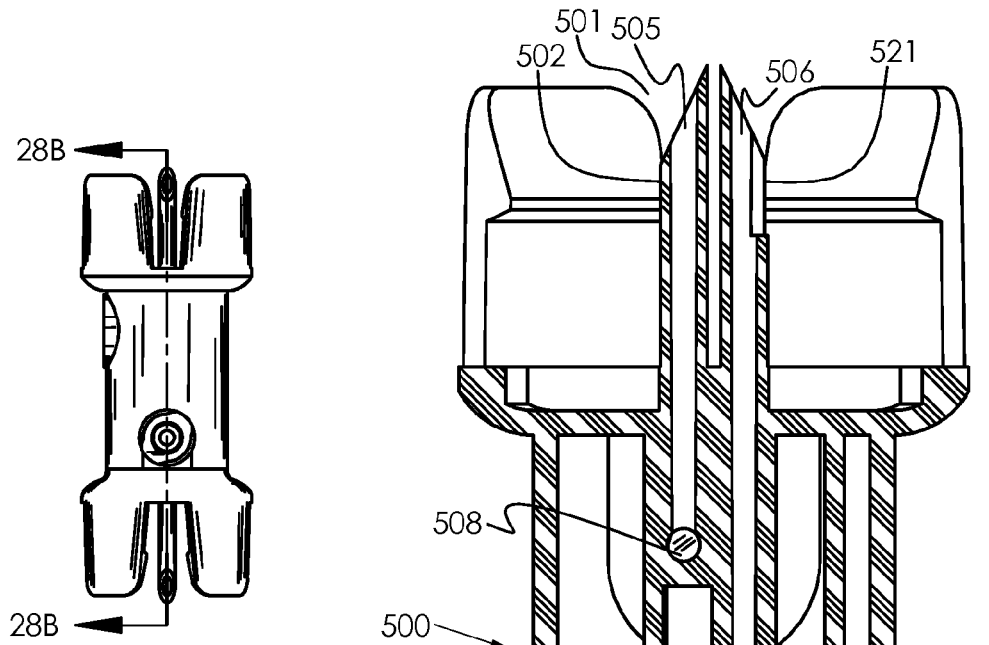
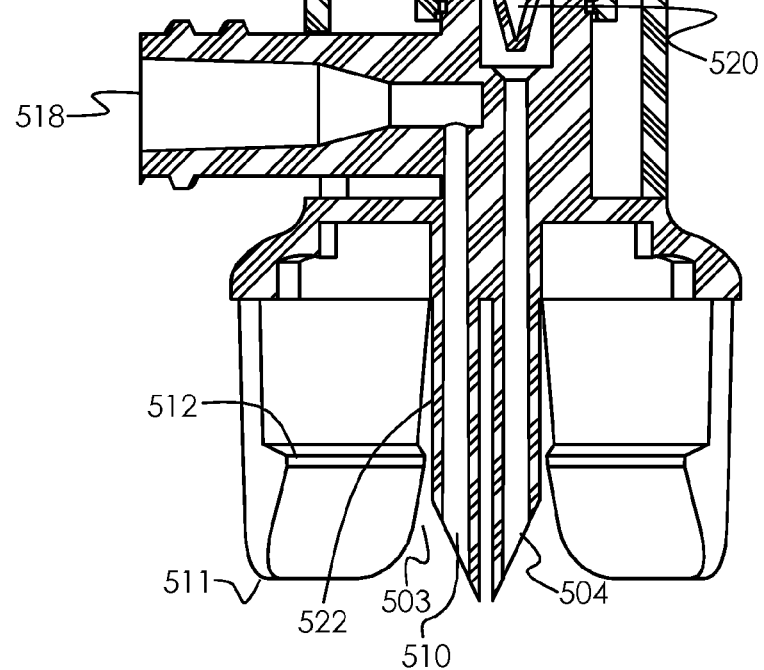
FIG 28A
FIG 28B

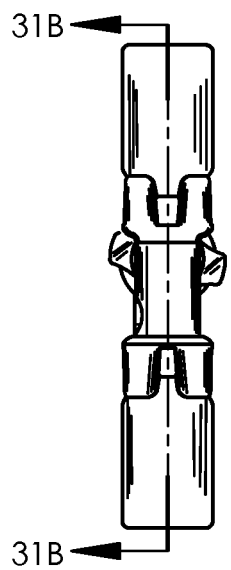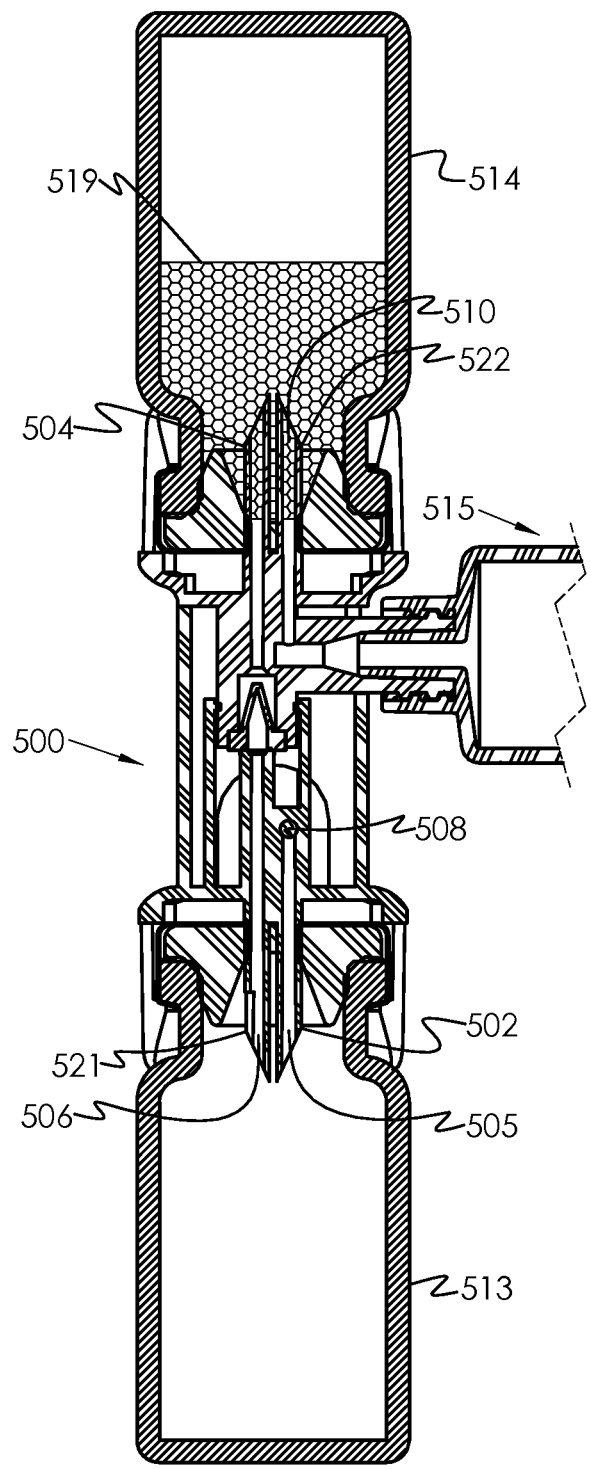
FIG 31A
FIG 31B

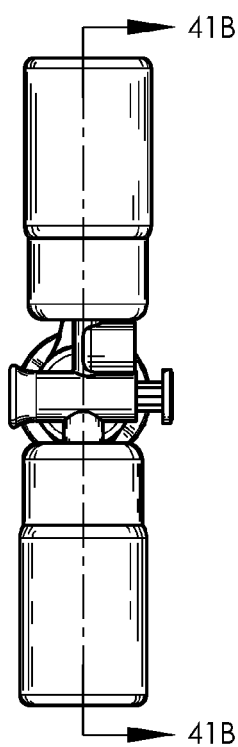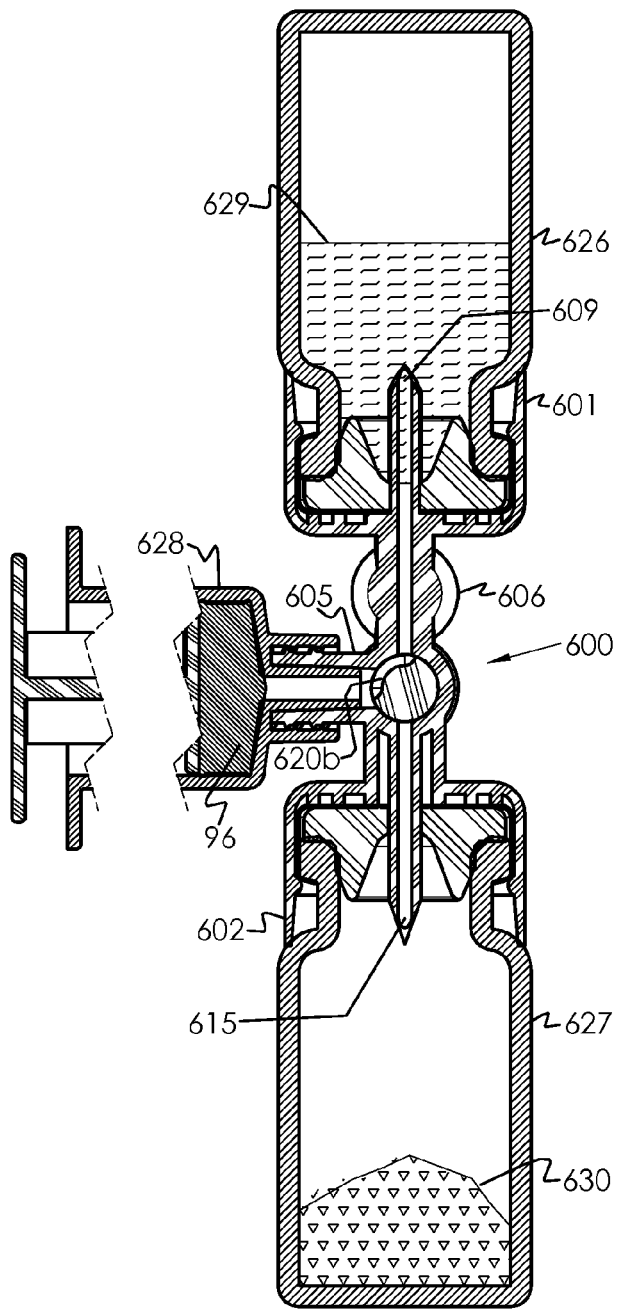
FIG 41A
FIG 41B

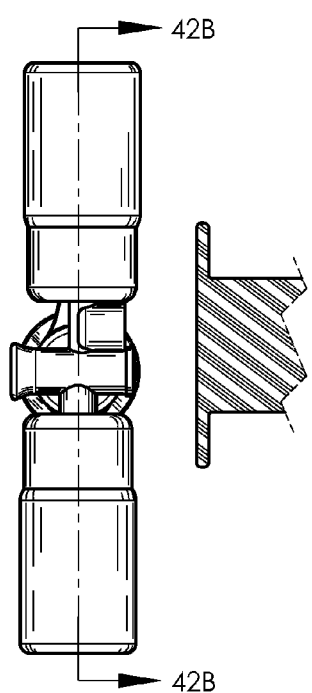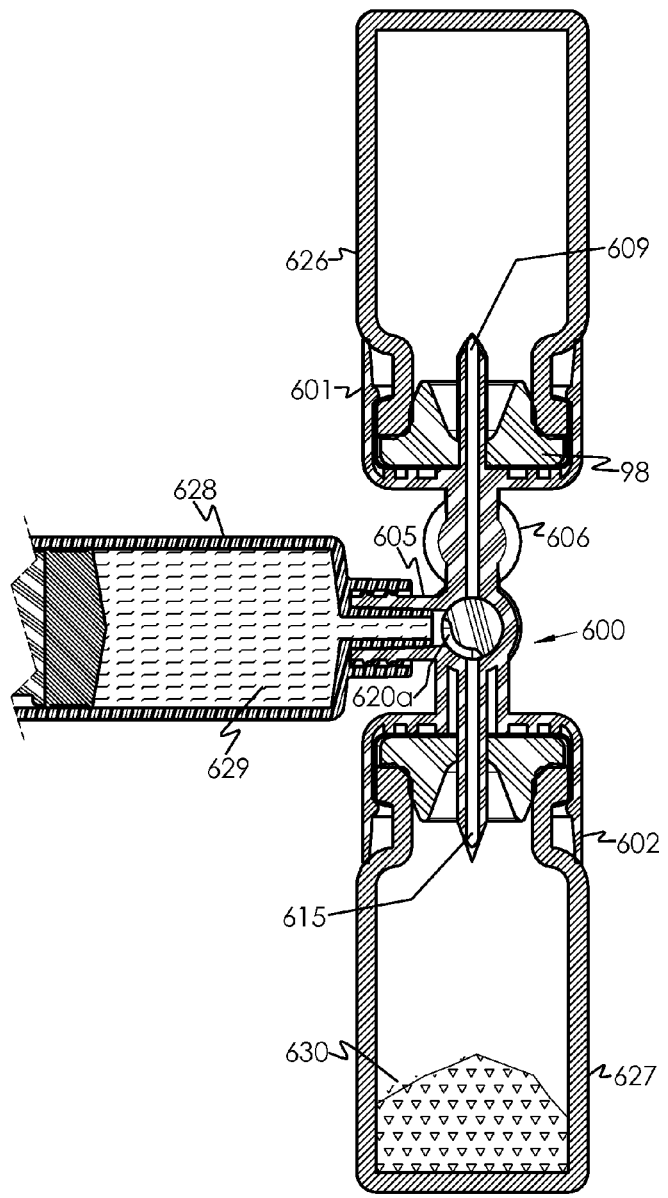
FIG 42A
FIG 42B

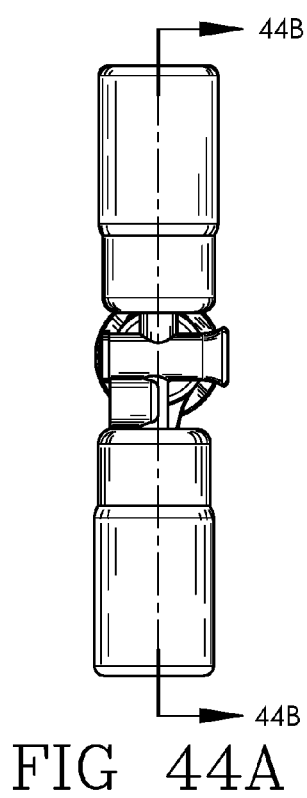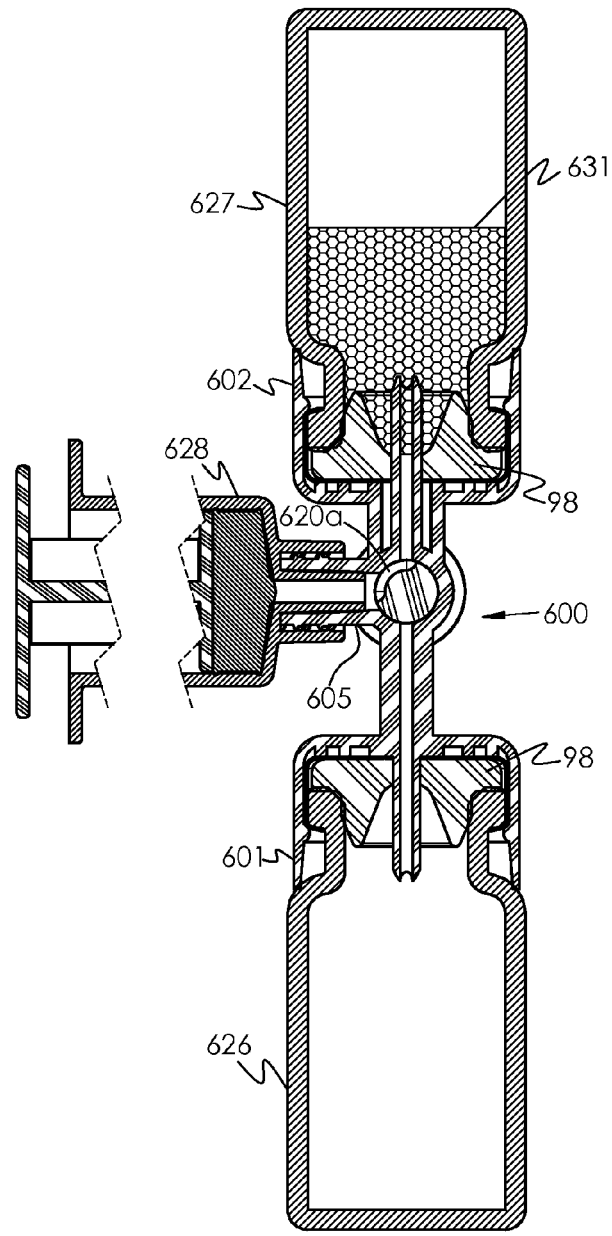
FIG 44A
FIG 44B

DUAL CONTAINER FLUID TRANSFER DEVICE

CROSS-REFERENCE TO RELATED APPLICATIONS

This patent application is a continuation-in-part of International Application No. PCT/US09/039215, filed Apr. 1, 2009, which claims the benefit of U.S. Provisional application Ser. No. 61/072,543, filed Apr. 1, 2008, U.S. Provisional application Ser. No. 61/133,179, filed Jun. 26, 2008, and U.S. Provisional application Ser. No. 61/201,964, filed Dec. 17, 2008, the entire contents of each being incorporated by reference in their entirety.

FIELD OF INVENTION

The invention relates to a fluid transfer device, for example for medical fluids, with a housing, access means associated with the housing for transfer of fluid from the transfer device, and a piercing assembly associated with the housing. The fluid transfer device also may provide metering of the fluid that is transferred to and/or from the containers accessed by the piercing members.

BACKGROUND

In medical technology, it may be necessary to transfer a substance from a first container, for example a container, a vial or an IV bag, to a second container, for example a vial or an IV bag for dissolution or suspension and possibly the withdraw of the dissolved or suspended material back into one of the containers or to a fluid delivery device, such as a syringe.

Drugs intended for parenteral administration are typically stored in a sealed container either as a dry powder, liquid concentrate, suspension, or as a solution. The contents of the container may also be immediately used with a physiological solution prior to administration in a similar manner to a dry powder drug. The physiological solution can be provided via a pre-filled syringe or vial, IV bag, or other medicinal vessel.

Sealed containers typically fall into one of three categories. The first type is a vial or a glass bottle closed by a rubber stopper which can be penetrated by a puncturing element, and which is self-closing upon withdrawal of the puncturing device. Such a vial or glass bottle can contain a single dose or a multiple dose of a drug. The drug contained in such a vial can be under reduced pressure. The second type of container is an ampoule whose top portion is broken off enabling access to its contents. The third type is an IV bag provided with a sample port for accessing its contents. The sample port can be of the pre-slit septum type or may require puncturing.

Typically, a transfer device with a piercing element is inserted into the rubber or other closures, respectively, providing communication between the two containers. The transfer of the fluid may be assisted by the fact that there is a vacuum in the inside of the container containing the substance to be dissolved or diluted. Other flow channels may be present and may be routed through the piercing members, to facilitate pressure compensation between the two containers, if there is no vacuum in the container or if the user does not correctly assemble the containers with the transfer device. The transfer of the fluid typically takes place with the fluid-containing container located above the container with the substance to be dissolved or suspended, so that the fluid can enter with gravitational assistance. Unfortunately, conventional transfer devices fall short of providing simple fluid transfer, for a variety of reasons, some of which include improper use of the device, loss of vacuum in the drug-containing vessel, exposure to vapors created by the rapid equilibration of pressure, etc.

Regardless of the manner in which a drug is stored, there is a continuous need to transfer fluid under sterile conditions before its administration to a patient. When a prior dilution of a drug is required, the process requires at least two fluid transfers. The problem of ensuring proper fluid transfer under aseptic conditions and without the accidental release of aerosols associated with the drug or its solution is especially acute in the case of chemotherapeutic drugs or for self-administration by users in their domiciles.

SUMMARY

A transfer device of the type disclosed and described can be operated easily and safely by the user, so that the reconstitution may be metered by the user, and so that user exposure to vapors from the drugs and their solutions are reduced. It should additionally be straightforward and inexpensive to produce and assemble. Such a transfer device is not only suitable for dissolving a medicament, but also for mixing two fluids, for transferring a gas, etc.

In a first embodiment, a fluid transfer device is provided where the device comprises a housing. A connector coupled to the housing is configured to receive a fluid delivery device. A first piercing assembly is associated with the housing and is adapted for accessing a first container. The first piercing assembly comprises (i) a first piercing member comprising a first fluid conduit, and (ii) optionally a first vent conduit. A second piercing assembly is associated with the housing, and is adapted for accessing a second container. The second piercing assembly comprises (i) a second piercing member comprising a second fluid conduit in fluid communication with the first fluid conduit of the first piercing member, (ii) a third fluid conduit in fluid communication with the connector, and (iii) optionally a filter associated with the second fluid conduit.

In a first aspect of the first embodiment, the fluid transfer device, in combination with the preceding aspect of the first embodiment, the fluid communication is essentially one-way from the first fluid conduit of the first piercing assembly to the second fluid conduit of the second piercing assembly during use.

In a second aspect of the first embodiment, the fluid transfer device, in combination with any of the preceding aspects of the first embodiment, further comprises an orientational-dependent fluid flow control means for allowing fluid communication of at least one of the conduits of the first piercing assembly in a first orientation state and restricting or preventing fluid communication of at least one of the conduits of the first piercing assembly in a second orientation state.

In a third aspect of the first embodiment, the fluid transfer device, in combination with any of the preceding aspects of the first embodiment, the at least one of the first piercing assembly or the second piercing assembly comprises at least one additional piercing member. Optionally, the at least one additional piercing member comprises one of the conduits selected from the group consisting of the first fluid conduit, the first vent conduit, the second fluid conduit, and the third fluid conduit.

In a fourth aspect of the first embodiment, the housing of the fluid transfer device, in combination with any of the preceding aspects of the first embodiment, is adapted to receive a needle safety mechanism of a fluid delivery device.

In a fifth aspect of the first embodiment, one-way fluid communication from the first fluid conduit of the first piercing assembly to the second fluid conduit of the second piercing assembly employs a check valve in combination with any of the preceding aspects of the first embodiment.

In a sixth aspect of the first embodiment, the first piercing assembly and the second piercing assembly are oriented at an angle other than 180 degrees relative to each other about the housing of the fluid transfer device, in combination with any of the preceding aspects of the first embodiment.

In a seventh aspect of the first embodiment, the fluid transfer device, in combination with any of the preceding aspects of the first embodiment, is essentially absent rotational means for controlling fluid communication between the containers or between the containers and the connector.

In an eighth aspect of the first embodiment, the connector of the fluid transfer device, in combination with any of the preceding aspects of the first embodiment, is a blunt cannula, a female luer connector or a male luer connector.

In a second embodiment, a fluid transfer device is provided where the device comprises a housing. A first piercing assembly is associated with the housing, and is configured for accessing a first container. The first piercing assembly comprises a first piercing member having at least one conduit. A second piercing assembly is associated with the housing, the second piercing assembly adapted for accessing a second container. The second piercing assembly comprising a second piercing member having at least one conduit. A connector coupled to the housing is adapted to receive a fluid delivery device. A user-actuated plunger is at least partially slidably disposed in the housing, the user-actuated plunger comprises at least one flow channel.

In a second aspect of the second embodiment, the user-actuated plunger of the fluid transfer device, in combination with the preceding aspect of the second embodiment, comprises a first flow channel and a second flow channel, the second flow channel being distally separated from the first flow channel; wherein the user-actuated plunger is configured to slidably move between (i) a first predetermined position wherein the first flow channel provides fluid communication between the connector and the at least one conduit of the first piercing member, and (ii) a second predetermined position, wherein the second flow channel provides fluid communication between the connector and the at least one conduit of the second piercing member.

In a third aspect of the second embodiment, the user-actuated plunger of the fluid transfer device, in combination with the preceding aspect of the second embodiment, provides metering of a predetermined amount of material from the first container to the connector.

In a fourth aspect of the second embodiment, the at least one flow channel of the fluid transfer device, in combination with any of the preceding aspects of the second embodiment, is positioned about the perimeter of the user-actuated plunger.

In a fifth aspect of the second embodiment, the user-actuated plunger of the fluid transfer device, in combination with any of the preceding aspects of the second embodiment, is restricted or prevented from rotation relative to the housing.

In a sixth aspect of the second embodiment, the connector of the fluid transfer device, in combination with any of the preceding aspects of the second embodiment, is a blunted cannula, a female luer connector, or a male luer connector.

In a seventh aspect of the second embodiment, the user-actuated plunger of the fluid transfer device, in combination with any of the preceding aspects of the second embodiment, further comprises a third flow channel, and the user-actuated plunger is further configured to move to a predetermined third position, wherein the third fluid channel provides fluid communication between the second container and the first container.

In an eight aspect of the second embodiment, the user-actuated plunger of the fluid transfer device, in combination with the seventh aspect of the second embodiment, is prevented from positioning at the predetermined third position prior to use.

In a ninth aspect of the second embodiment, the user-actuated plunger of the fluid transfer device, in combination with any of the preceding aspects of the second embodiment, is at least partially or wholly a rigid material, a thermoplastic, a thermoplastic elastomer, a rigid material in combination with a thermoplastic elastomer or curable elastomer, a thermoplastic in combination with a thermoplastic elastomer or curable elastomer, a co-injected thermoplastic and thermoplastic elastomer, or curable elastomer.

In a third embodiment, a fluid transfer device is provided where the fluid transfer device comprises a housing. A first piercing assembly is associated with the housing and is configured for accessing a first container. The first piercing assembly comprises a first piercing member having at least one fluid conduit, optionally in combination with a filter. A second piercing assembly is associated with the housing and is adapted for accessing a second container. The second piercing assembly comprises a second piercing member having at least one fluid conduit, optionally in combination with a filter. A user-actuated plunger is at least partially slidably disposed in the housing, the user-actuated plunger comprising at least one flow channel. The user-actuated plunger is configured to slidably move between a first predetermined position wherein fluid communication between the first container and the second container is prevented, and a second predetermined position wherein the at least one flow channel provides fluid communication between the first container and the second container.

In a second aspect of the third embodiment, the at least one flow channel of the fluid transfer device, in combination with the preceding aspect of the third embodiment, is positioned about the perimeter of the user-actuated plunger.

In a third aspect of the third embodiment, the user-actuated plunger of the fluid transfer device, in combination with any of the preceding aspects of the third embodiment, is restricted or prevented from rotation relative to the housing.

In a fourth aspect of the third embodiment, the fluid transfer device, in combination with any of the preceding aspects of the third embodiment, further comprises a removable member adapted to engage the user-actuated plunger for preventing the user-actuated plunger from positioning at the predetermined second position.

The at least one of the first piercing assembly or the second piercing assembly of the fluid transfer device in combination with any of the preceding embodiments or any combinations of aspects of any embodiment may further comprise at least one additional piercing member, optionally the at least one additional piercing member having one of the conduits selected from the group consisting of the first fluid conduit, the first vent conduit, the second fluid conduit, and the third fluid conduit.

The fluid transfer device of any of the preceding embodiments or any combinations of aspects of any embodiment may further comprise a filter disposed in a flow path between any of the first and second piercing members and/or the connector.

Methods of transferring contents between containers and/or methods of transferring metered amounts of contents from one container to another without exposure of the user to the contents being transferred using the fluid transfer device of any of the preceding embodiments or any combinations of aspects of any embodiment, is provided. Thus, for the mixing and/or metering of the contents of at least two containers, at least one container comprises a liquid and at least one container comprises a material in the form of a solid, liquid, suspension, or combinations thereof.

Further features of the invention are set out in the patent claims, in the description of the figures, and in the figures themselves.

BRIEF DESCRIPTION OF THE DRAWINGS

FIGS. 10A & 10B depict a sectional plane and corresponding cross-sectional view, respectively, of an intermediate state of the device of FIG. 6.

FIGS. 20A & 20B depict a sectional plane and corresponding cross-sectional view, respectively, of the fluid delivery device of FIG. 18.

FIGS. 24A & 24B depict a sectional plane and corresponding cross-sectional view, respectively, of the fluid transfer device of FIG. 18 in a bypass access state.

FIGS. 28A & 28B depict a sectional plane and corresponding cross-sectional view, respectively, of the fluid transfer device of FIG. 27.

FIGS. 31A & 31B depict a sectional plane and corresponding cross-sectional view, respectively, of an intermediate use state of the fluid transfer device of FIG. 27.

FIGS. 41A & 41B depict a sectional plane and corresponding cross-sectional view, respectively, of the device of FIG. 39 in a first position and secured to two containers and a fluid delivery device.

FIGS. 42A & 42B depict a sectional plane and corresponding cross-sectional view, respectively, of the device of FIG. 39 in a second position with fluid transfer from a first container to the fluid delivery device.

FIGS. 44A & 44B depict a sectional plane and corresponding cross-sectional view, respectively, of the device of FIG. 39 in a second position with fluid transfer from the inverted second container to the fluid delivery device.

DETAILED DESCRIPTION

Throughout the specification, the term "fluid" as used herein is inclusive of gaseous, liquid, and combinations of gas and liquid medium unless specifically designated as limited to a particular medium.

Throughout the specification, the term "liquid" as used herein is inclusive of suspensions, oil-in-water emulsions, water-in-oil emulsions, and liquids with or without dissolved, dispersed, or contained solids irrespective of the size of the solids or the amount present.

Throughout the specification, the phrases "dual vial access device," "drug reconstitution device," and "fluid transfer device" are used interchangeably, unless otherwise stated, without any express or implied limitation to the scope of any claim. As is understood by one having ordinary skill in the art, a fluid transfer device provides for introduction of fluid from one vessel to another, while a fluid control device may include flow control means for diverting, metering, or interrupting flow between at least two flow paths. However, the phase "fluid transfer device" as used herein is inclusive of "fluid control devices."

Throughout the specification, the phrase "fluid transfer device" and the term "syringe" are used interchangeably unless otherwise stated, without any express or implied limitation to the scope of any claim, and are inclusive of any device with similar functionality to that of a syringe, but not necessarily the structure of a syringe.

The transfer device for the transfer of fluids between containers herein disclosed and described can be configured in a variety of ways. The transfer device may be used in connection with the transfer of a fluid into a container in which there is a vacuum. The piercing members are designed to penetrate the stoppers sealing the containers.

Figure 1:
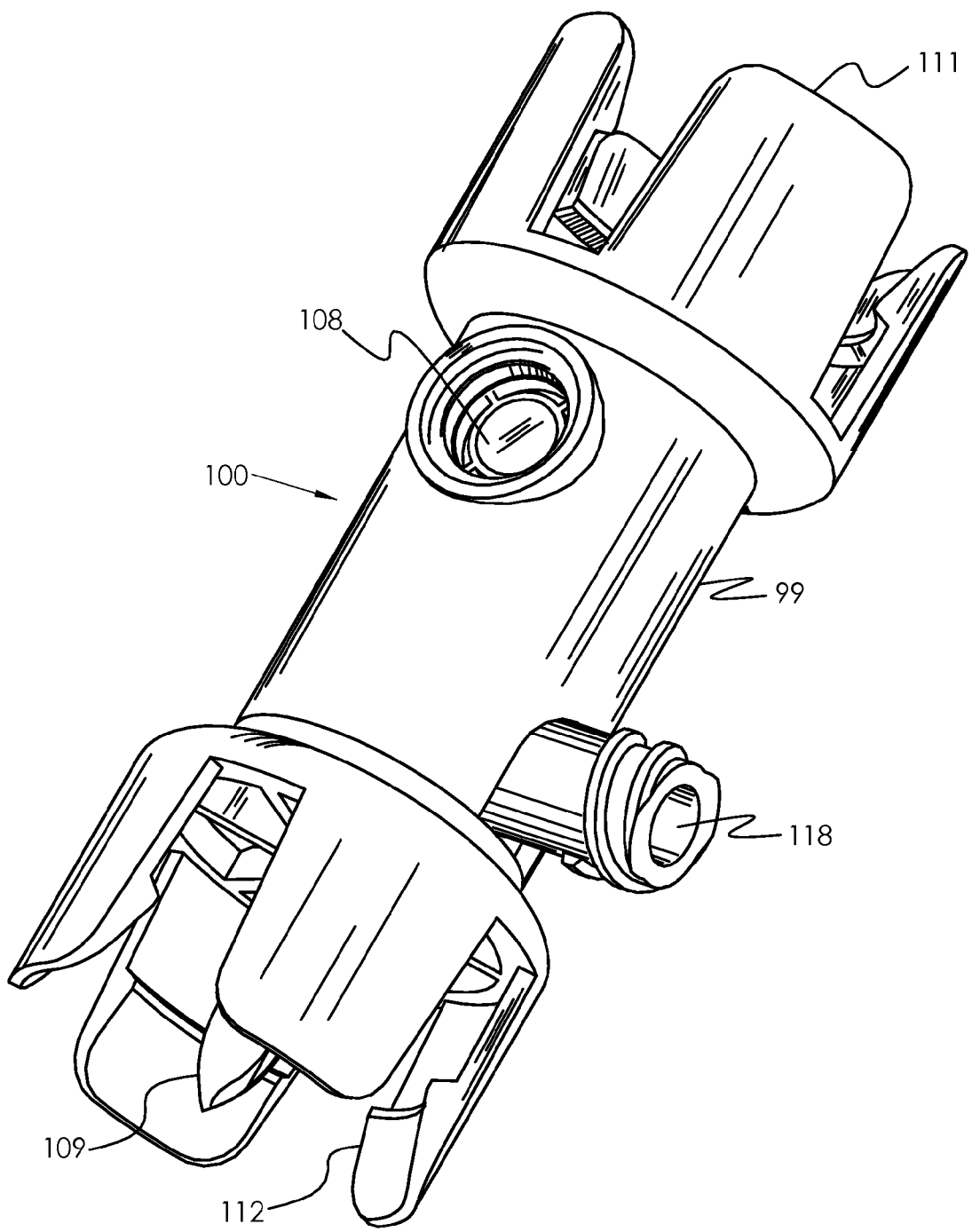
FIG. 1 is a perspective view of a fluid transfer device aspect as disclosed and described.
Figures 2A, 2B:
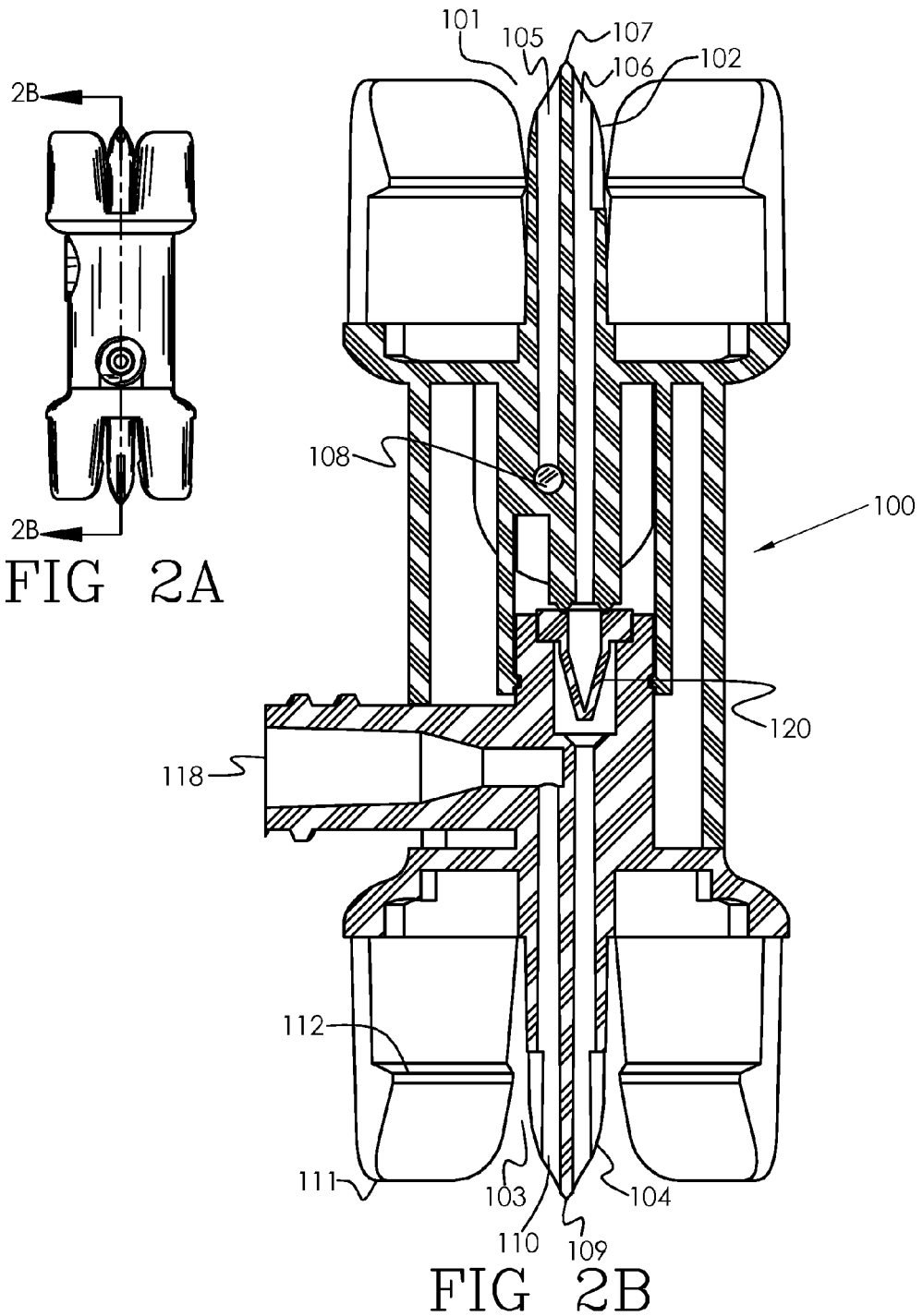
FIGS. 2A & 2B depict a sectional plane and corresponding cross-sectional view, respectively, of the device of FIG. 1.
Figure 3A:
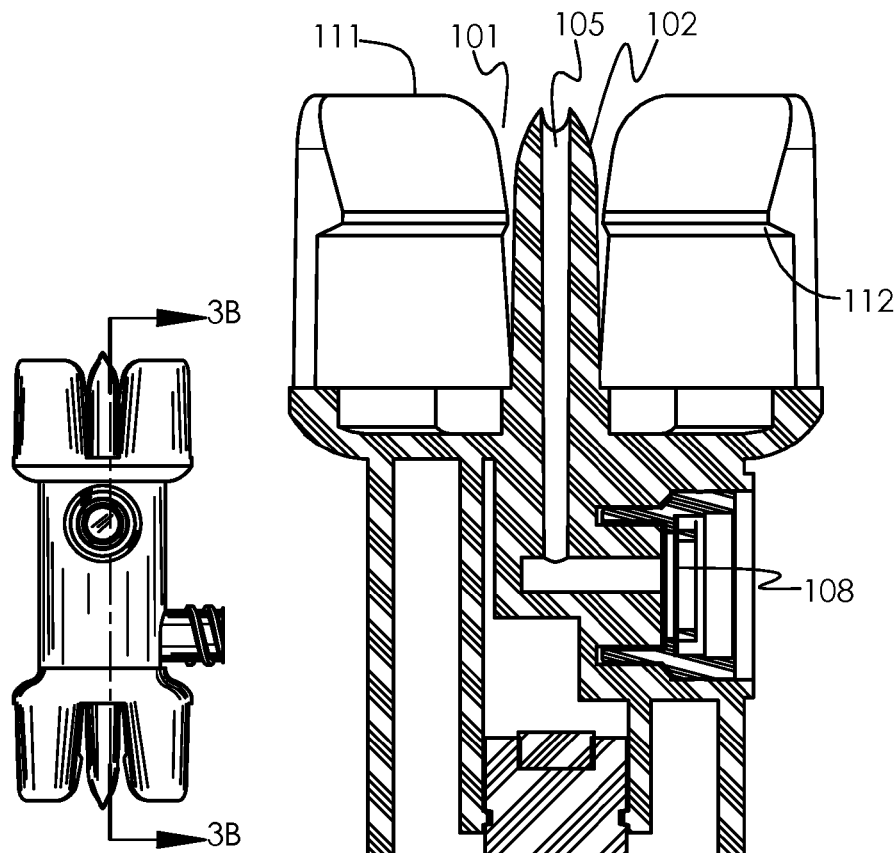
FIGS. 3A & 3B depict a sectional plane and corresponding cross-sectional view, respectively, of the device of FIG. 1.
Figure 3B:
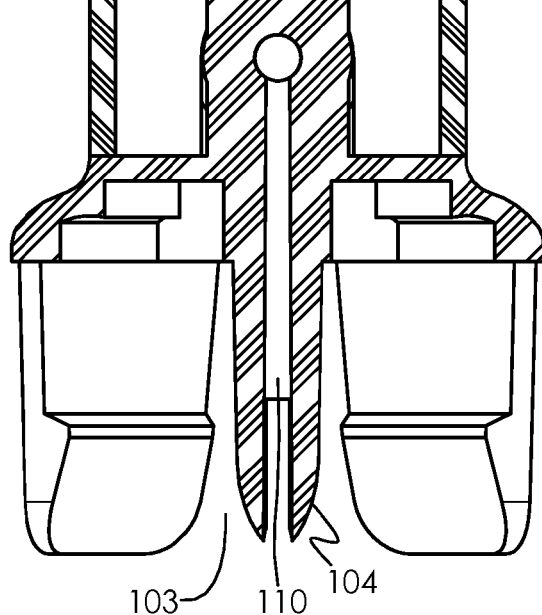

FIG. 1 is a perspective view of a fluid transfer device (100) having housing (99) with piercing assemblies (111) including skirt with attachment members (112) positioned at opposed ends showing one piercing member (having distal end 109).

The housing includes connector (118) for attachment of a fluid delivery device, such as a syringe, and further includes vent (108) with filter.

FIGS. 2A, 2B, 3A and 3B depict sectional planes and corresponding cross-sectional views of device (100) showing a first end (101) of a piercing assembly terminating in a first piercing member (102) and a second end (103) of another piercing assembly terminating in a second piercing member (104). The first piercing member includes at least one vent conduit (105) and at least one fluid conduit (106) each conduit open proximal to the first piercing member distal end (107) to provide for essentially complete transfer of fluid. Vent conduit(s) (105) provide fluid communication with the ambient surrounding the device and may include a filter (108)(e.g. hydrophobic). The fluid conduit(s) of the second piercing member open proximal to distal end (109) and provide one-way fluid communication from the first piercing member to the second piercing member via check valve (120) or other functionally similar devices known in the art. The second piercing member may optionally have a secondary fluid conduit (110) opening proximal to the second piercing member distal end (109) and terminating at a connector (118), which may of a luer-type. The piercing assemblies may have one or a plurality of attachment fingers (111a) with attachment means (112) proximal to the attachment finger distal end for securing to a container, such as a vial or IV bag port.

Figure 4A:
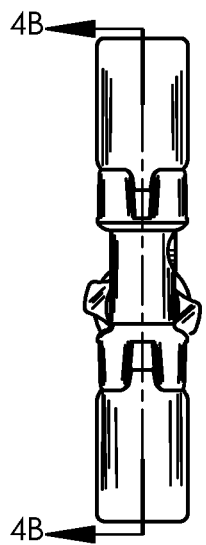
FIGS. 4A & 4B depict a sectional plane and corresponding cross-sectional view, respectively, of an initial use state of the embodiment of FIG. 1.
Figure 4B:
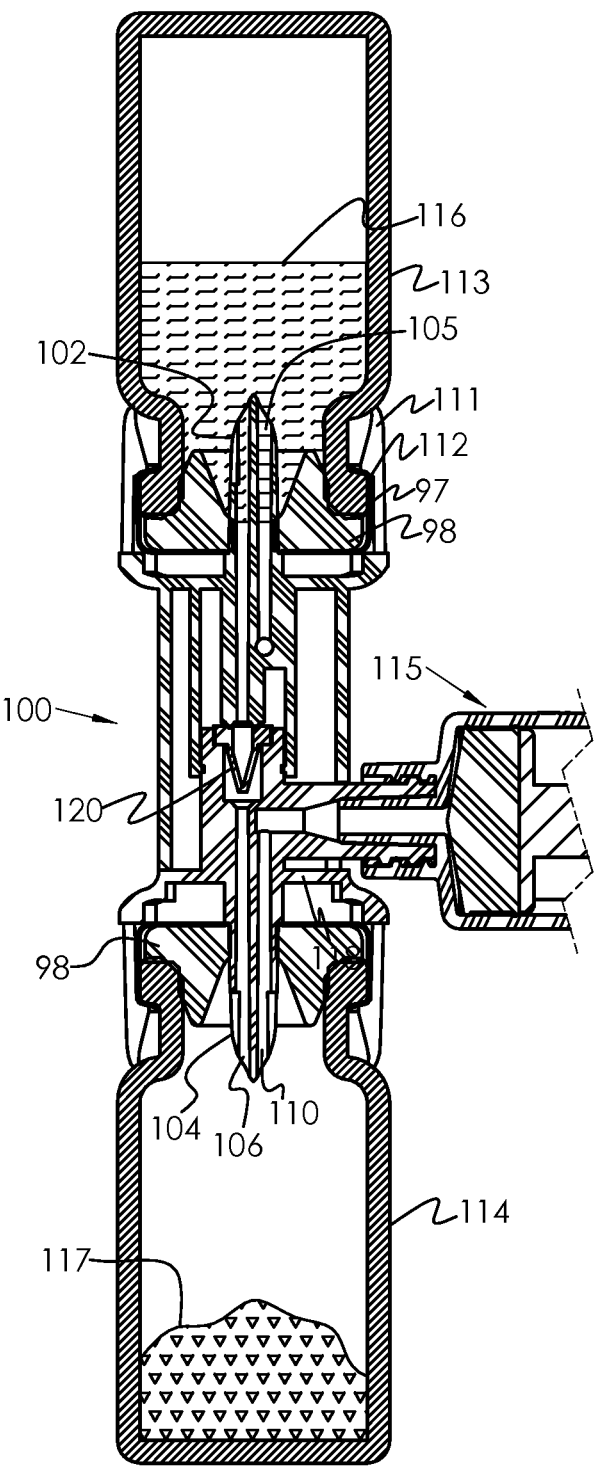
Figure 5A:
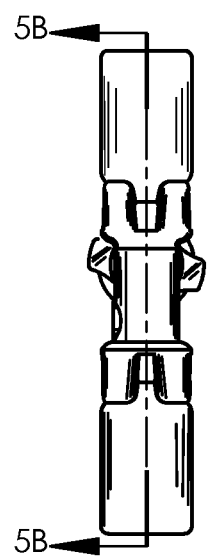
FIGS. 5A & 5B depict a sectional plane and corresponding cross-sectional view, respectively, of an intermediate use state of the device of FIG. 1.
Figure 5B:
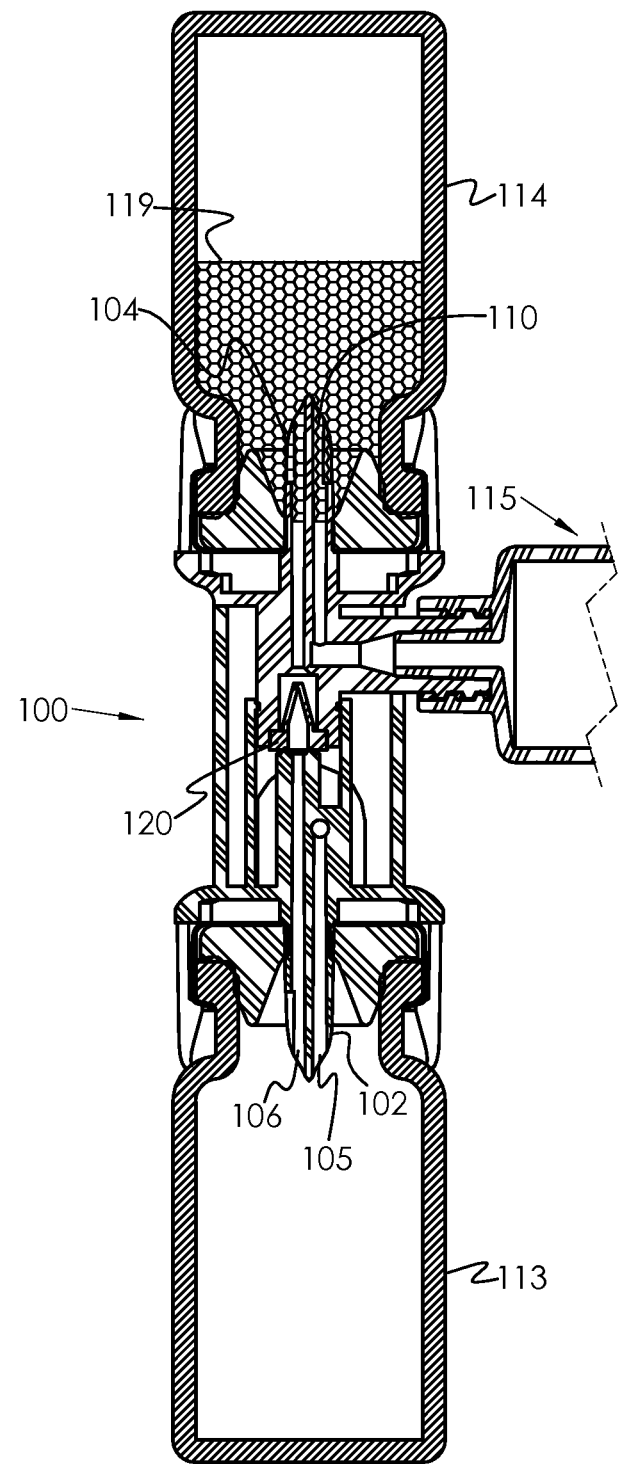

FIGS. 4A and 4B and FIGS. 5A and 5B depict sectional planes and cross-sectional views of an initial use state and in-use state of device (100), respectively, where in FIG. 4B the device is shown in an initial state with a first container (113) inverted above a second container (114) and a syringe (115) sealably attached. The first container contains a fluid (116) and the second container contains a second media (117) for example a solid drug form. In FIG. 5B, the device (100) shown in the in-use state with the second container (114) inverted above the first container (113) and a syringe (115) sealably attached. The second container may contain a mixture (119) of the first and second container contents in this state. In use, two methods may be employed to transfer fluid between the two containers, mix or dissolve the drug, and transfer the mixture to the syringe for administration or dispensing. In the first method of use, syringe (115) is used to create a pressure differential between the first and second container by withdrawing its plunger such that the fluid contained in the first container is inclined to fluidically navigate fluid conduit (106) for introduction into the second container through the second piercing member. During this time, air may be vented into the first container thru vent conduit (105) such that the pressure in the first container may be equalized. When an adequate amount of the fluid has been deposited into the second container, the second media may be mixed with the fluid in a fashion appropriate to the mixture. The device may then be inverted to an in-use state. Since the syringe plunger may be in the withdrawn state (air in the syringe), it may first be required to inject to pressurize the second container, then withdraw to pull the mixture out of the second container, thus doing so without the need to first disconnect the syringe. This also maintains ambient pressure in the second container upon completion of the withdrawal. In a second method of use for device (100), the procedure is the same up to the initial use state where a predetermined partial vacuum in the second media container (as is often found in lyophilized drug vials, for instance) automatically pulls the fluid from the first container to the second container. The second media may be mixed with the fluid in a fashion appropriate to the mixture, then the device may be inverted to an in-use state and the mixture may be directly withdrawn into the syringe.

Figure 6:
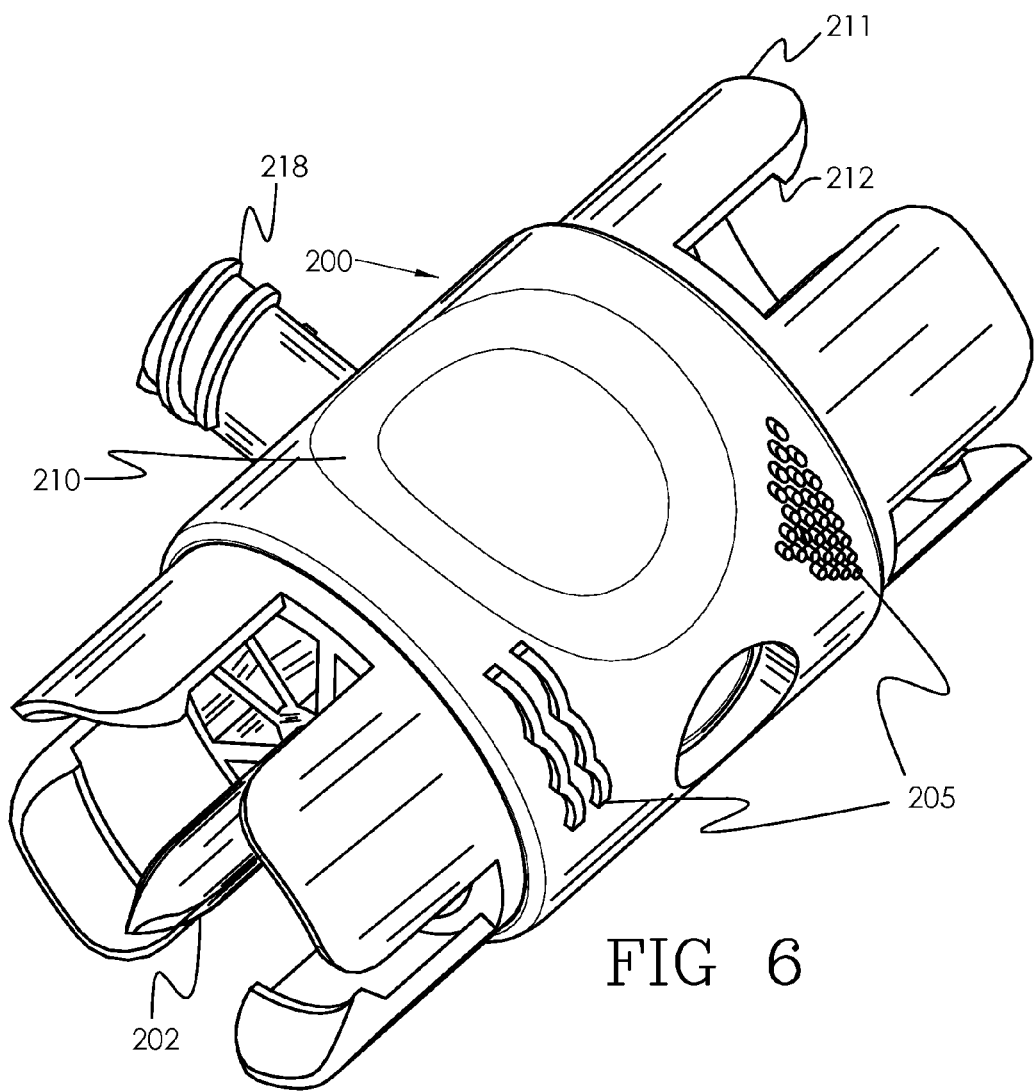
FIG. 6 a perspective view of a fluid transfer device aspect as disclosed and described.
Figures 7A, 7B:
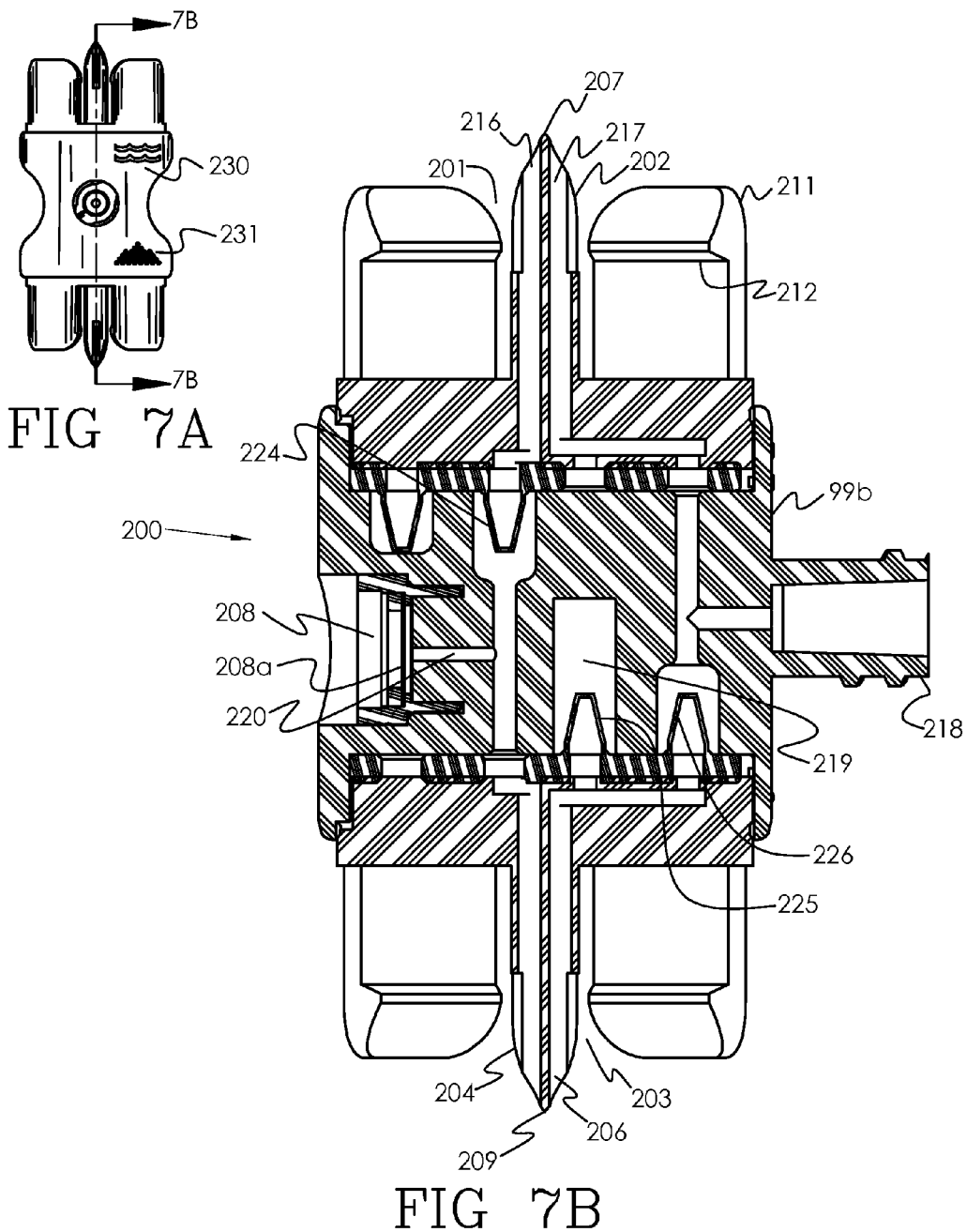
FIGS. 7A & 7B depict a sectional plane and corresponding cross-sectional view, respectively, of the device of FIG. 6.
Figures 8A, 8B:
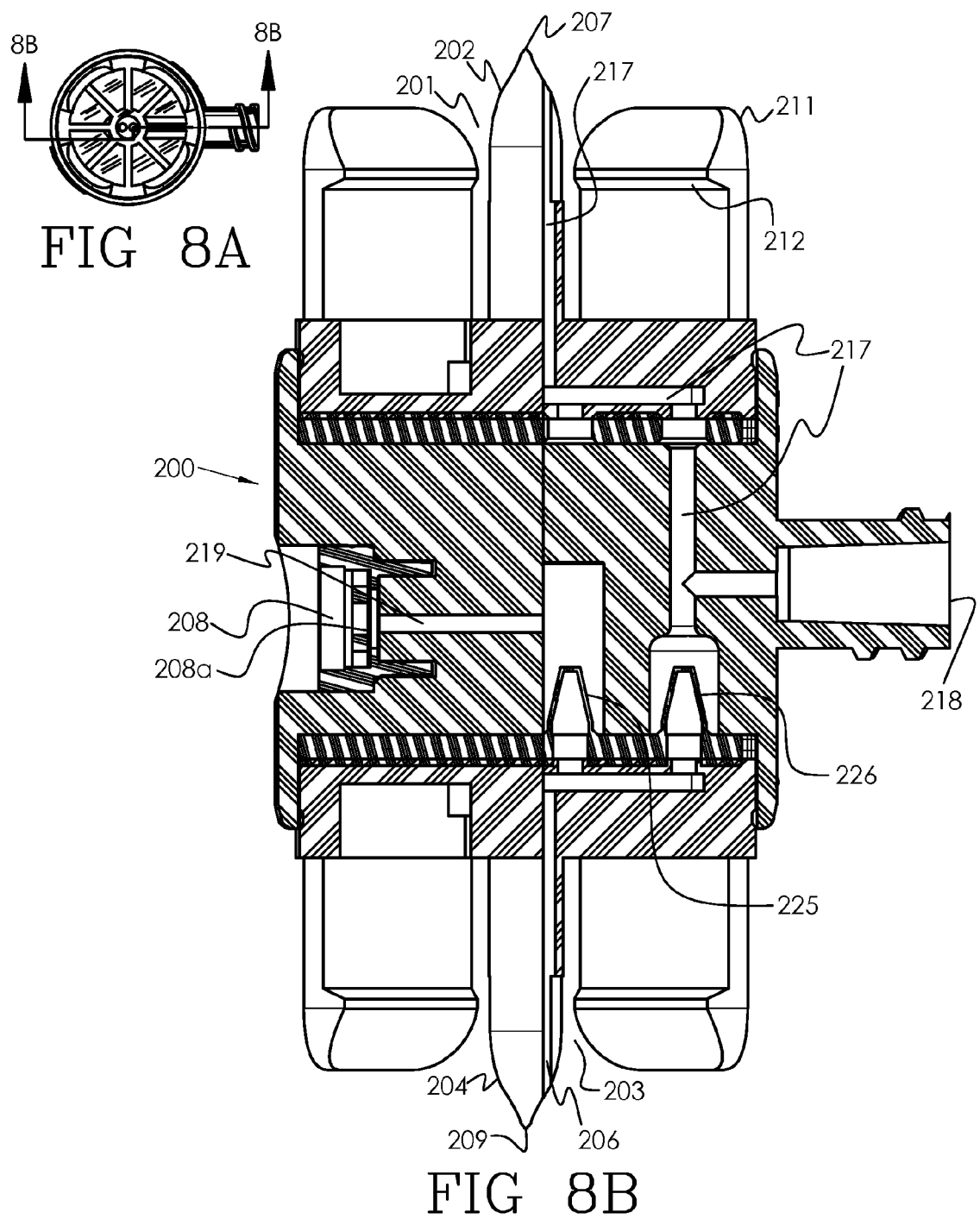
FIGS. 8A & 8B depict a sectional plane and corresponding cross-sectional view, respectively, of the device of FIG. 6.

FIG. 6 is a perspective view of a fluid transfer device (200). FIGS. 7A, 7B and 8A and 8B depict sectional planes (side view and top view) and corresponding cross-sectional views, respectively of fluid transfer device (200). Device (200) comprises piercing assemblies including a first end (201) terminating in a first piercing member (202) and a second end (203) terminating in a second piercing member (204). The first piercing member includes at least one fluid conduit (216) and at least one charge conduit (217) each open proximal to the first piercing member distal end (207). The charge conduit(s) may be in fluid communication with connector (218) which may be a luer of the locking or non-locking type. Fluid conduit (216) opens proximal to the second piercing member distal end (209) and is configured for one-way fluid communication between the ends of the fluid conduits by way of first check valve (224). Fluid conduit (216) includes access to first vent conduit (220), which is in fluid communication with the ambient surrounding the device via vent (208), the first vent conduit may have a filter element (208a) at any point along its path, such as hydrophobic filter media. Second piercing member (204) may also have a fluid conduit (206) open proximal to the second piercing member distal end (209) and is in fluid communication with connector. Fluid conduit (206) includes a second vent conduit (219) in fluid communication with the ambient surrounding the device via vent (208). The second vent conduit is configured for one-way flow out to ambient via a second check valve (225) and may have a filter element at a point along its path which may be the filter element for vent conduit (220), or, alternately, a second filter element. Fluid conduit (217) is configured for one-way media flow in the direction of connector and away from the second piercing member distal end, via a third check valve (226). Either or both of the first and second piercing members may also have a skirt including one or a plurality of attachment fingers (211) which may have attachment means (212) proximal to the attachment finger distal end for securing the piercing assembly of the device to a container such as a vial or IV bag. The device may include indicia, which may be molded in, or other similar visual or tactile cues to indicate to the user which side of the device to attach the fluid (230) and which side of the device to attach the media (231).

Figures 9A, 9B:
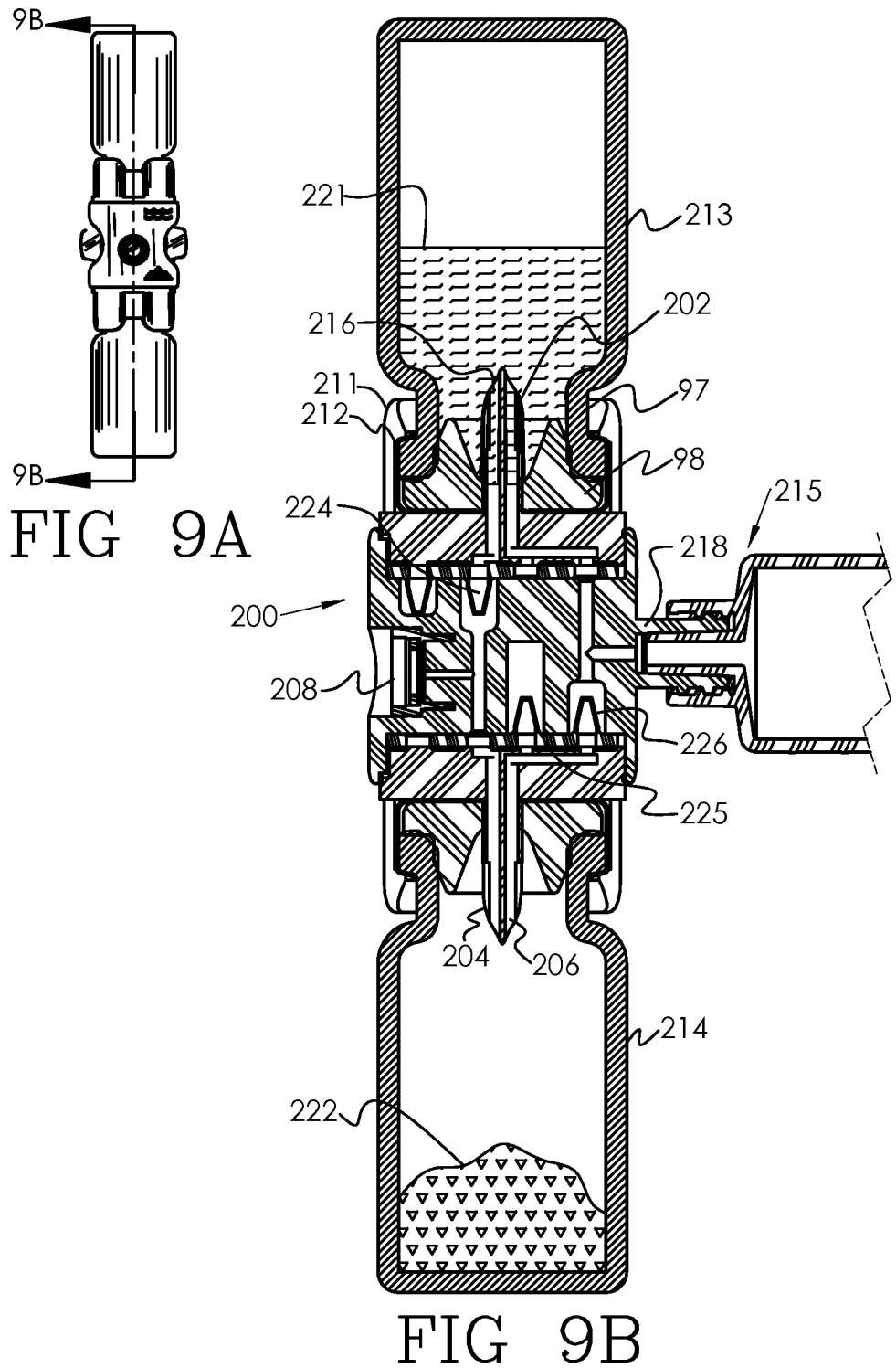
FIGS. 9A & 9B depict a sectional plane and corresponding cross-sectional view, respectively, of an initial use state of the device of FIG. 6.

FIGS. 9A and 9B depict a sectional plane and a cross-sectional view, respectively, of an initial use state of fluid transfer device (200) shown with a first container (213) inverted above a second container (214) and a syringe (215) sealably attached—the first container containing a fluid (221), the second container containing a second media (222). Syringe (215) is shown filled with an appropriate volume of air. FIGS. 10A and 10B depict a sectional plane and a cross-sectional view, respectively, of an intermediate state of fluid transfer device (200) shown with second container (214) inverted above first container (213) and syringe (215) sealably attached. The second container may contain a mixture (223) of the first and second container contents in this state. The syringe is used to draw the mixture into its inner containment portion. In use, device (200) may be as operated by attaching to the device syringe (215) pre-loaded with gas such as air. Injecting the gas into device connector (218) in the orientation shown in FIG. 9B provides a positive pressure in first container (213) thereby forcing the fluid therein to be introduced into second container (214) containing media (222). Pressure in the system may be equalized through second vent conduit (219). Second container (214) with media may then be mixed with the fluid in a fashion appropriate to the mixture. The device may then be inverted as shown in FIG. 10B. Syringe 215 may be used to draw in the mixture (223) for administration or dispensing. Pressure in the second container may be equalized through the first vent conduit (220).

Figure 11:
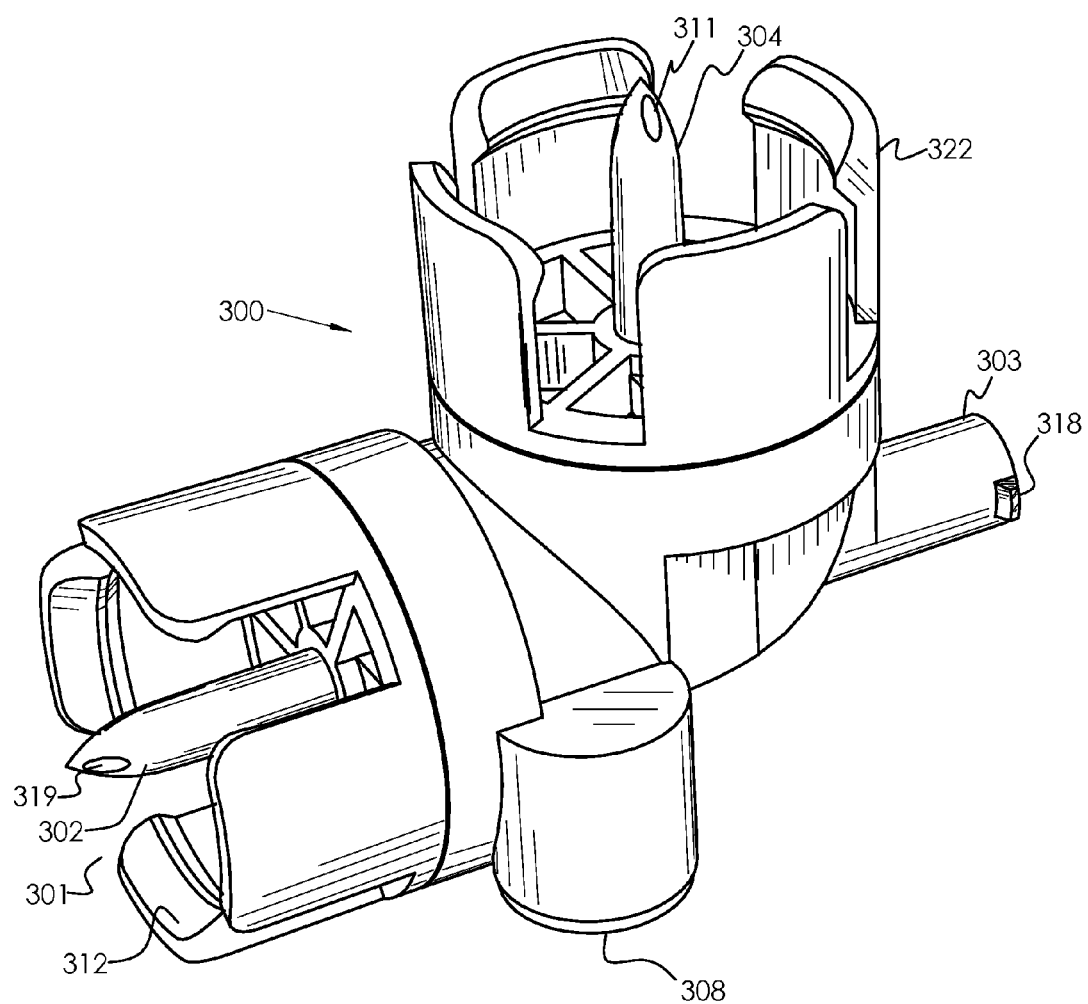
FIG. 11 a perspective view of a fluid transfer device aspect as disclosed and described.
Figures 12A, 12B:
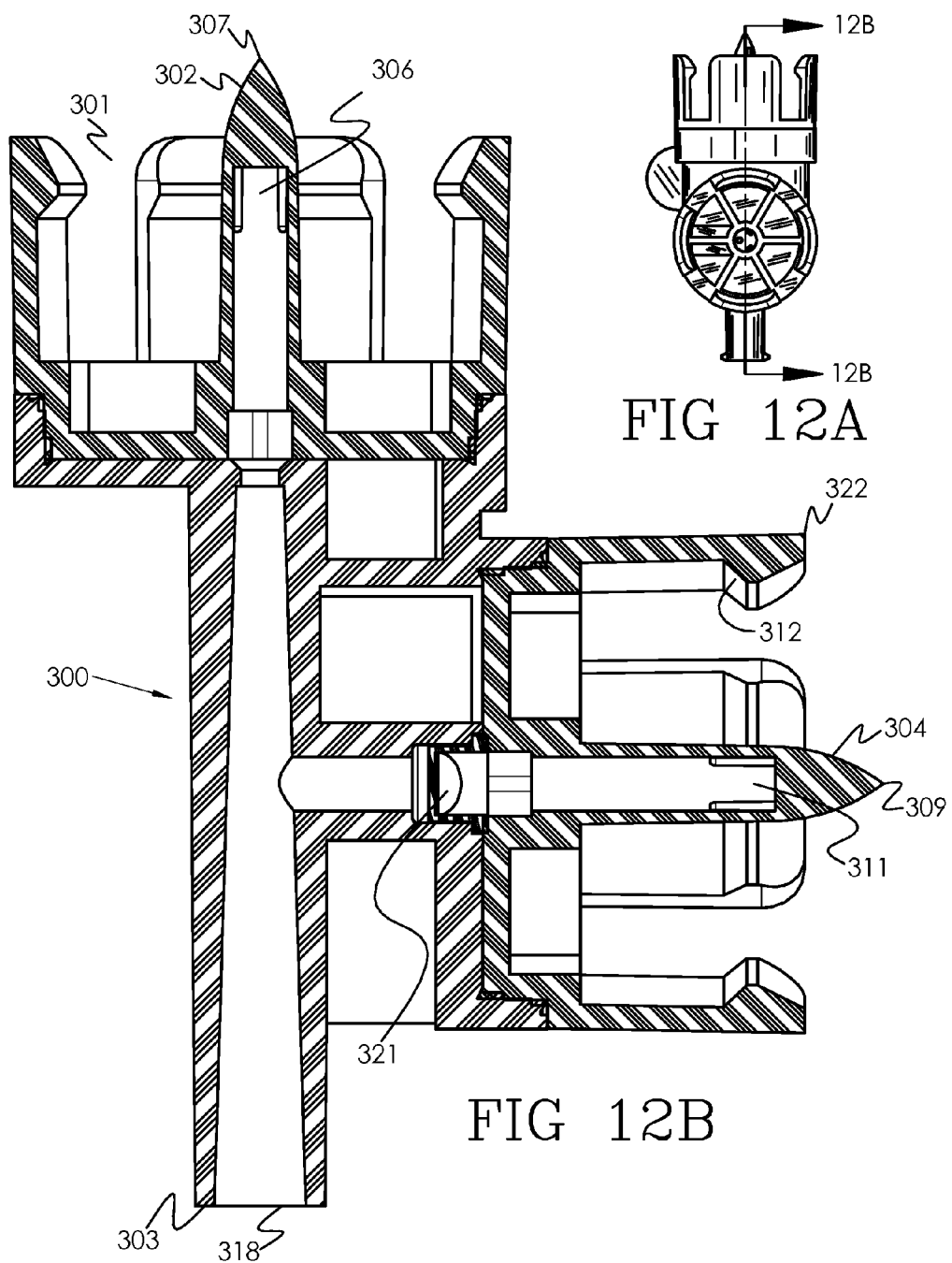
FIGS. 12A & 12B depict a sectional plane and corresponding cross-sectional view, respectively, of the device of FIG. 11.
Figures 13A, 13B:
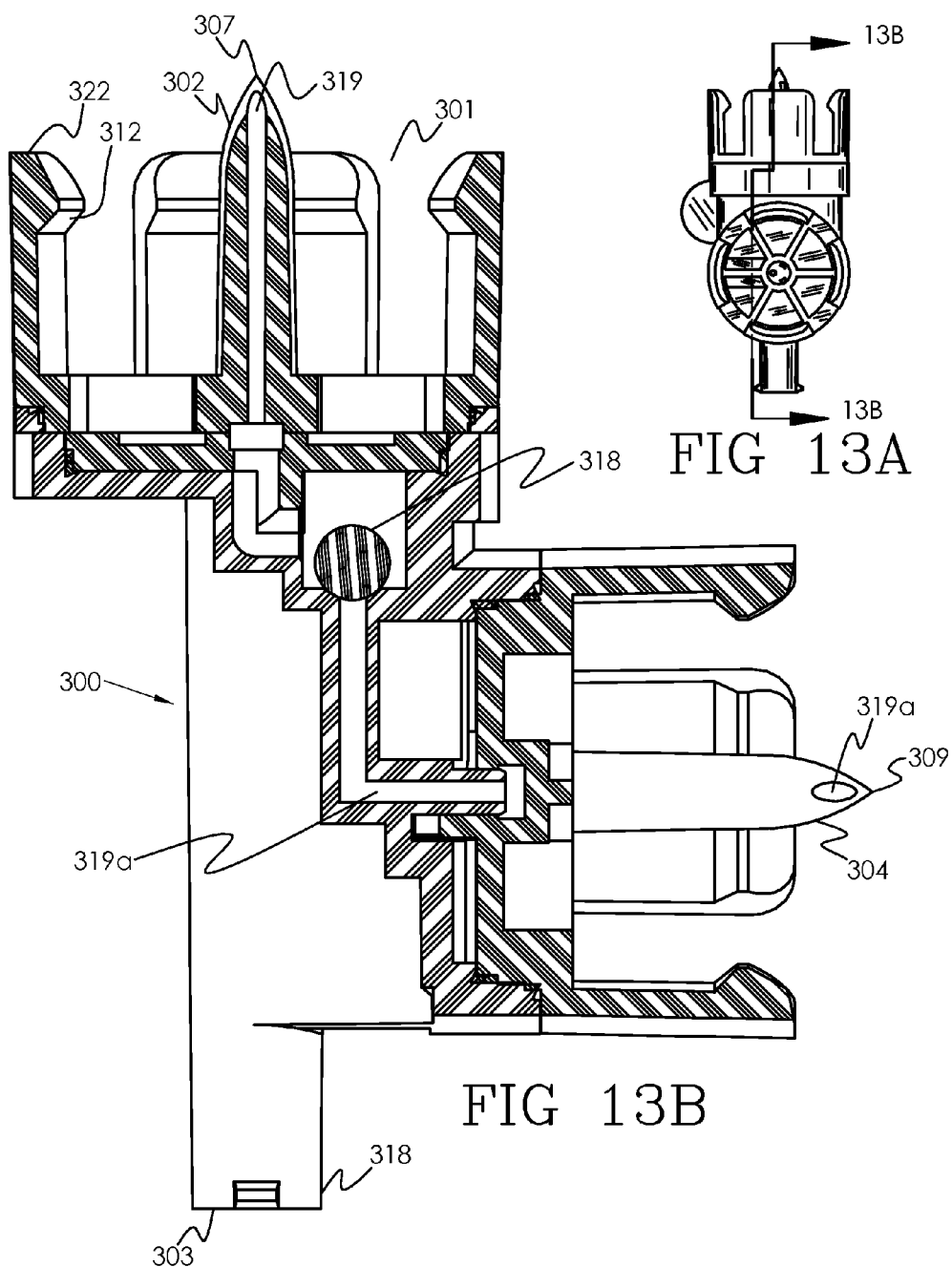
FIGS. 13A & 13B depict a sectional plane and corresponding cross-sectional view, respectively, of the device of FIG. 11.
Figure 14A:
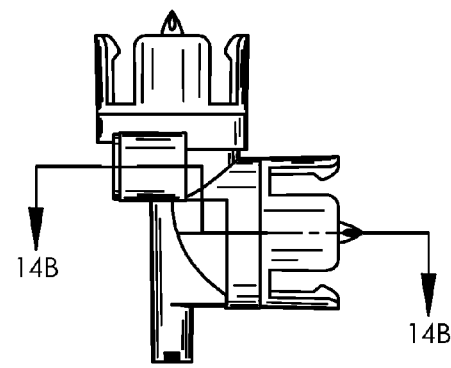
FIGS. 14A & 14B depict a sectional planes and corresponding cross-sectional view, respectively, of the device of FIG. 11.
Figure 14B:
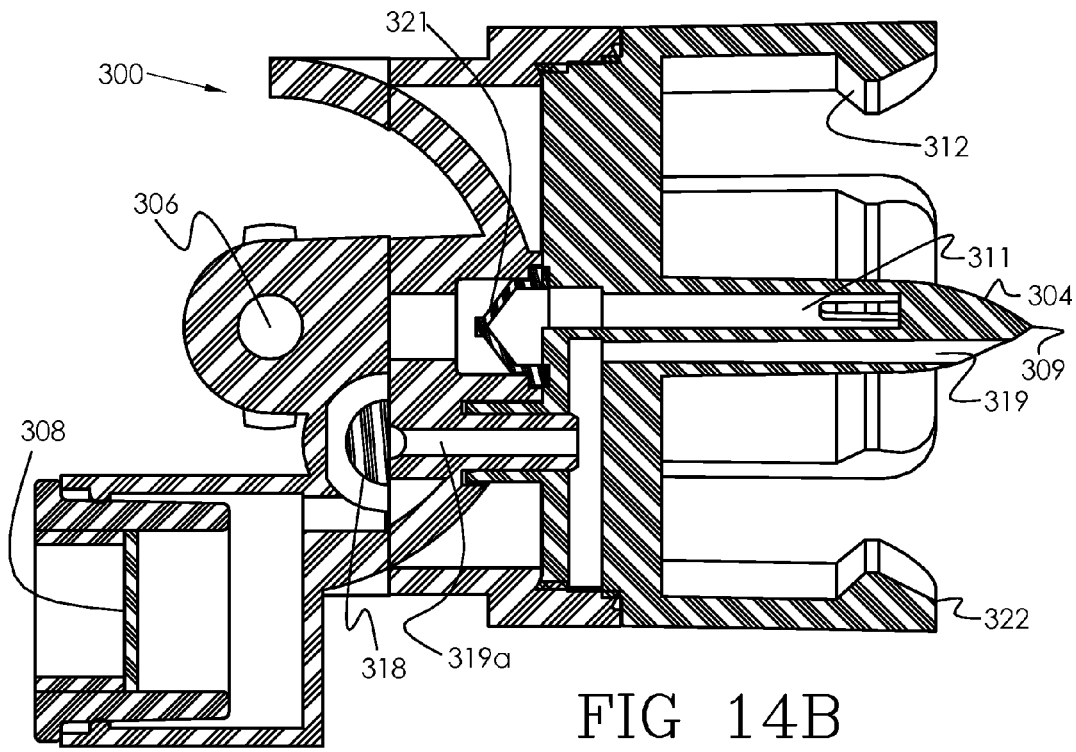

FIG. 11 is a perspective view of fluid transfer device (300). FIGS. 12A, 12B, 13A, 13B, 14A and 14B depict sectional planes and their corresponding cross-sectional views of fluid transfer device (300). Device (300) includes a first piercing assembly (303a) having a first end (303) terminating in fluid communication with connector (318), which may be of the luer-type, locking or non-locking. Second end (301) piercing assembly (301a) terminates in a second end (301) with second piercing member (302). Second piercing member (302) includes second fluid conduit (306) and vent conduit (319) each open proximal to the second piercing member distal end (307). Second fluid conduit (306) is in fluid communication with first fluid conduit (311) of first piercing member (304) and is in fluid communication with the luer connector (318). First fluid conduit (311) is open proximal to the first piercing member distal end (309). First fluid conduit (311) is configured for one-way flow from first piercing member (304) toward second fluid conduit 306 via check valve (321). Vent conduit (319) terminates proximal to the second piercing member distal end and may also be in fluid communication with the ambient surrounding the device via vent (308) with filter element at any point along its path. Vent conduits (319 & 319a) include orientation dependent flow control (318) which may be, but is not limited to, a ball check valve arrangement in which fluid flow is one-way through only one vent conduit at a time, either between the first or second piercing member distal ends and the ambient, in each of the two use orientations. Either or both of the piercing assemblies may have one or a plurality of attachment fingers (322) which may have an attachment means (312) for securing to a container such as a vial or an IV bag.

Figure 15A:
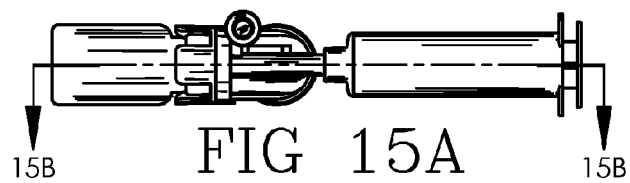
FIGS. 15A & 15B depict a sectional plane and corresponding cross-sectional view, respectively, of an initial use state of the device of FIG. 11.
Figure 15B:
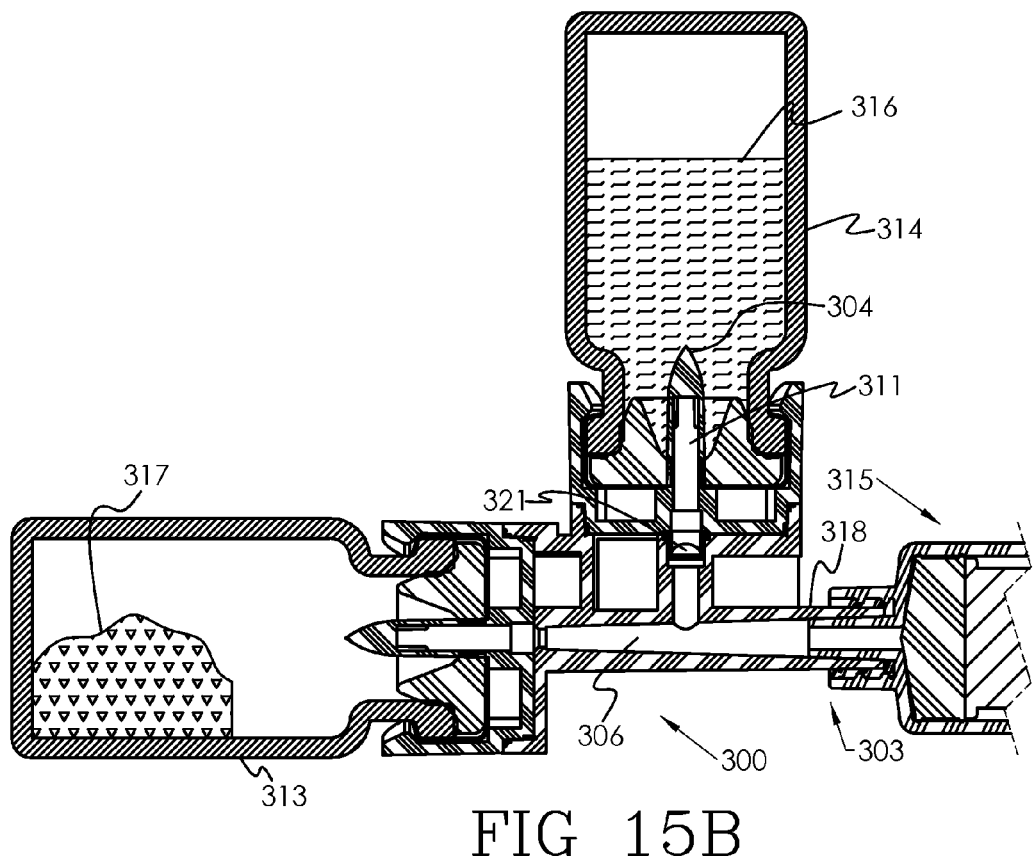
Figures 16A, 16B:
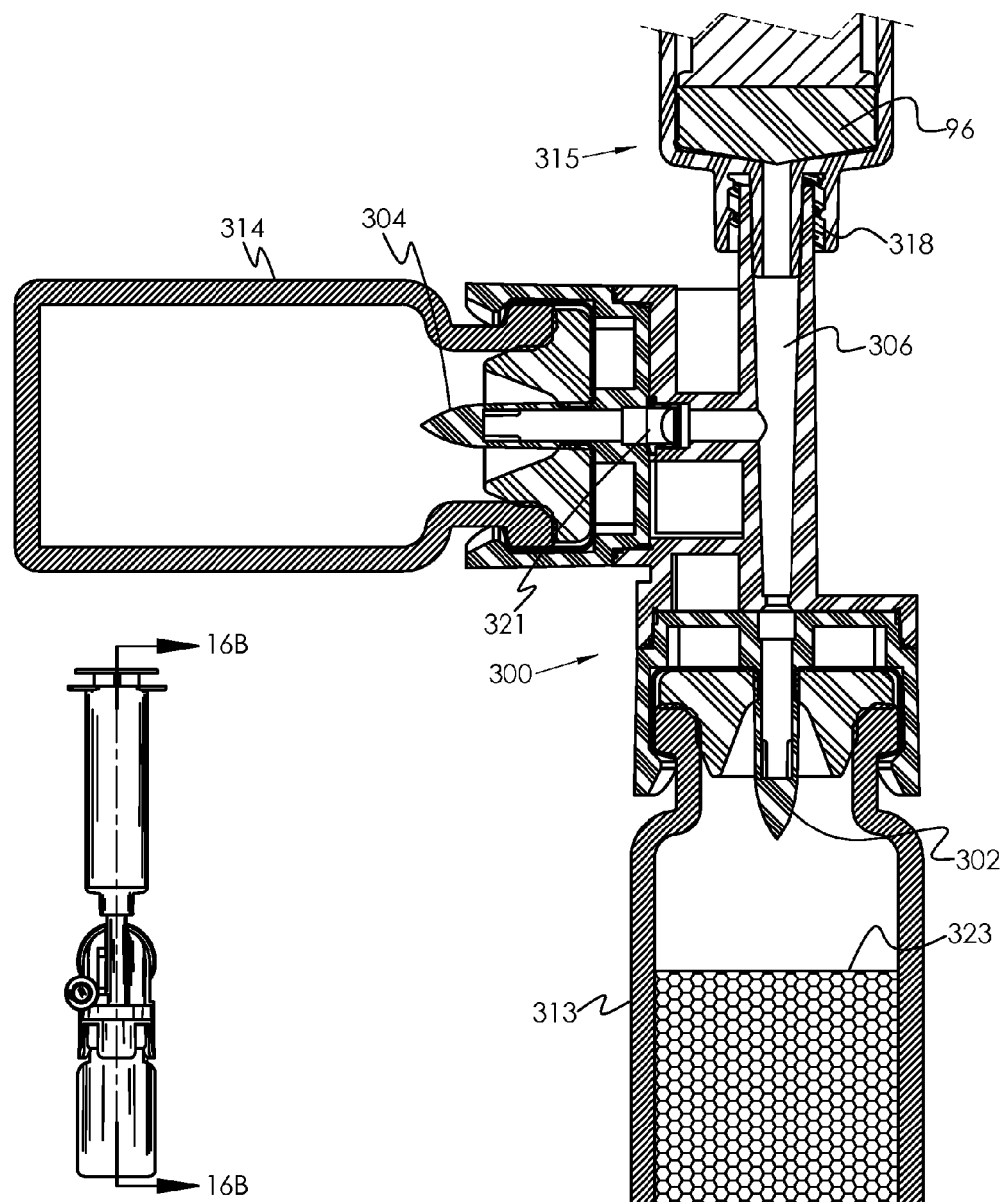
FIGS. 16A & 16B depict a sectional plane and corresponding cross-sectional view, respectively, of an intermediate use state of the device of FIG. 11.
Figures 17A, 17B:
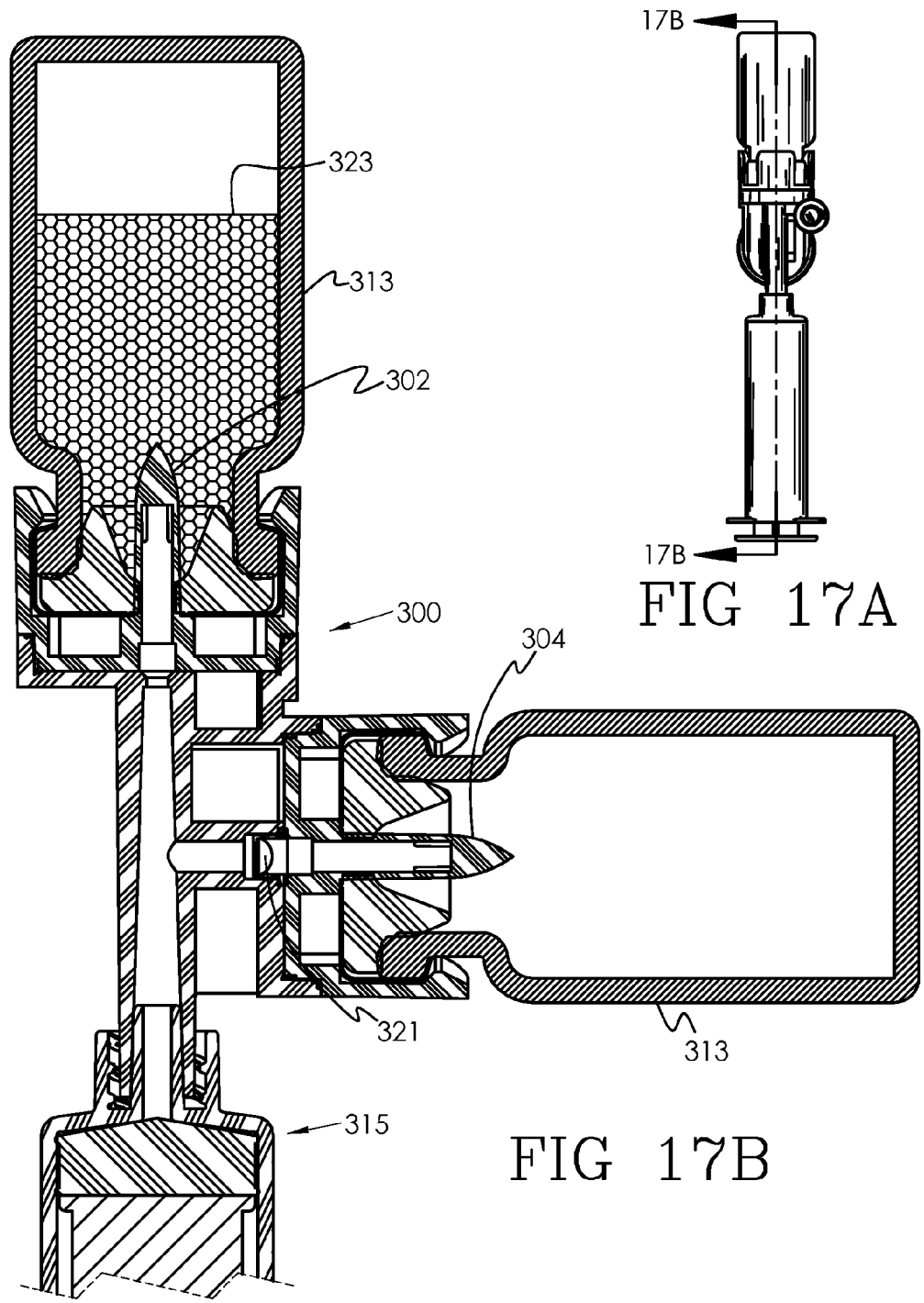
FIGS. 17A & 17B depict a sectional plane and corresponding cross-sectional view, respectively, of a final use state of the device of FIG. 11.
Figure 18:
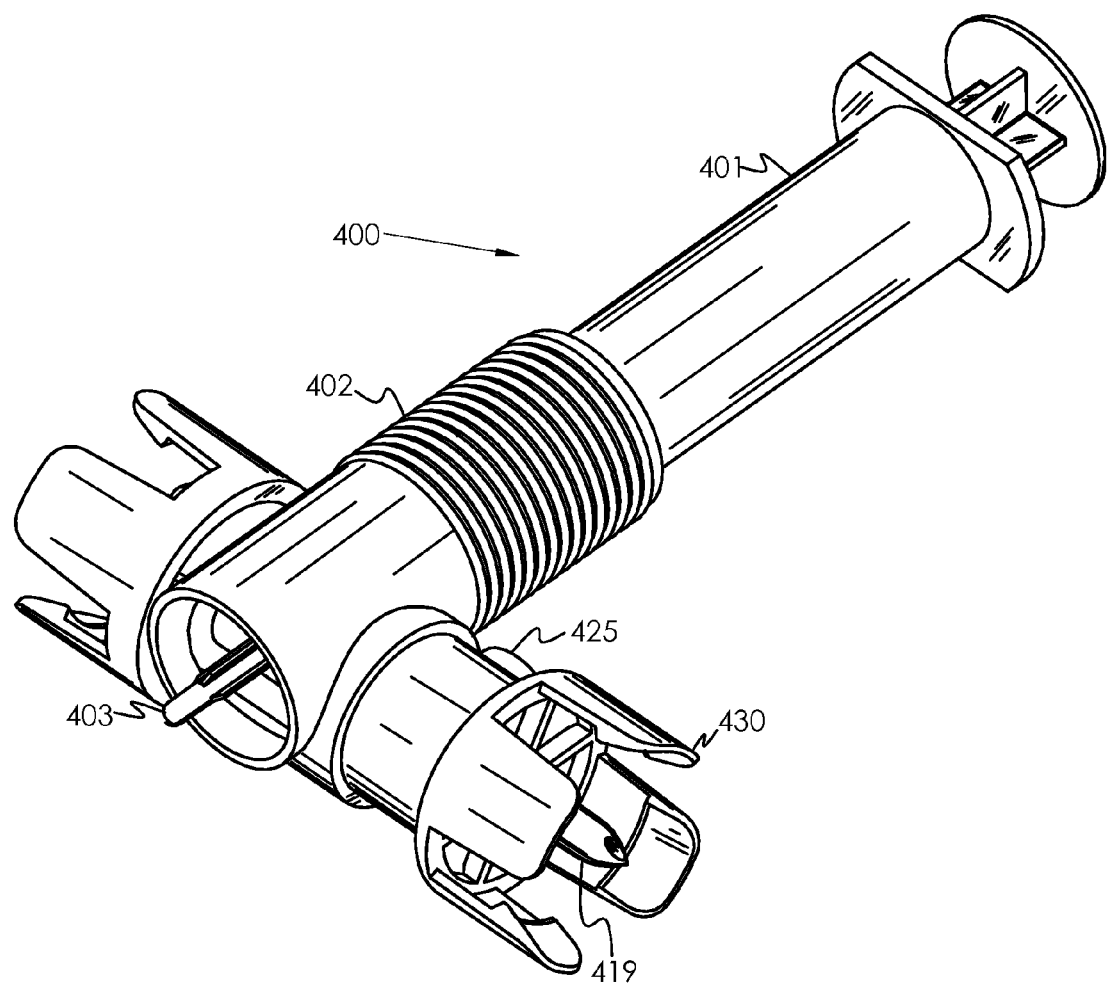
FIG. 18 a perspective view of a fluid transfer device aspect in combination with a fluid delivery device as disclosed and described.

FIG. 15B depicts a cross-sectional view of an initial use state of fluid transfer device (300) shown with first container (314), second container (313) and syringe (315) sealably attached. The first container may contain a fluid (316) which, in this orientation, is proximal to the first end (303) of the device. Second container (314) contains media (317). In use, first and second containers (314 and 313, respectively) are attached to device (300) in an orientation as shown in FIG. 15B together with attached syringe (315) for drawing fluid contents from the first container (314) into the syringe with the vent conduit (319a) of the first piercing member (304) vented to ambient so that pressure may be equalized in the first container. Device (300) is then oriented as in FIGS. 16A and 16B, and the fluid in the syringe may then be introduced into second container (313). When an adequate amount of the fluid has been deposited into the second container, the second media may be mixed with the fluid in a fashion appropriate to the mixture. The device may then be oriented as shown in FIGS. 17A and 17B so that syringe (315) may draw in the mixture. Pressure in the second container (313) is equalized through the vent conduit (319) of the second piercing member (302).

Figure 19:
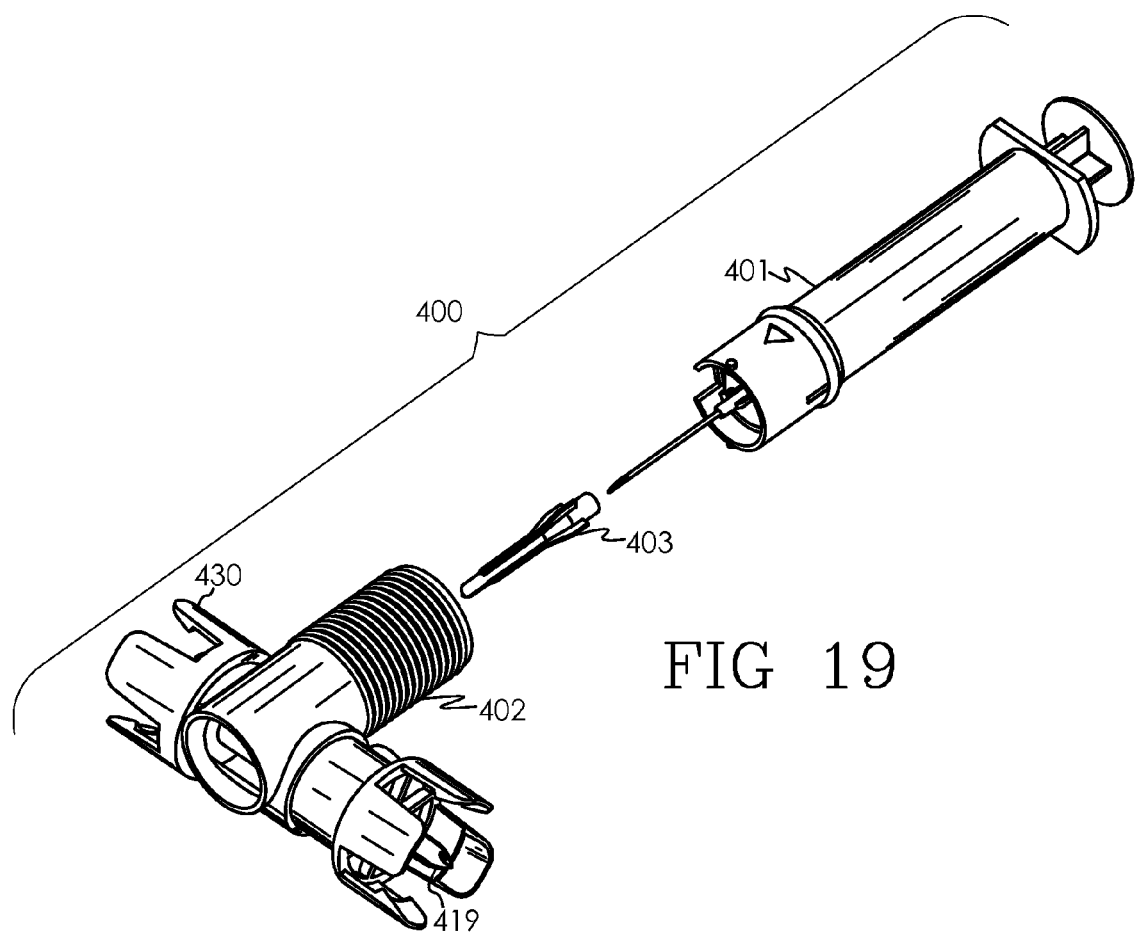
FIG. 19 is an exploded, perspective view of the device of FIG. 18.
Figures 21A, 21B:
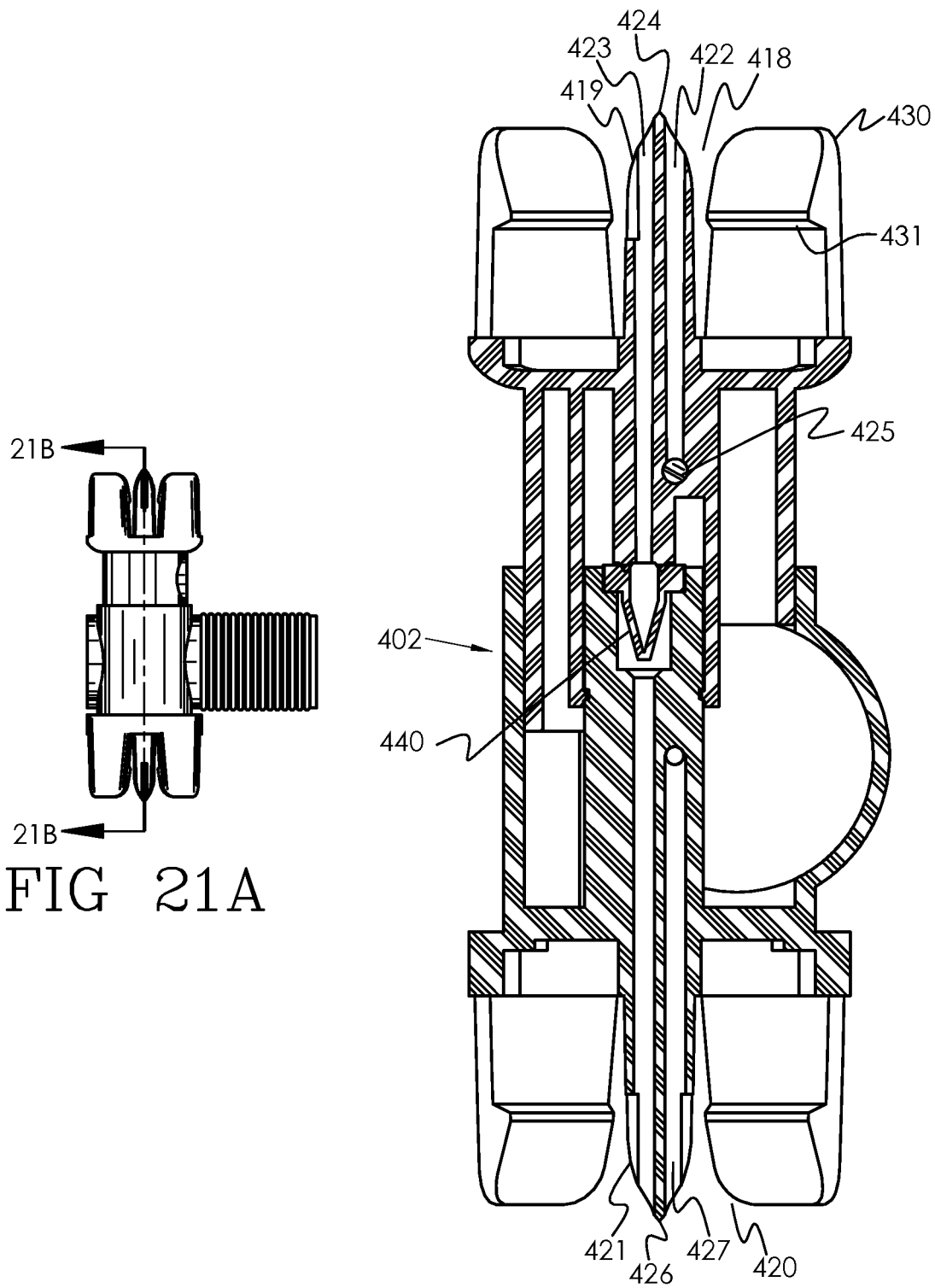
FIGS. 21A & 21B depict a sectional plane and corresponding cross-sectional view, respectively, of the fluid transfer device of the device of FIG. 18.
Figures 22A, 22B:
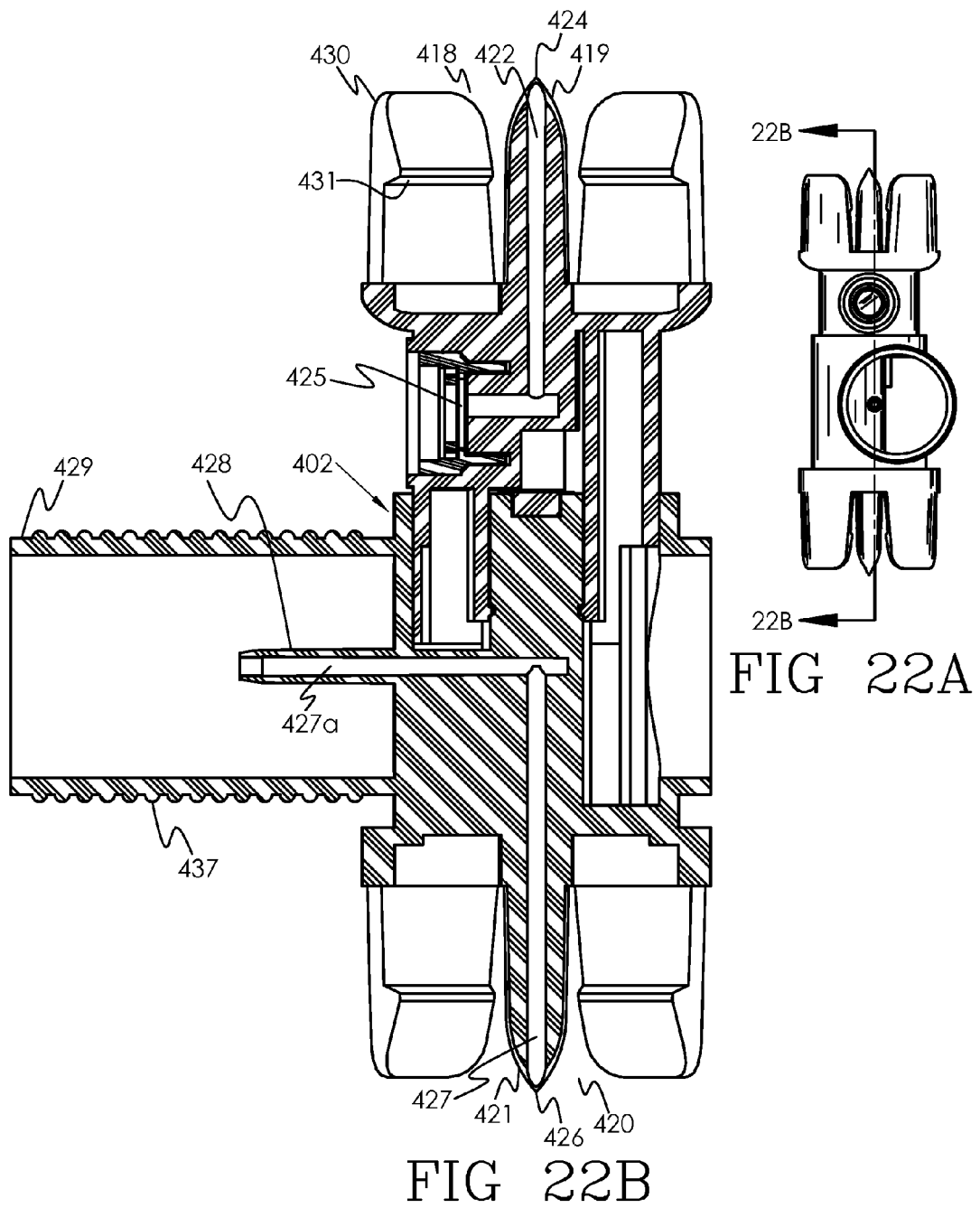
FIGS. 22A & 22B depict a sectional plane and corresponding cross-sectional view, respectively, of the fluid transfer device of FIG. 18.

Referring now to FIGS. 18-26, FIG. 18 is a perspective view of fluid transfer device (400), which is shown with container access element (402) having attached thereto syringe (401) with needle cover (403). FIG. 19 is an exploded, perspective view of fluid transfer device (400). FIGS. 20A and 20B depict a sectional plane and a cross-sectional view, respectively, of syringe (401) comprising an inner fluid containment portion (415), closed first end (405), which may have a plurality of access ways (406) that allow fluid communication between the inner containment portion and the exterior (407) of the syringe. Syringe (401) includes at least one access way proximal end terminating in hollow needle (408), the at least one access way distal end terminating in an elastomeric septum (409). For example, the syringe may have two access ways. The first may be at the syringe end, an elastomeric septum that is normally closed and accessible by a blunt cannula, defined herein as a fluid transfer device connector—upon removal from the container access element (402) and corresponding connector (428), septum (409) reseals closed. The other, may be a syringe's normal access way, that is, the access opening in the syringe, here shown with a needle, but may be an open male luer, luer lock, spray nozzle, and the like. The elastomeric septum may be of any access type which may include, but is not limited to, pre-slit or otherwise piercable type. Syringe (401) includes open second end (410) which may have any number of proximally located retaining features (411), exterior portion (407), which may have protruding flange features (413) located proximal to the second end, and orientation features (414) located proximal to the first end. Sliding member (417) comprising seal rings (416) is cooperatively coupled to actuation means (404) for triggering of a safety mechanism. Needle cover (403) is sealably attached about the hollow needle to prevent leakage.

FIGS. 21A, 21B, 22A and 22B, are sectional planes and their corresponding cross-sectional views of container access element (402) of device (400). Container access element (402) comprises first piercing assembly (418) terminating in first piercing member (419) and second piercing assembly (420) terminating in second piercing member (421). The first piercing member may have at least one vent conduit (422) and at least one fluid conduit (423) each open proximal to the first piercing member distal end (424). The vent conduit(s) may be in fluid communication with vent (425) and may have a filter element (425a) between its opening and the vent. Fluid conduit(s) open proximal to the second piercing member distal end (426) and are configured for one-way fluid communication from first piercing member (419) to second piercing member (421). The second piercing member may also have secondary fluid conduit (427) open proximal to the second piercing member distal end and may terminate in connector (428). Cannula (428) is disposed within receptacle (429) which may sealably accept a syringe; the receptacle may also slidably accept a syringe. Receptacle (429) is shown with gripping means (437). Either or both of the piercing assemblies (418, 420) may have one or a plurality of attachment fingers (430) which may have attachment means (431) for securing to a container such as a vial or an IV bag.

Figure 23A:
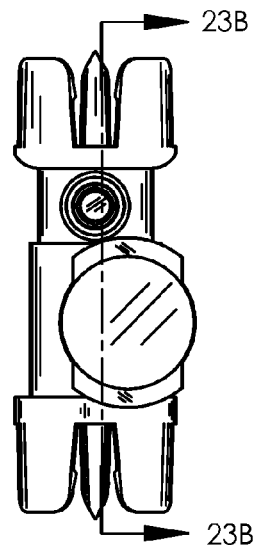
FIGS. 23A & 23B depict a sectional plane and corresponding cross-sectional view, respectively, of the fluid transfer device of FIG. 18 in a pre-bypass state.
Figure 23B:
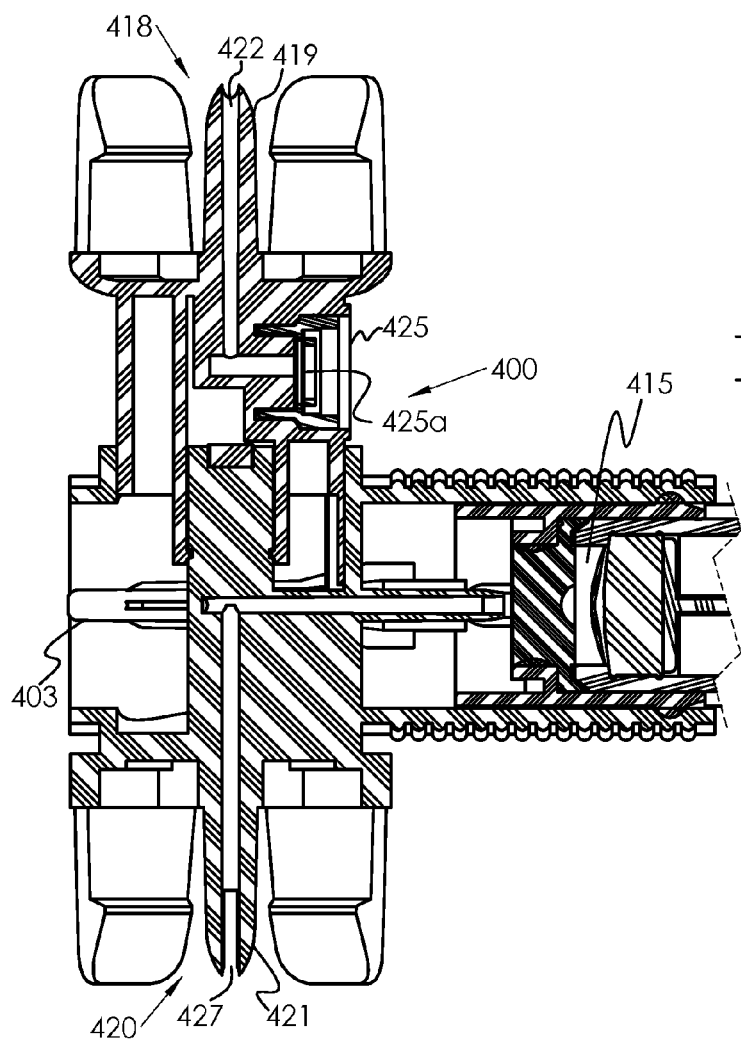

FIGS. 23A and 23B depict a sectional plane and a cross-sectional view, respectively, of fluid transfer device (400) in a pre-bypass state, generally referred to as a state whereby the inner containment portion (415) may be prevented from fluid communication or otherwise receiving fluid.

FIG. 24A and 24B depict a sectional plane and a cross-sectional view, respectively, of fluid transfer device (400) in a bypass access state, generally referred to as a state wherein cannula (428) pierces septum (409) of syringe (401) thus allowing fluid communication between inner containment portion (415) and secondary fluid conduit (427) of container access element (402). The by-pass state is the result of a sliding-coupling arrangement between the syringe and receptacle (429) of the container access element.

Figures 25A, 25B:
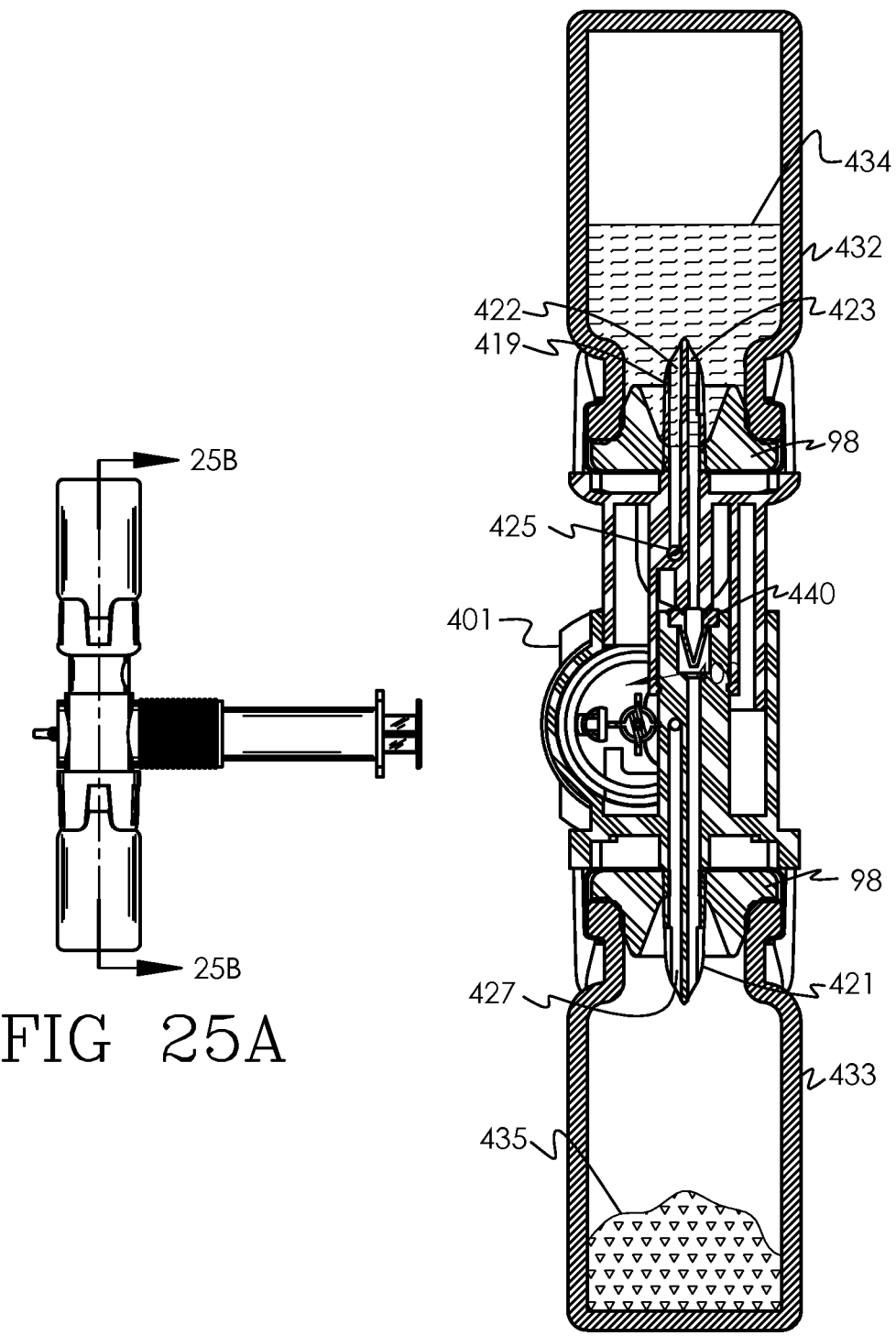
FIGS. 25A & 25B depict a sectional plane and corresponding cross-sectional view, respectively, of an initial use state of the fluid transfer device of FIG. 18 shown with attached containers and a syringe sealably attached.
Figure 26A:
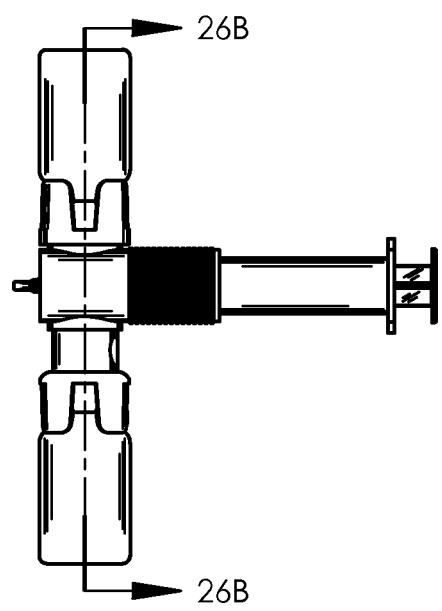
FIGS. 26A & 26B depict a sectional plane and corresponding cross-sectional view, respectively, of an inverted use state of the fluid transfer device of FIG. 18.
Figure 26B:
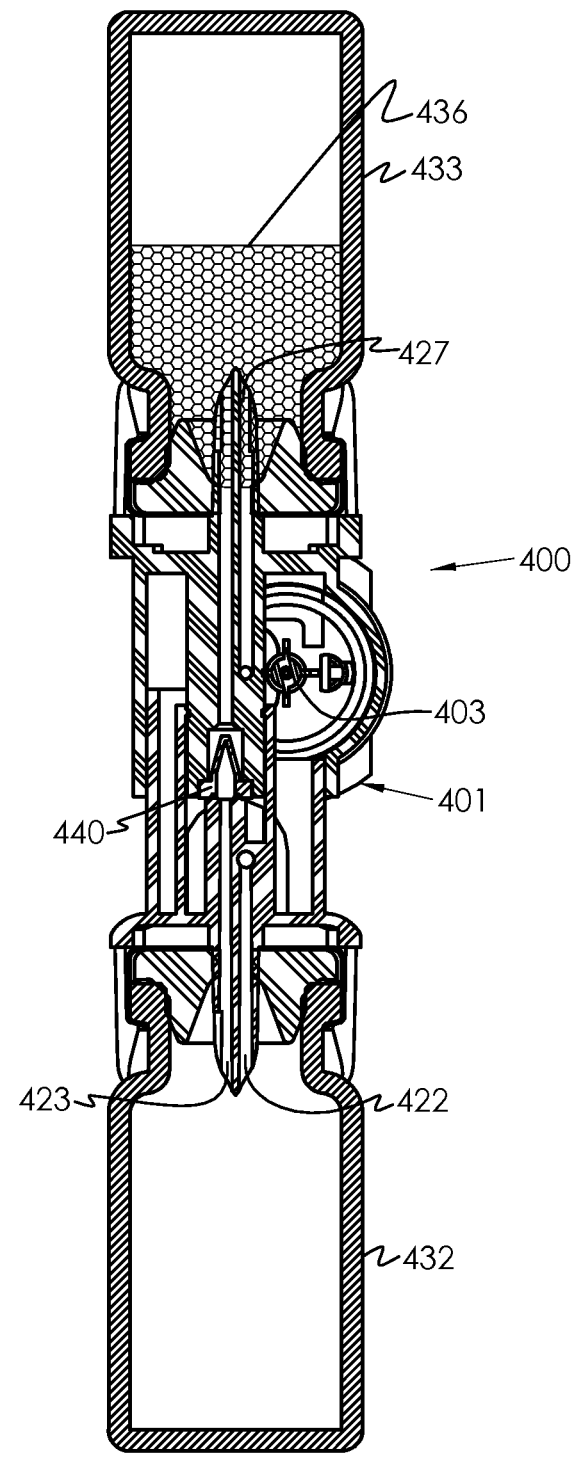

FIGS. 25-26 depict the in-use states of fluid transfer device (400). Thus, FIGS. 25A and 25B depict a sectional plane and a cross-sectional view, respectively, of an initial use state of fluid transfer device (400) shown with first container (432) containing fluid (434) positioned above second container (433) containing media (435) and syringe (401) sealably attached. In use, either a partial vacuum in the second container (433) or the syringe (as described above in FIG. 20B in a bypass state) creates a pressure differential between the first and the second container such that the fluid contained in the first container is urged to fluidically navigate fluid conduit (423) and introduced into the second container through an opening in the second piercing member. During this time air may be vented into the first container such that the pressure in the first container may be equalized. When an adequate amount of the fluid has been deposited into the second container, the second media may be mixed with the fluid in a fashion appropriate to the mixture. The device may then be inverted as shown in FIGS. 26A and 26B, which depict a sectional plane and a cross-sectional view, respectively, of an inverted use state of fluid transfer device (400) shown with first container (432) below second container (433) containing a mixture (436) of the first and the second container contents, and syringe (401) sealably attached in a bypass access state. In this state, the mixture may be drawn into the syringe. Pressure may be equalized in the second container via fluid communication between the vent conduit and the fluid conduit.

Figure 27:
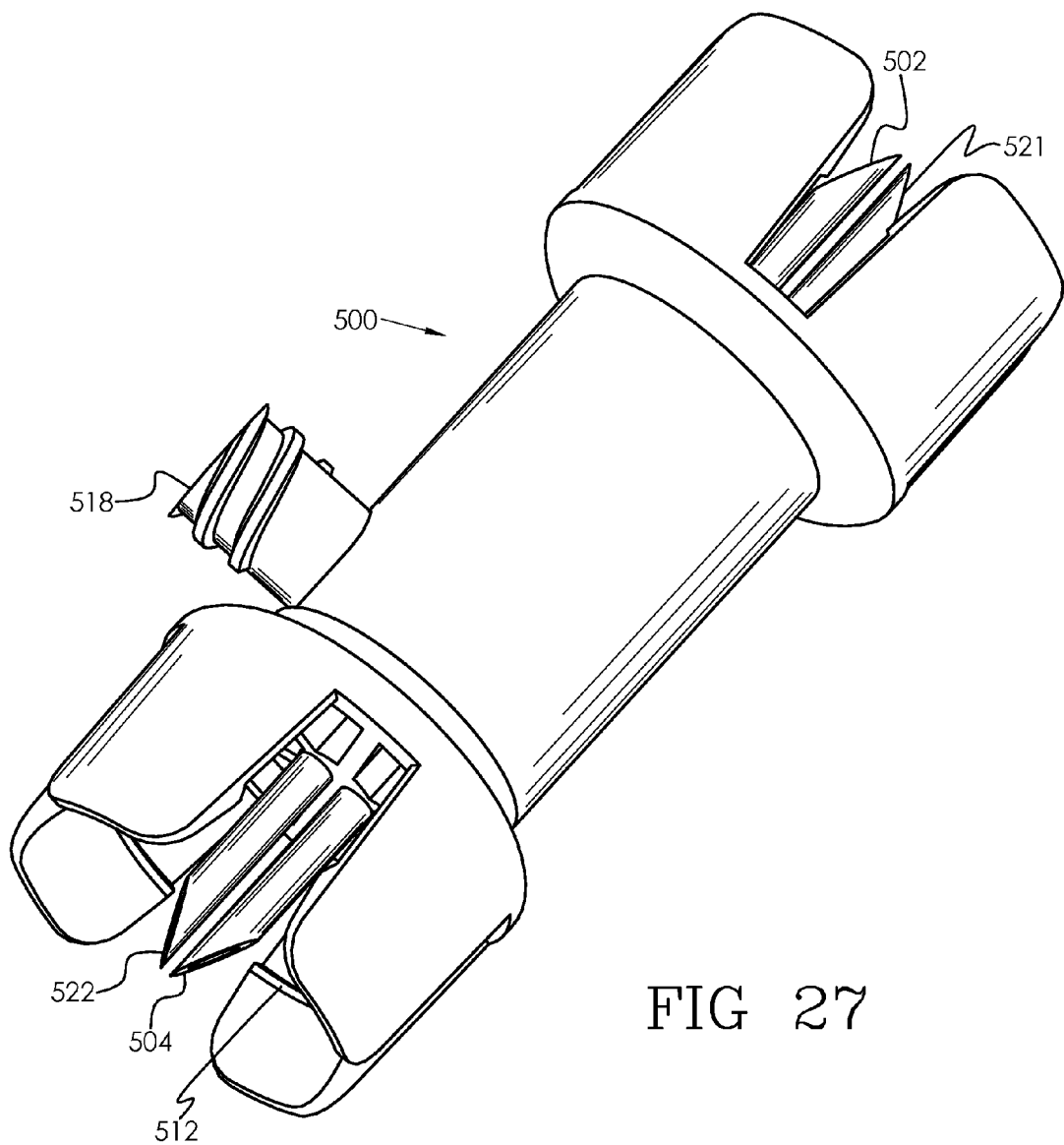
FIG. 27 is a perspective view of a fluid transfer device aspect as disclosed and described.
Figures 29A, 29B:
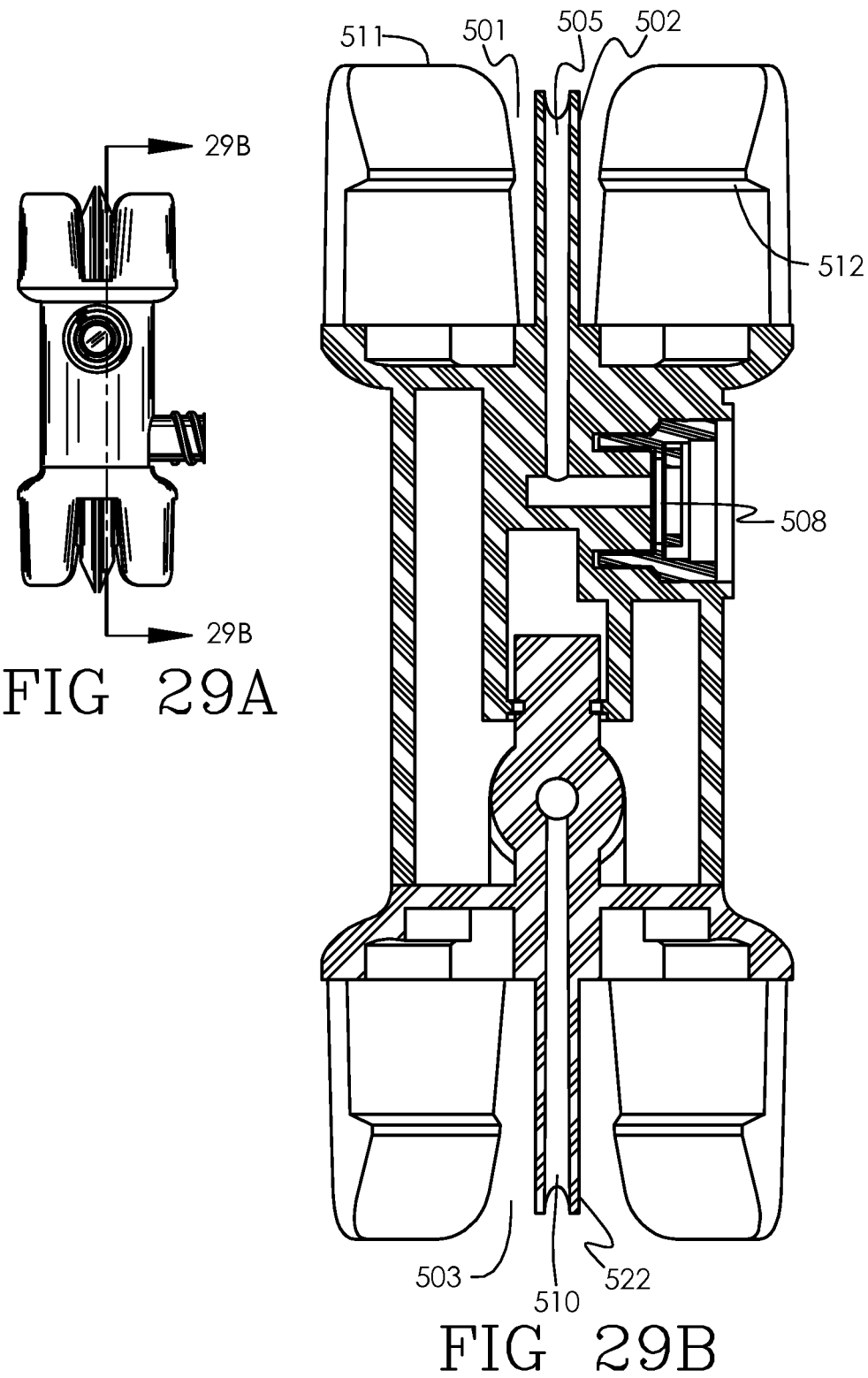
FIGS. 29A & 29B depict a sectional plane and corresponding cross-sectional view, respectively, of the fluid transfer device of FIG. 27.

FIG. 27 depicts a perspective view of fluid transfer device (500) having multiple piercing members at one or both of the piercing assemblies of the device. Such additional piercing members provide one or more of the following attributes and/or benefits: (i) prevent rotation of the container about the device to improve user sense of security; (ii) reduce the overall area of puncture in the septum to minimize amount of displaced elastomer to ease and improve overall safety of insertion; and/or (iii) balance sealing of elastomer septum about the piercing member(s) that may otherwise be oblong or oddly shaped if two or more lumens are contained in a single piercing member. In one aspect, the vent conduits may be contained within their own piercing members for penetrating the septum of a vial or IV bag. Note that multiple piercing members may be applied to all embodiments.

Thus, FIGS. 28A, 28B, 29A and 29B depict sectional planes and their corresponding cross-sectional views of fluid transfer device (500) including a first piercing assembly (501) terminating in a first piercing member (521) and second piercing member (502), and a second piercing assembly (503) terminating in a third piercing member and fourth piercing members (522). The first piercing assembly may include vent conduit (505) in fluid communication with vent (508) with filter element and fluid opening proximal to the second piercing member distal end (507). The first piercing assembly has fluid conduit (506), providing one-way fluid communication from conduit (506), open at first piercing member distal end (524), to conduit (504) of the second piercing assembly, open proximal to third piercing member distal end (509), via, for example, by check valve (520). Fourth piercing member (522) comprises a secondary fluid conduit (510) opening proximal to the fourth piercing member distal end (523) terminating at connector (518). Either or both of the piercing assemblies (501, 503) may have one or a plurality of attachment fingers (511) which may have attachment means (512) proximal to the attachment finger distal end for securing to a container such as a vial or IV bag.

Figure 30A:
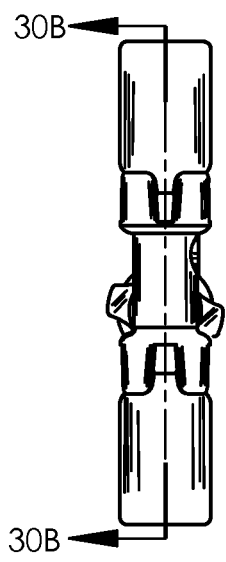
FIGS. 30A & 30B depict a sectional plane and corresponding cross-sectional view, respectively, of an initial use state of the fluid transfer device of FIG. 27.
Figure 30B:
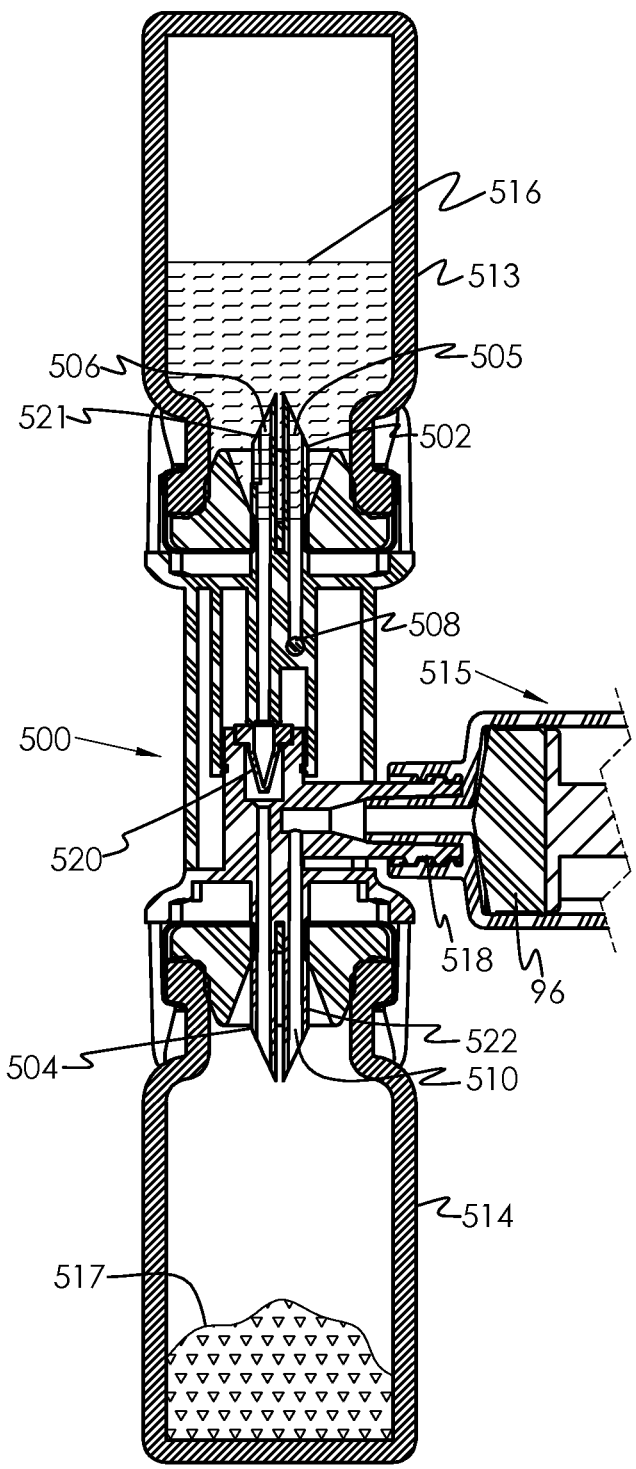

FIGS. 30-31 depict the method of use of fluid transfer device (500), which follows essentially as described above for FIGS. 4B and 5B. Thus, FIGS. 30A and 30B depict a cross-sectional view of an initial use state of fluid transfer device (500) shown with first container (513) containing fluid (516) inverted above second container (514) containing second media (517) and syringe (515) sealably attached. FIGS. 31A and 31B show a sectional plane and a cross-sectional view of an intermediate use state of fluid transfer device (500), shown with the second container (514) containing mixture (519) of the first and second container contents inverted above first container (513) and a syringe (515) sealably attached.

Figure 32:
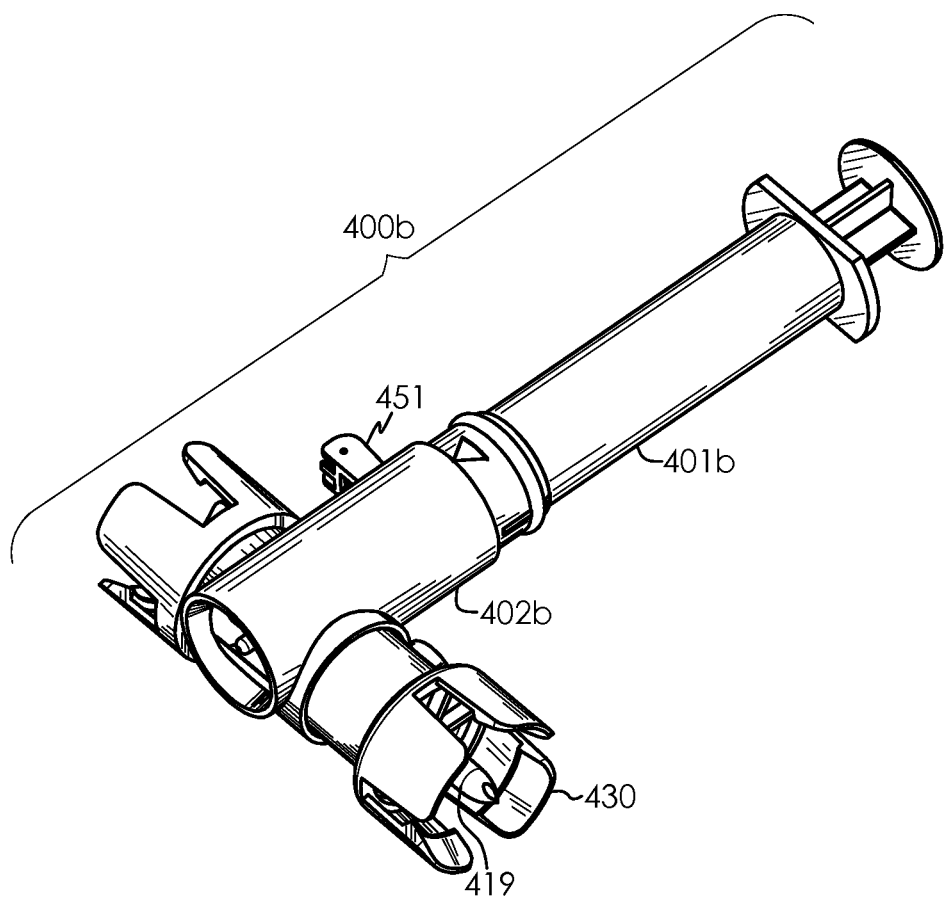
FIG. 32 is a perspective view of a fluid transfer device aspect as disclosed and described and a fluid delivery device reversibly attached.
Figure 33:
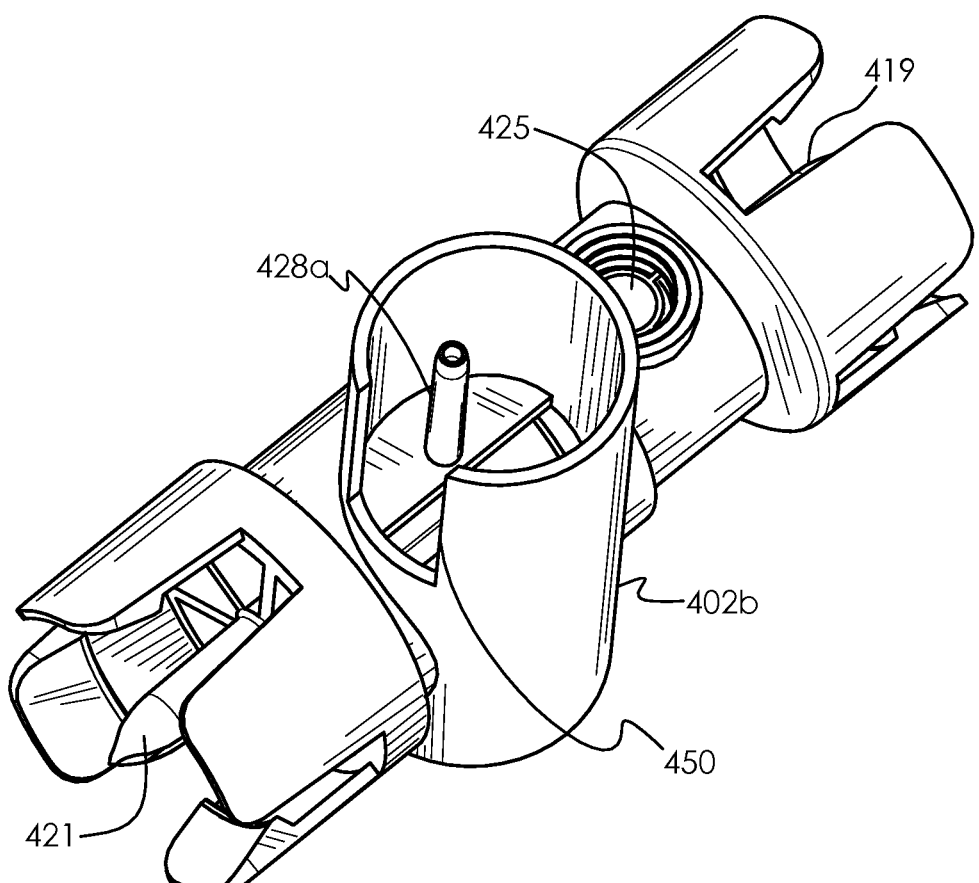
FIG. 33 is a perspective view of the fluid transfer device of FIG. 32.
Figure 34A:
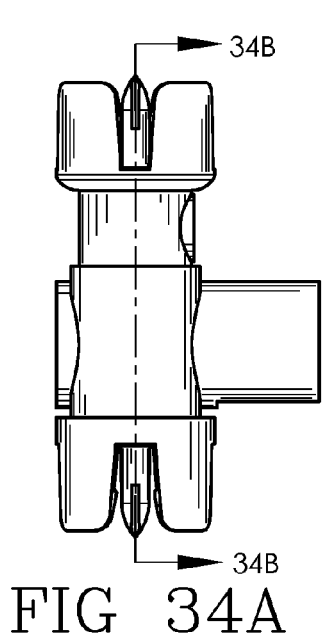
FIGS. 34A & 34B depict a sectional plane and corresponding cross-sectional view, respectively, of the fluid transfer device of FIG. 33.
Figure 34B:
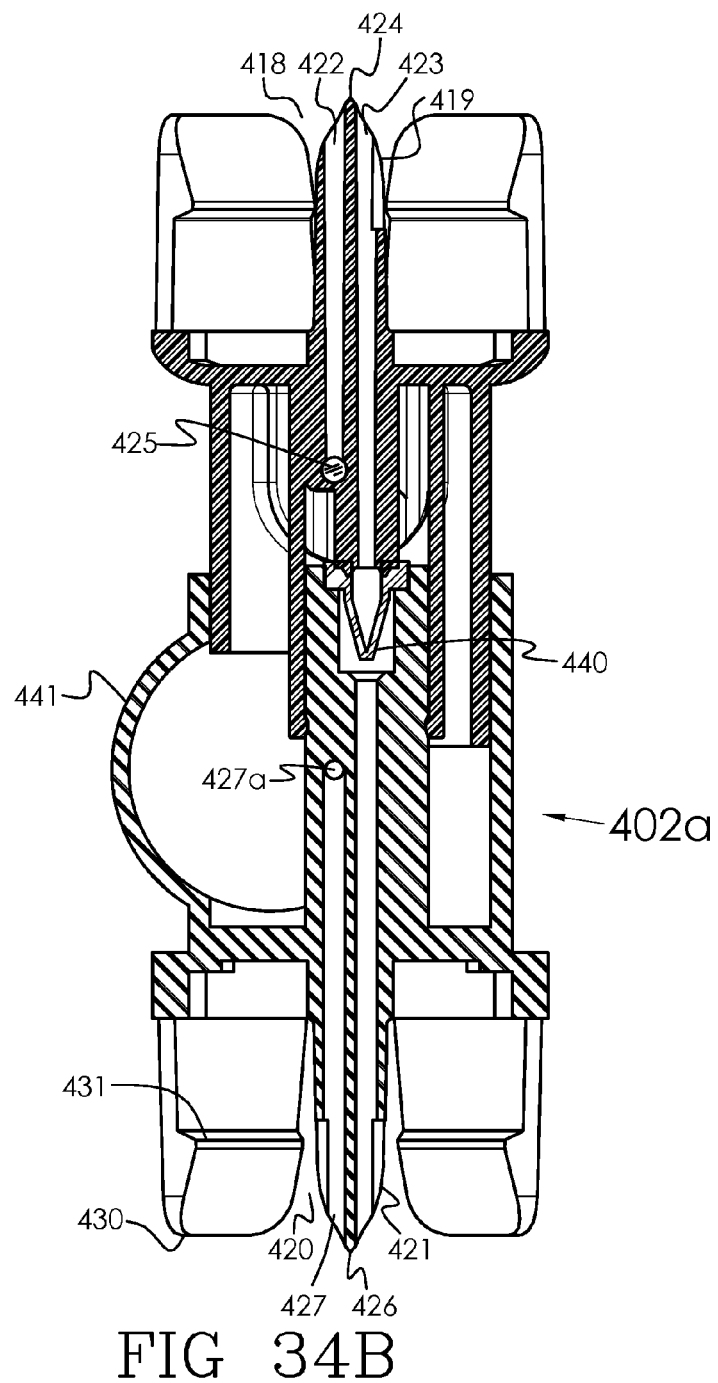
Figures 35A, 35B:
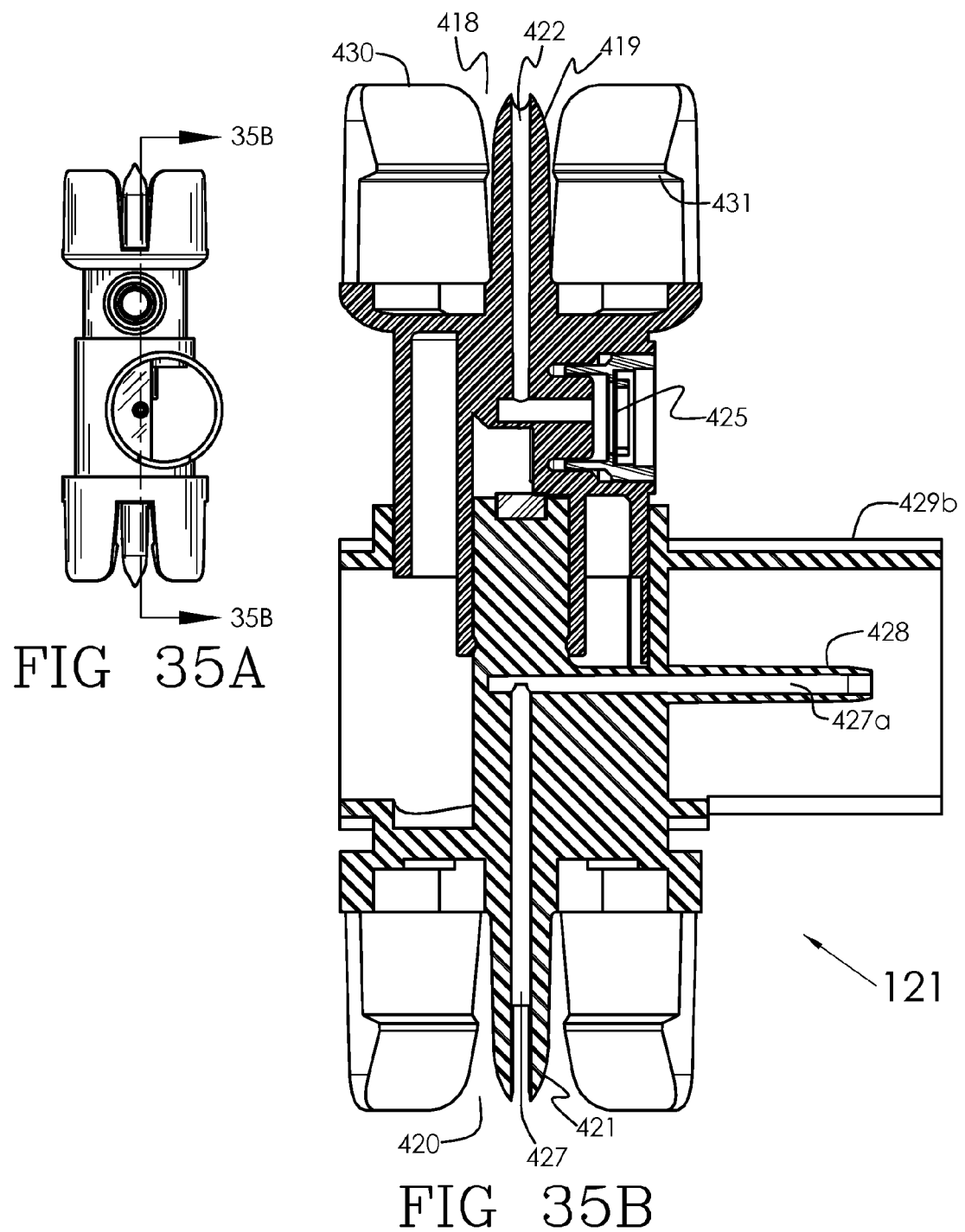
FIGS. 35A & 35B depict a sectional plane and corresponding cross-sectional view, respectively, of the fluid transfer device of FIG. 33.

FIG. 32 is a perspective view of a fluid transfer device (400b) having similar features of that of previously described device (400) of FIGS. 18-26, with the difference being that container access element (402b) includes accommodation (450) for syringe safety mechanism (451) of syringe (401b). Thus, FIGS. 33, 34A, 34B, 35A and 35B, are a perspective view of container access element (402b) and sectional planes and corresponding cross-sectional views for a fluid transfer device (400b) with method of use equivalent to that of device (400). Thus, container access element (402b) includes first piercing assembly (418) terminating in a first piercing member (419) and second piercing assembly (420) terminating in second piercing member (421). The first piercing member vent conduit (422) and fluid conduit (423) each open proximal to the first piercing member distal end (424), the vent conduit(s) in fluid communication with the ambient surrounding the device via vent (425), which may have a filter element. The fluid conduit(s) open proximal to the second piercing member distal end (426) and provide one-way fluid communication from the first piercing member to the second piercing member via a check valve (440). The second piercing member includes secondary fluid conduit (427), open proximal to the second piercing member distal end, terminating in cannula (428) which may be pointed or blunted at its distal end. The cannula may be disposed within receptacle (429b) for receiving a syringe. The receptacle may have features for positionally locating or orienting the syringe therewithin. Either or both of the piercing assemblies (418, 420) may have one or a plurality of attachment fingers (430) which may have attachment means (431) proximal to the attachment finger distal end for securing to a container such as a vial or IV bag.

Figure 36:
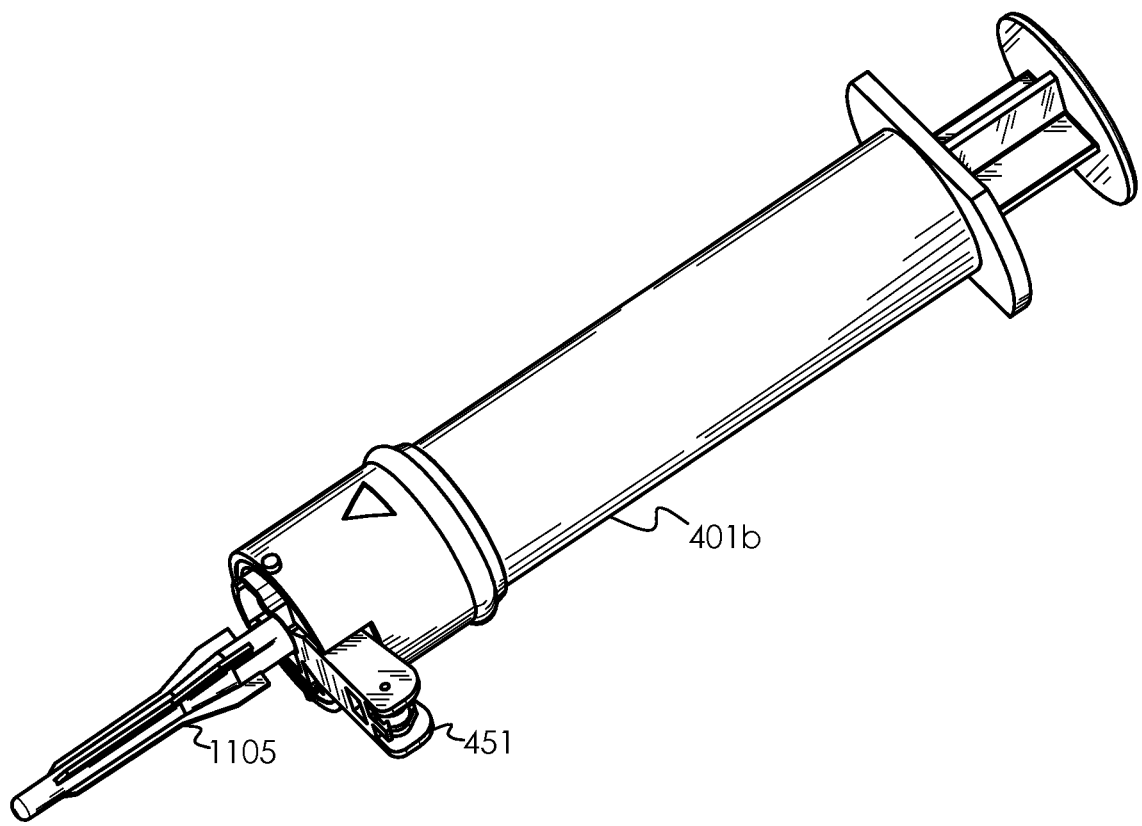
FIG. 36 is a perspective view of a syringe with a safety mechanism.
Figure 37A:
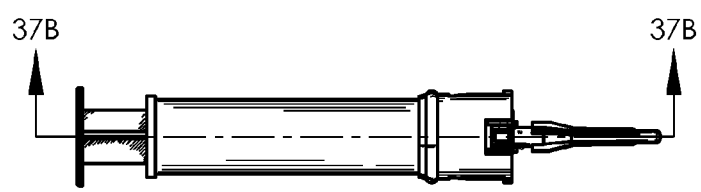
FIGS. 37A & 37B depict a sectional plane and corresponding cross-sectional view, respectively, of the syringe of FIG. 36.
Figure 37B:
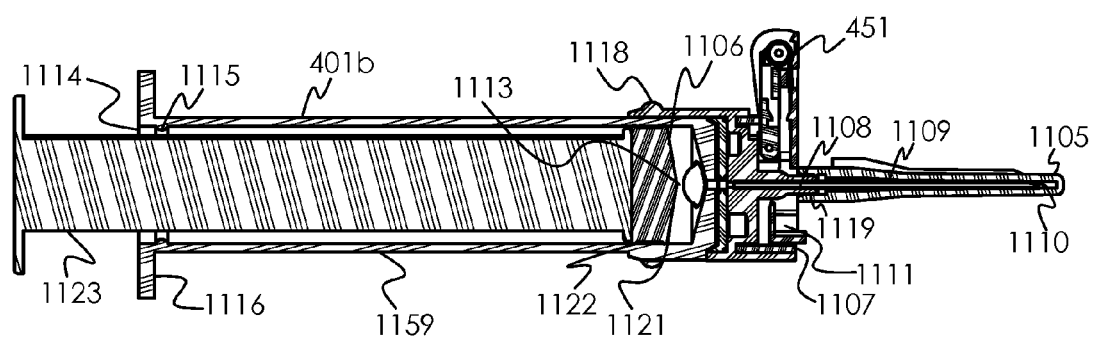
Figure 38A:
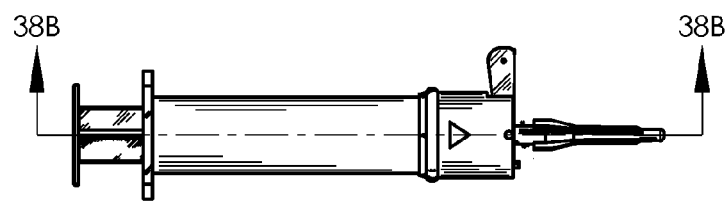
FIGS. 38A & 38B depict a sectional plane and corresponding cross-sectional view, respectively, of the syringe of FIG. 36.
Figure 38B:
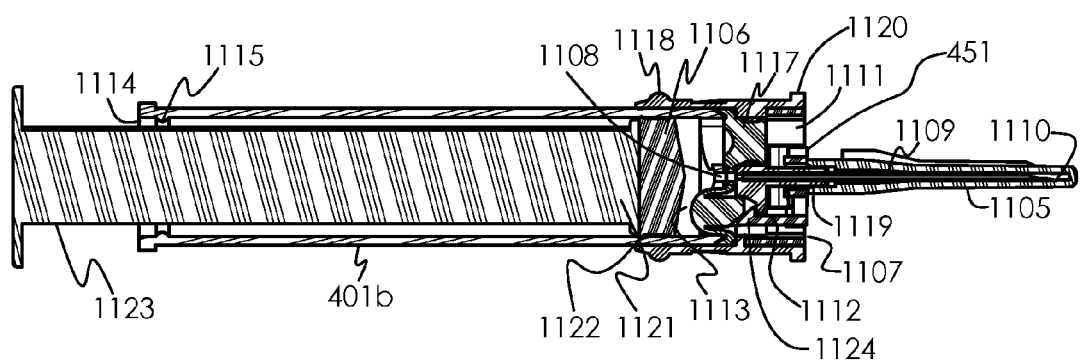

FIGS. 36-38 refer to safety syringe 401b adapted for the devices (400, 400b). Thus, FIGS. 37A, 37B, 38A and 38B include a perspective view and sectional plane and corresponding cross-sectional views of syringe 401b, including needle cover (1105) and needle-stick safety mechanism (451). Syringe (401b) comprises inner containment portion (1106), closed first end (1107) having at least one proximally located conduit (1108) from the inner containment portion such that it may be in fluid communication with pointed distal end (1110) of hollow needle portion (1109), the closed first end of which may also have an inner portion (1111) which may act as a receptacle for a needle-stick safety device. The closed first end provides a latching shelf (1112) for state control and coupling of the needle-stick safety mechanism. The closed first end comprises a deformable portion (1113), open second end (1114), which may have any number of proximally located retaining features (1115), exterior portion (1159), which may have protruding flange features (1116) located proximal to the second end. Piercable septum portion (1117) is proximal to the first end allowing for fluid communication with the inner containment portion when pierced. Closed first end also comprise hub portion (1119) for a sealable connection with a needle cover. External portion comprises orientation features (1120) located proximal to the first end. Syringe also comprises an elastomeric, sliding seal member (1121) comprising any number of seal rings joined to actuation means (1123). FIGS. 38A and 38B shows latch (1124) of needle-stick safety mechanism in its collapsed state coupled with latching shelf (1112).

Use of the fluid transfer device 400b is achieved by the procedures disclosed herein as follows. A safety syringe may be seated within the mating receptacle located on the container access element such that a cannula of the container access element pierces the septum portion providing fluid communication with the inner containment portion of the syringe. The syringe is used to create a pressure differential between the first and second containers or the second container has a predetermined partial vacuum such that the fluid contained in the first container is urged to fluidically navigate a fluid conduit of the first piercing member and be introduced into the second container through an opening in the second piercing member. During this time air may be vented into the first container such that the pressure in the first container may be equalized. When an adequate amount of the fluid has been deposited into the second container, the second media may be mixed with the fluid in a fashion appropriate to the mixture. The device may then be inverted and the mixture may be drawn into the syringe. Pressure may be equalized in the second container via fluid communication between the vent conduit and the fluid conduit. The syringe may then be disconnected from the container access element and be used to dispense the contents thereof. At the end of the delivery stroke, the needle-safety mechanism deploys to cover the tip of the syringe needle tip and some portion of the needle length.

Fluid Control—Fluid Transfer Devices

In at least one exemplary configuration as disclosed in the foregoing figures, a user-actuated plunger is employed to control or otherwise meter fluid between or from the containers accessed by the device. In one aspect, a user-actuated plunger is arranged between the two piercing assemblies. The user-actuated plunger with at least one flow channel may be slidably mounted in the housing and may be linearly displaced with respect to the piercing assemblies and/or the housing such that, in a first position, a flow connection is established between the first piercing member and a lateral opening of the housing or a connector coupled with the housing, and, in a second position, a flow connection is established between the second piercing assembly and a lateral opening of the housing or a connector coupled with the housing In one aspect, the user-actuated plunger is generally cylindrical, and about its circumference, at least one flow channel extends over at least a part of the circumference, but not completely around the perimeter of the plunger. In another aspect, at least one fluid channel of predetermined widths runs the entire circumference of the user-actuated plunger. In another aspect, the at least one flow channel may run essentially straight through the plunger. Other configurations of flow channeling may be used. In at least one predetermined position of linear displacement of the user-actuated plunger in the device housing, the plunger connects various flow channels of the device to one another. For production and assembly reasons, it may be desirable for the user-actuated plunger to be designed as a rotationally symmetrical part.

The user-actuated plunger may be comprised, at least in part, of elastic material, at least in a partial area, in particular a thermoplastic elastomer, or curable elastomer such as a silicone rubber, or synthetic rubber, preferably a non-latex containing rubber. The whole user-actuated plunger may be made of two-component, such as a plastic and an elastic material. In other aspects, the user-actuated plunger may be preferably made of a thermoplastic having a partial area of an elastic material. The design of the user-actuated plunger as a component which is elastic at least in a partial area affords the particular advantage that the elastic partial areas may provide a fluid-tight seal such that leakages of the transfer device are effectively avoided, as well as minimize any residual fluid in the device upon transfer.

Locking means acting between the user-actuated plunger and the housing may be employed and may be positioned relative to the user-actuated plunger and a predetermined position of displacement. This may provide that the user-actuated plunger is not accidentally moved into a predetermined position of displacement until required or intended by the user.

Figure 39:
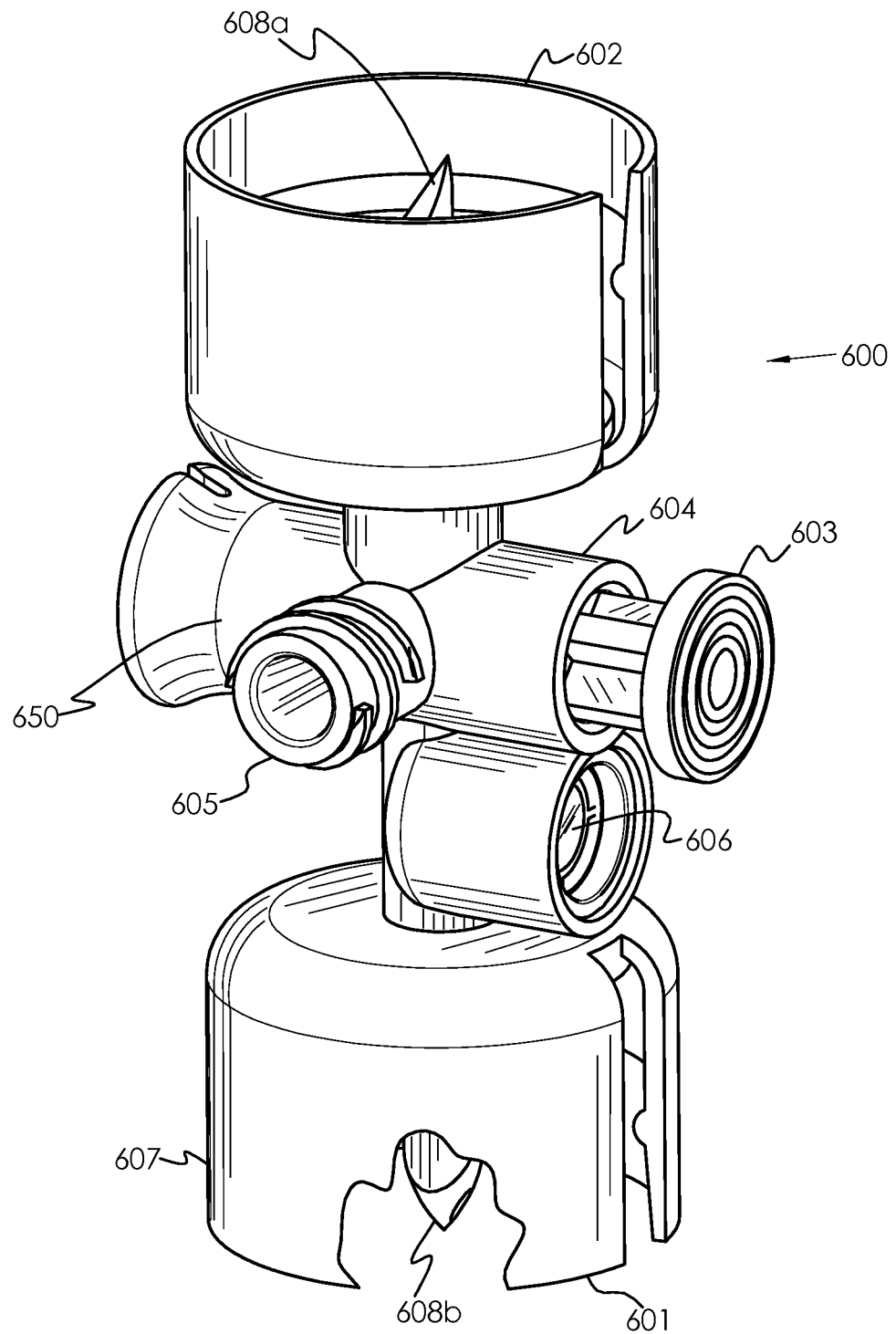
FIG. 39 is a perspective view of a fluid transfer device aspect as disclosed and described.

FIG. 39 is a perspective view of fluid transfer device 600 including fluid control means. The device comprises piercing assemblies (601, 602) for accessing a fluid container and for accessing a media container, respectively. User-actuated plunger (603) is positioned in housing opening (604). Connector (605) defines a fluid opening in the housing and fluidly connects to a fluid delivery device (e.g. syringe) or may be capped to remain closed. Vent (606) with optional filter is disposed between the first and second ends of the device housing (650). Piercing assemblies (601, 602) may each comprises a skirt (607) for attaching to a vial or IV bag connecting port, each skirt including at least one slit (612, 614) surrounding piercing members (608b, 608a) disposed therein, the skirt being of a predetermined perimeter and of a predetermined length projecting distally away from the housing with the opening extending substantially the length of the skirt. Skirts (607, 613) include wholly or partially annular rings (618, 617) of any cross-sectional geometry about its interior for securing the container.

Figures 40A, 40B:
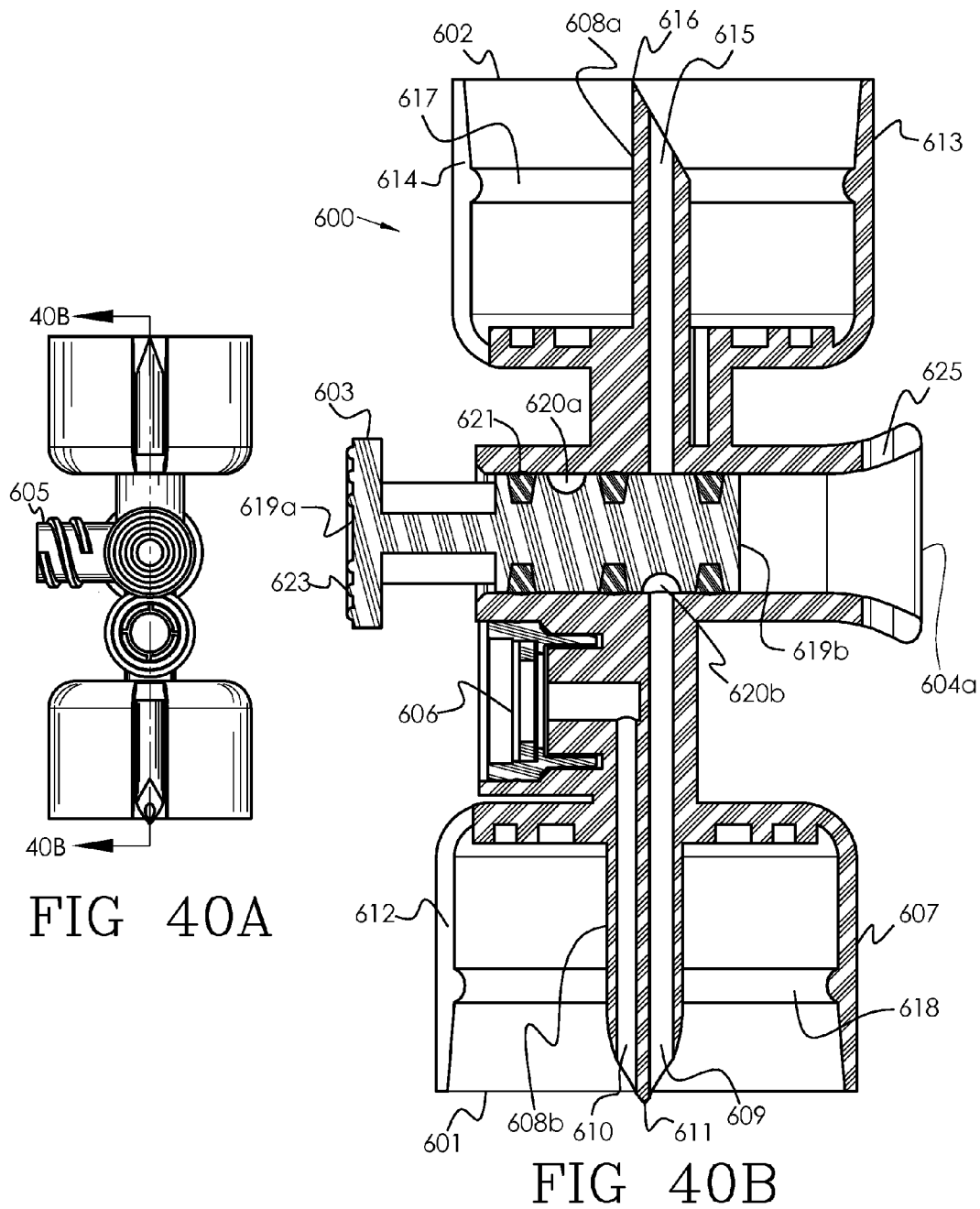
FIGS. 40A & 40B depict a sectional plane and corresponding cross-sectional view, respectively, of the device of FIG. 39.

FIGS. 40A & 40B are section plane and cross-sectional views of the device of FIG. 39, respectively. Piercing member (608b) includes fluid conduit (609), vent conduit (610) and piercing member tip (611). Additional conduits may be incorporated in the piercing member. Vent (606) provides fluid communication with the ambient surrounding the device and may include a filter at any point along its conduit. User-actuated plunger (603) having first end (619a) and second end (619b) is slidably received in housing opening (604) and transverses between a predetermined first position controlling fluid communication between fluid conduit (609) and connector (605) and a predetermined second position controlling fluid communication between fluid conduit (615) and connector (605). Fluid channels (620b, 620a) are provided on the perimeter of the plunger. Each of the fluid channels may be isolated between sealing portions (621) positioned between plunger ends (619a, 619b) for isolating the flow channels with respect to their positions. In one aspect, a third flow channel may be provided about or through the plunger for direct fluid communication between the containers as described in more detail below. First plunger end (619a) includes actuator (623) for one-handed operation. Second plunger end (619b) may also have an actuator for two-finger, reversible sliding of the plunger within housing openings (604, 604a). The actuator includes optional gripping means (623). Housing opening (604a) may have at least one vent cutout (625) for relieving pressure build-up from plunger actuation, if opening (604a) is closed at the second end of the plunger. Connector (605) may be disposed between the piercing assemblies, and may include locking or capping means and/or threads for sealably connecting to the fluid delivery device, such as a syringe.

FIGS. 41A & 41B depicts a first embodiment fluid transfer device (600) in a initial use state with user-actuated plunger (603) positioned in a first predetermined position with device first piercing assembly (601) secured to first container (626) containing a first media (629) such as a fluid, device second piercing assembly (602) secured to second media container (627) containing a second media (630), such as a solid, and syringe (628) secured to connector (605). In this configuration, user-actuated plunger is positioned such that flow channel (620b) provides fluid communication between the syringe and the first container. In one aspect, the flow channel can only provide fluid communication between the syringe and the first container. In this configuration, fluid (629) may be drawn into syringe (628) for transfer.

Now referring to FIGS. 42A & 42B, fluid from the first container is transferred to the syringe by creating a negative pressure with the syringe such that metered dosing of a predetermined amount of fluid from the first media container is provided. Optionally, during use the first container may be vented via vent conduit (610) for precise fluid metering. In this configuration, device (600) is in an intermediate use state with user-actuated plunger (603) positioned in a second predetermined position, such that fluid channel (620a) provides fluid communication between the connector (605) and second media container (627).

Figure 43A:
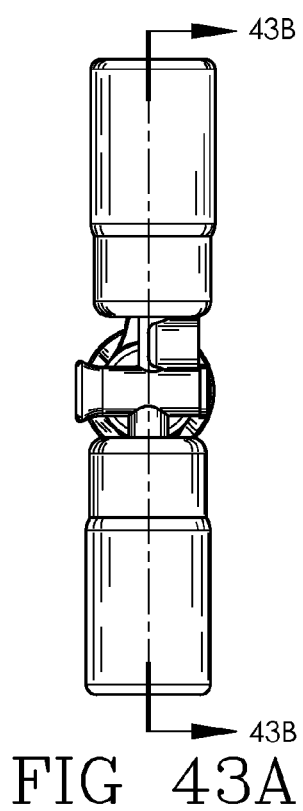
FIGS. 43A & 43B depict a sectional plane and corresponding cross-sectional view, respectively, of the device of FIG. 39 in a second position with fluid transfer from the fluid delivery device to a second container.
Figure 43B:
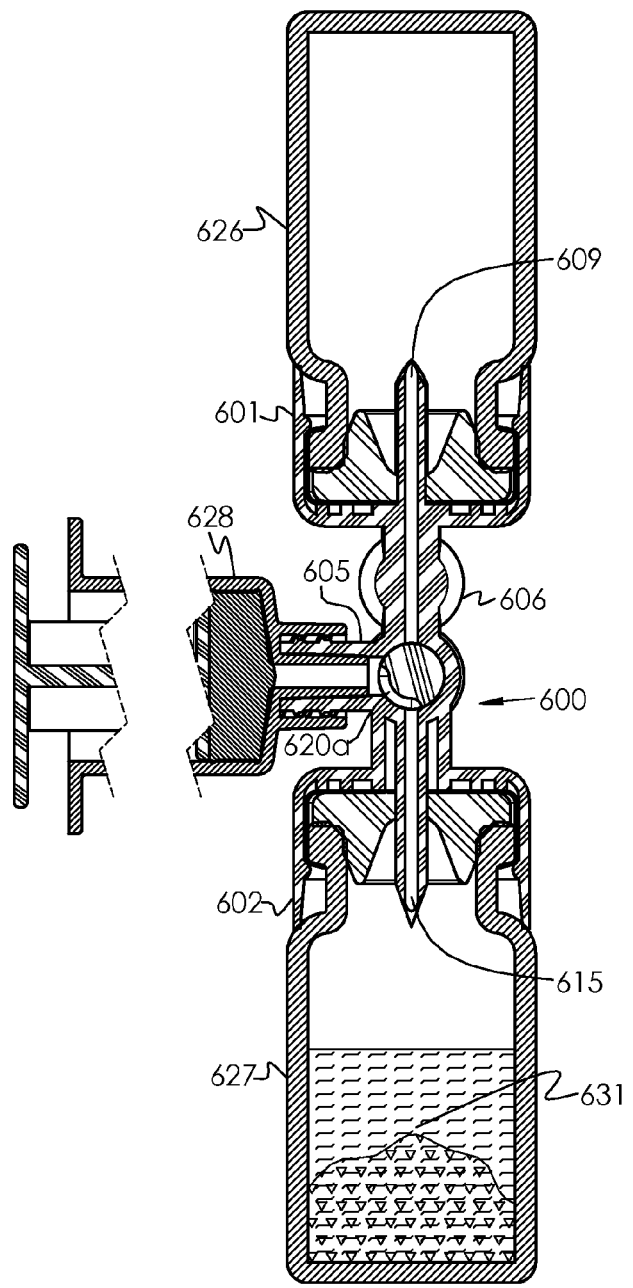

In FIGS. 43A & 43B, the fluid transfer device (600) is shown with fluid (629) from syringe (628) introduced into the second container (627) providing a mixture (631) accessible by syringe (628) secured to connector (605).

FIGS. 44A & 44B depicts fluid transfer device (600) in a final use state with device second piercing assembly (602) inverted with respect to FIGS. 43A & 43B, with user-actuated plunger (603) still positioned in the second predetermined position such that the mixture may be transferred from the second container (627) through the connector (605). Metered dosing of a predetermined amount of mixture (631) is provided.

Figure 45:
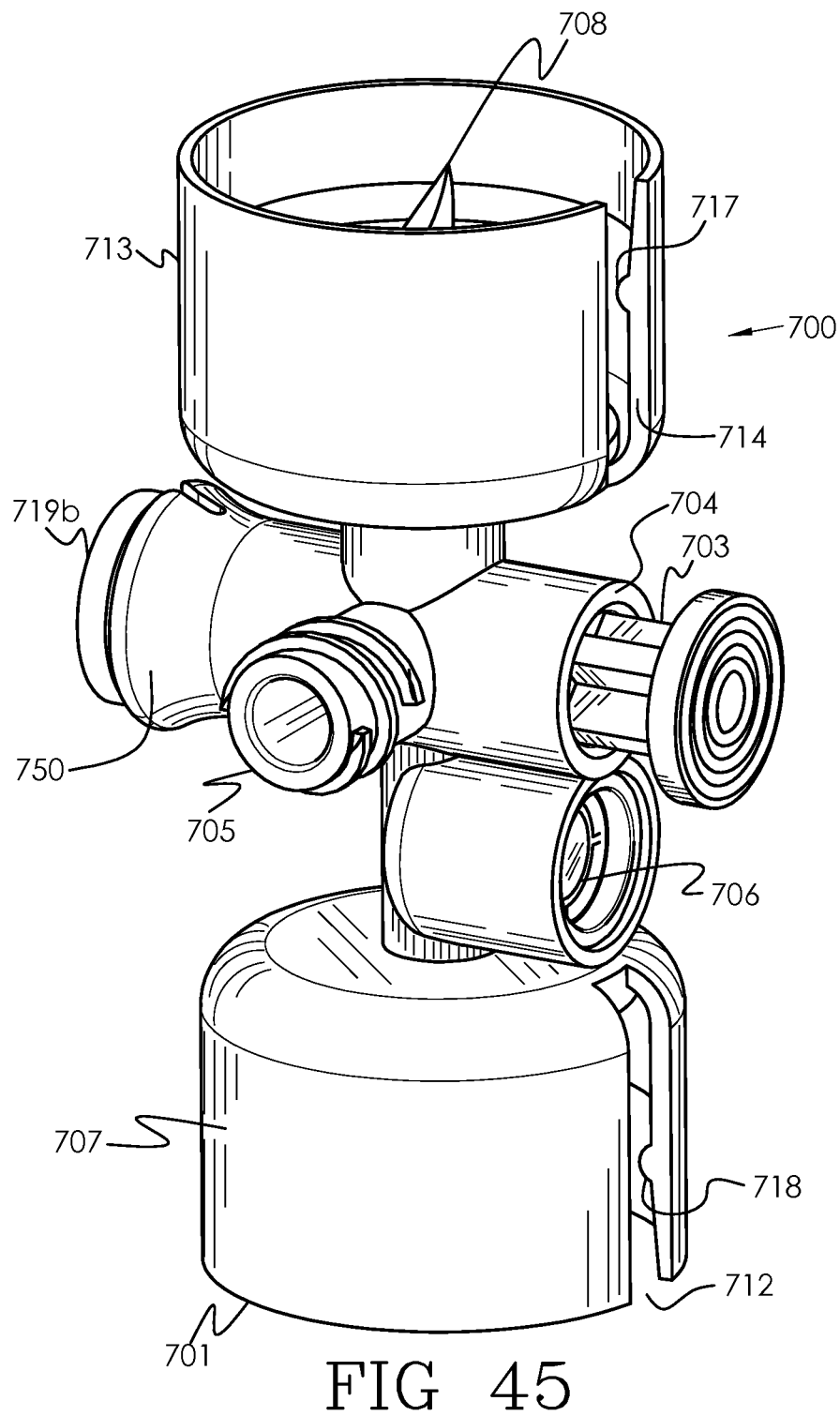
FIG. 45 is a perspective view of a fluid transfer device aspect as disclosed and described.

FIG. 45 is a perspective view of fluid transfer device (700) with fluid control similar to device 600, with the difference being the user-actuated plunger (703) may be bi-directionally slidably transversed to allow return to the first predetermined position. Likewise, device (700) comprises piercing assemblies (701, 702) for accessing a fluid container and for accessing a media container, and user-actuated plunger (703) positioned in housing opening (704). Connector (705) fluidly connects fluid delivery device, such as a syringe or fluid-containing IV bag. Vent (706) with optional filter is disposed between the first and second ends of the device housing (750). Piercing assemblies (701, 702) may each comprises a skirt (707, 713) for attaching to a vial or IV bag connecting port, each skirt includes slit (712, 714), the skirt being of a predetermined perimeter and of a predetermined length projecting distally away from the housing with the opening extending substantially the length of the skirt. Skirts (707, 713) include annular rings (718, 717) of any cross-sectional geometry about its interior for securing the container. User-actuated plunger (703) includes the addition of a second actuation means at the plunger second end (719b) in housing (750).

Figure 46:
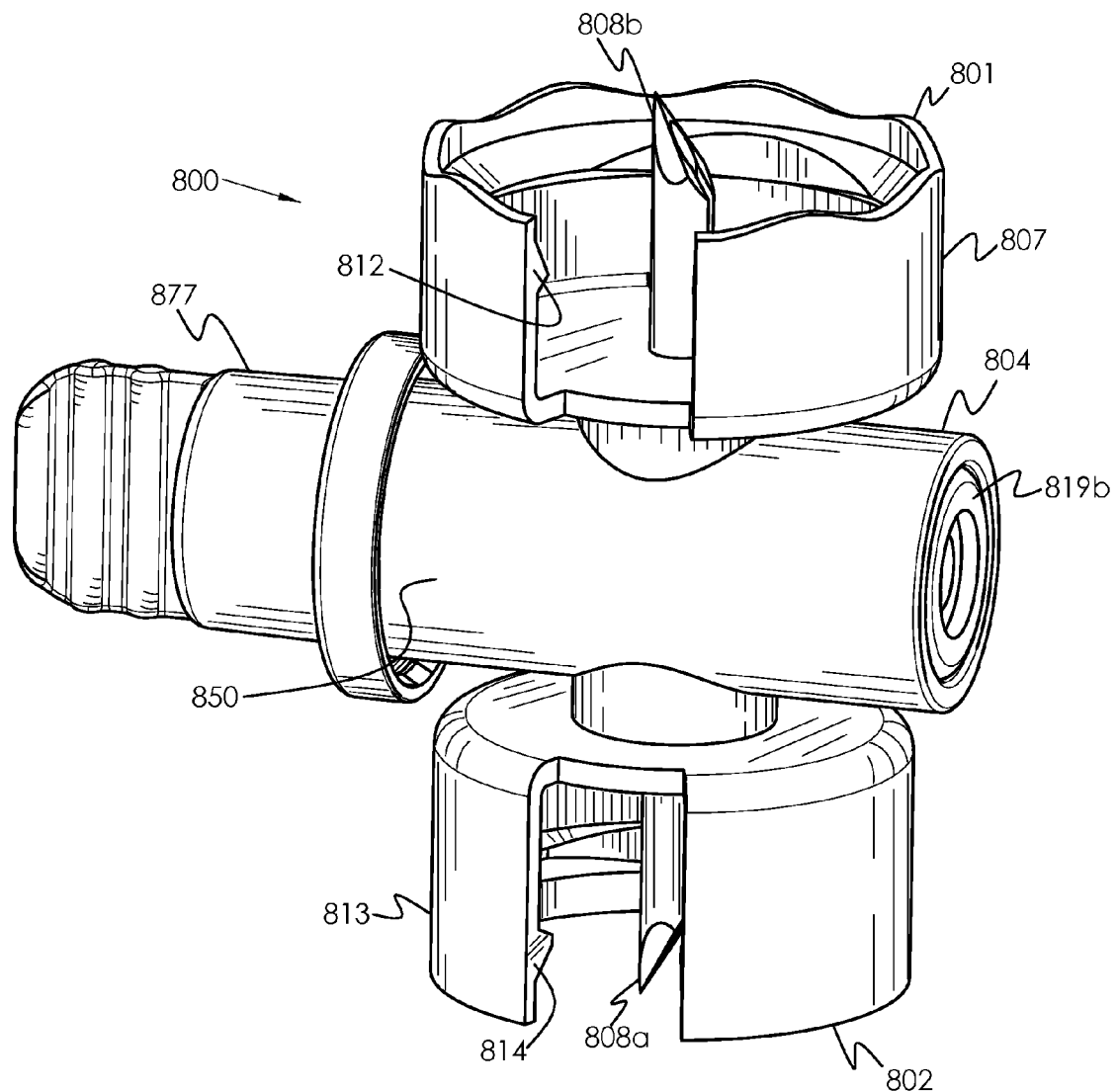
FIG. 46 is a perspective view of a fluid transfer device aspect as disclosed and described.

FIG. 46 is a perspective view of fluid control device (800) configured, for example, IV bag-to-container connection, or for any deformable (squeezable) fluid container to a second container. Device 800 includes housing (850) having first piercing assembly (801) and second piercing assembly (802), each piercing assembly comprising a corresponding piercing member (808b, 808a), respectively and skirt (807, 813) with attachment means (812, 814). Cap (877) locks and/or restricts movement of the user-actuated plunger prior to use.

Figure 47A:
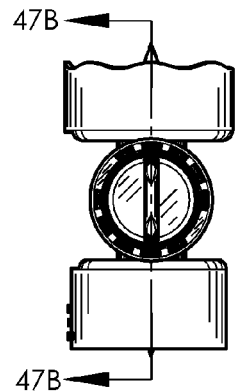
FIGS. 47A & 47B depict a sectional plane and corresponding cross-sectional view, respectively, of the device of FIG. 46.
Figure 47B:
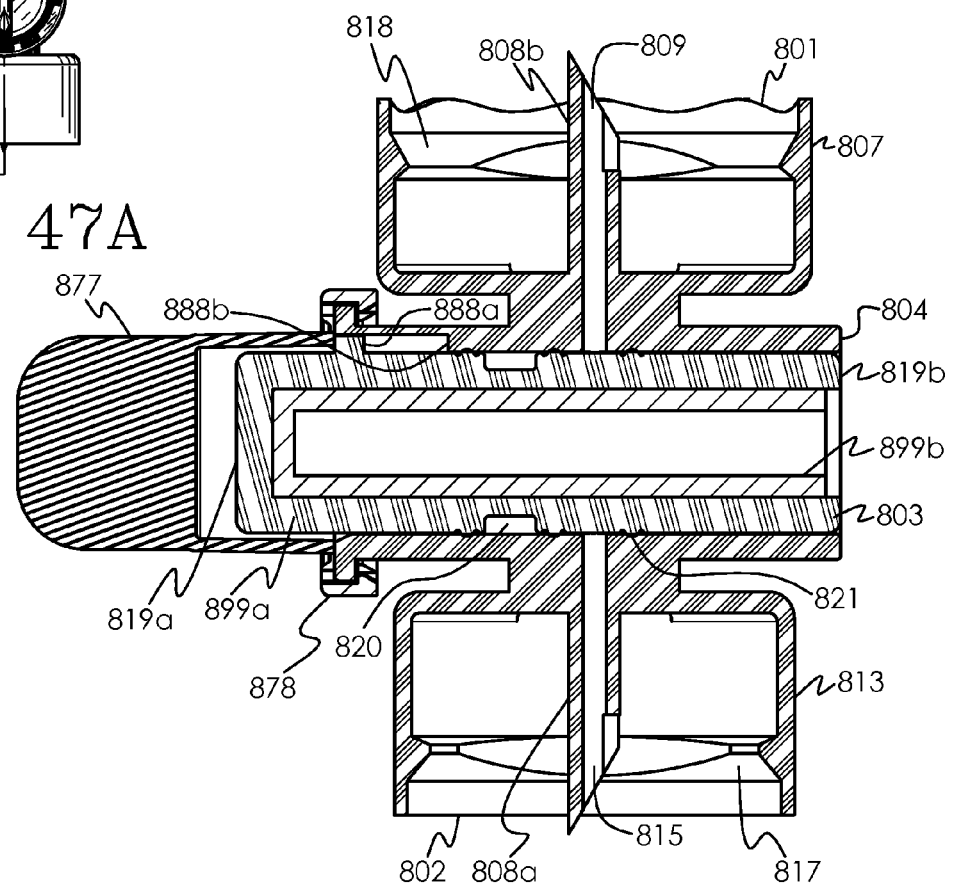

FIGS. 47A & 47B depict a sectional plane and corresponding cross-sectional view, respectively, of the device of FIG. 46. User-actuated plunger (803) is shown in a first predetermined position preventing fluid communication from first conduit (809) and second conduit (815) by isolating seals (821). User-actuated plunger (803) comprises a rigid core (899*b*) at partially surrounded by an elastomeric material (899*a*). Skirts (807, 813) include annular rings (818, 817) of any cross-sectional geometry about its interior for securing the container. User-actuated plunger (803) includes the addition of a second actuation means at the plunger second end (819*b*) in housing (850). Piercing assemblies (801, 802) terminate with piercing members (808*b*, 808*a*) for accessing the fluid container and for accessing a media container. User-actuated plunger (803) includes stop (888*a*) corresponding with housing stop (888*b*) for restricting rotational motion, and optionally, in combination with retainer (878) optionally integral with cap (877) restricting lateral motion.

Figures 48A, 48B:
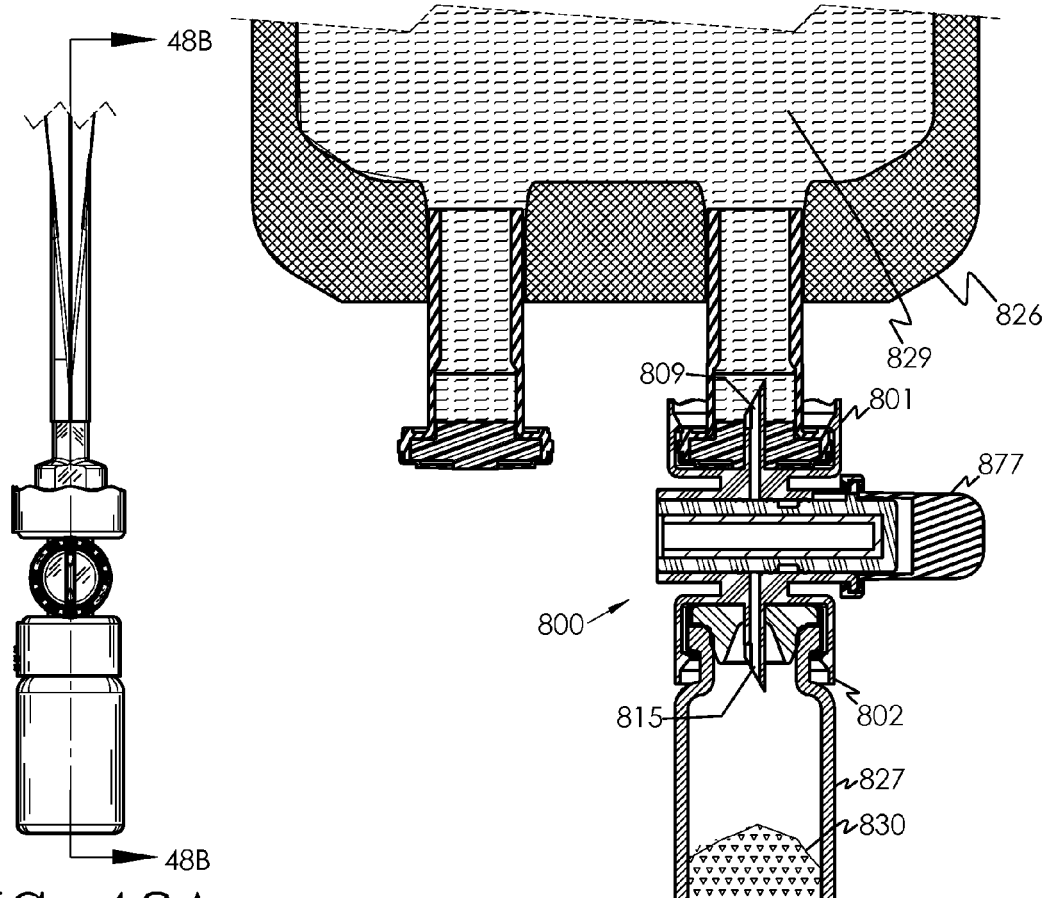
FIGS. 48A & 48B depict a sectional plane and corresponding cross-sectional view, respectively, of the device of FIG. 46 in an initial use state

FIGS. 48A & 48B depict a sectional plane and corresponding cross-sectional view, respectively, of device (800) in an initial state with the user-actuated plunger (803) in the first position restricting fluid communication. In the first predetermined position, device first piercing assembly (801) is secured to first container (826), such as an IV bag or other squeezable container containing a fluid media (829), and second piercing assembly (802) is secured to second media container (827) containing a second media (830), such as a solid. In this configuration, user-actuated plunger is positioned such that fluid communication is restricted between the first container and the second container.

Figures 49A, 49B:
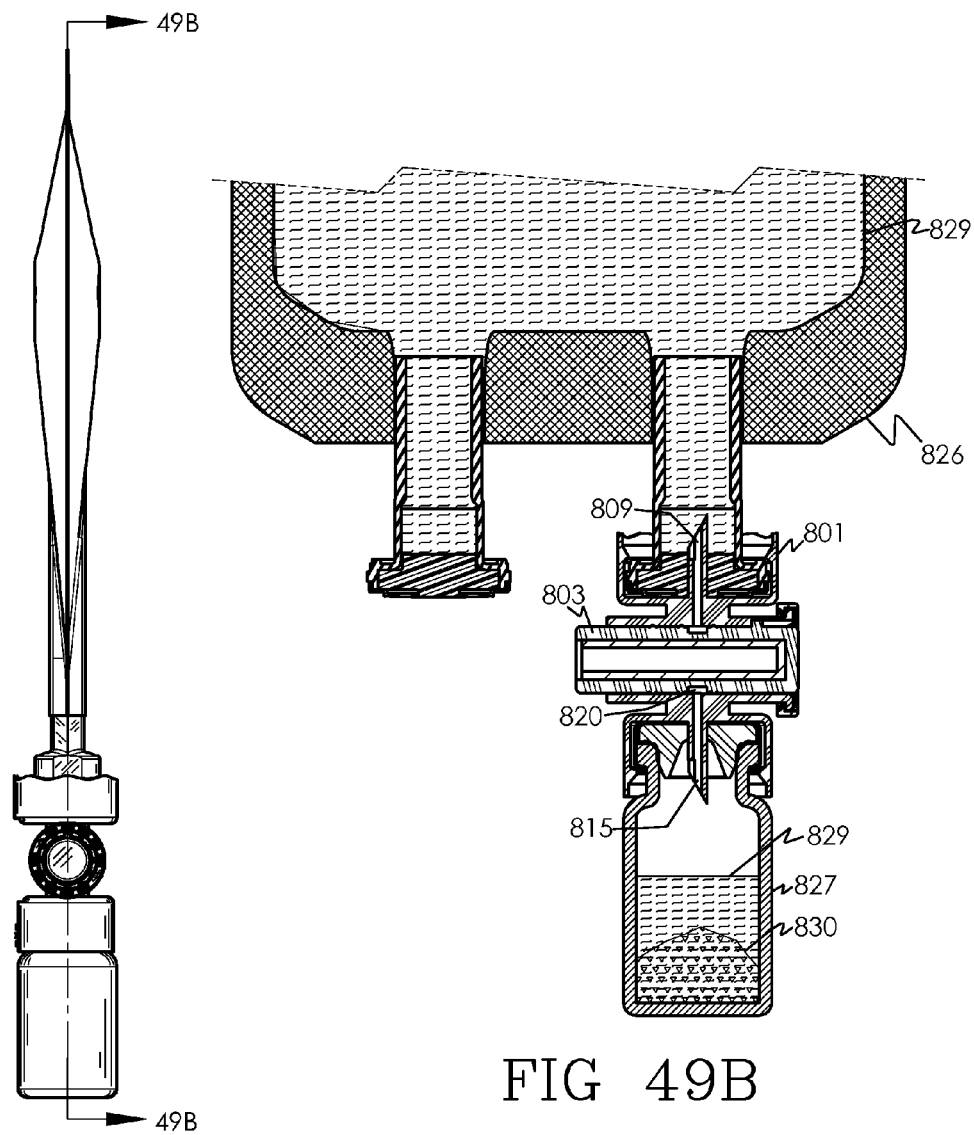
FIGS. 49A & 49B depict a sectional plane and corresponding cross-sectional view, respectively, of the device of FIG. 46 in an intermediate use state.

FIGS. 49A & 49B depict a sectional plane and corresponding cross-sectional view, respectively, of device of (800) in an intermediate use position with the user-actuated plunger with cap (877) removed and the plunger moved to the second predetermined position with fluid transferred from the fluid container (826) to the second container (827). Fluid transfer may be accomplished by squeezing the fluid container. In this configuration, flow channel (820) is aligned with fluid conduits (809, 815) permitting two-way flow.

Figures 50A, 50B:
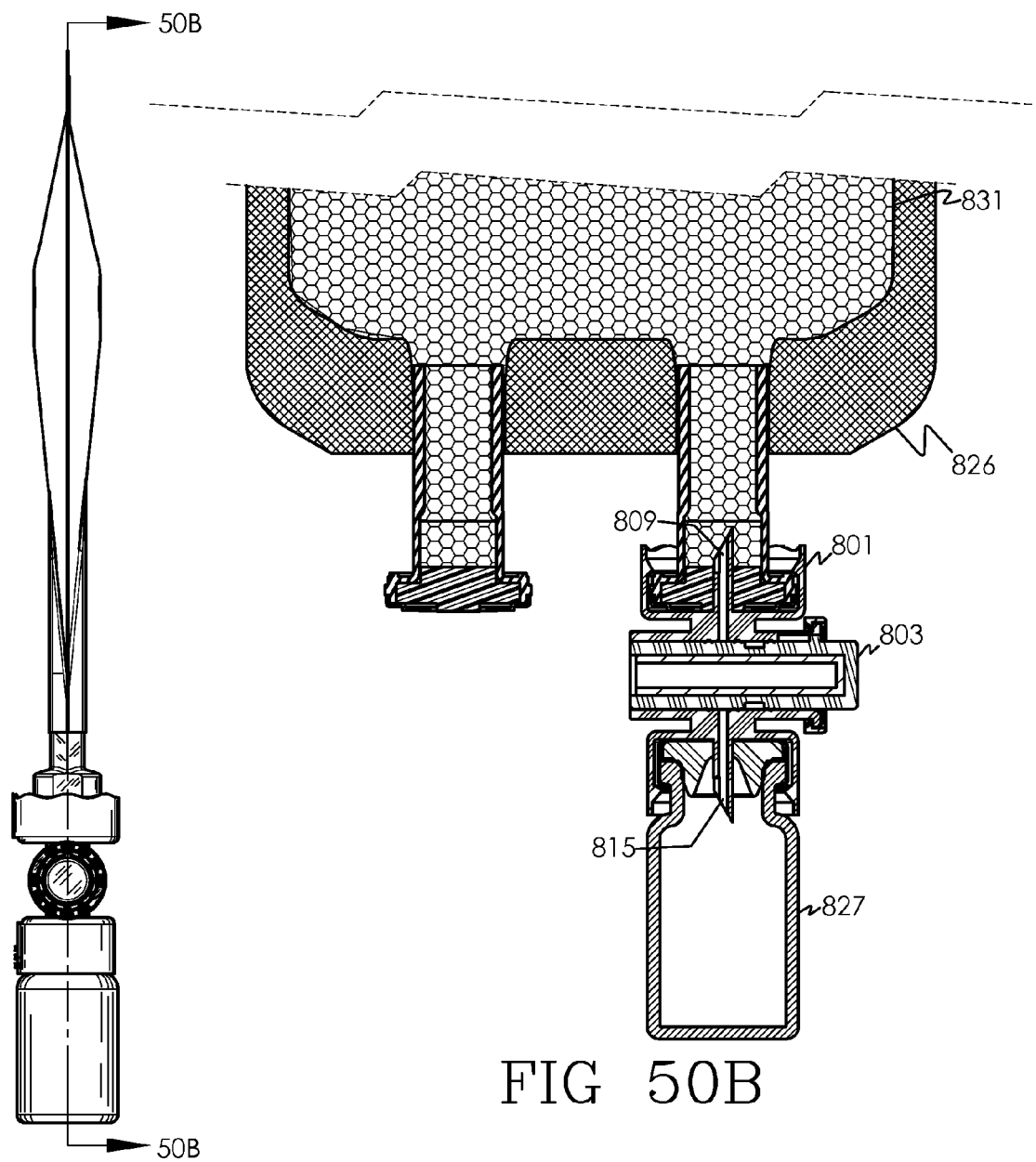
FIGS. 50A & 50B depict a sectional plane and corresponding cross-sectional view, respectively, of the device of FIG. 46 in a final use state.

FIGS. 50A & 50B depict a sectional plane and corresponding cross-sectional view, respectively, of device (800) in a final use position, where the mixture (831) is contained in fluid container (826) and user-actuated plunger (803) is in the first predetermined position. In this configuration, fluid is prevented from re-entering the second container (827).

Figure 51:
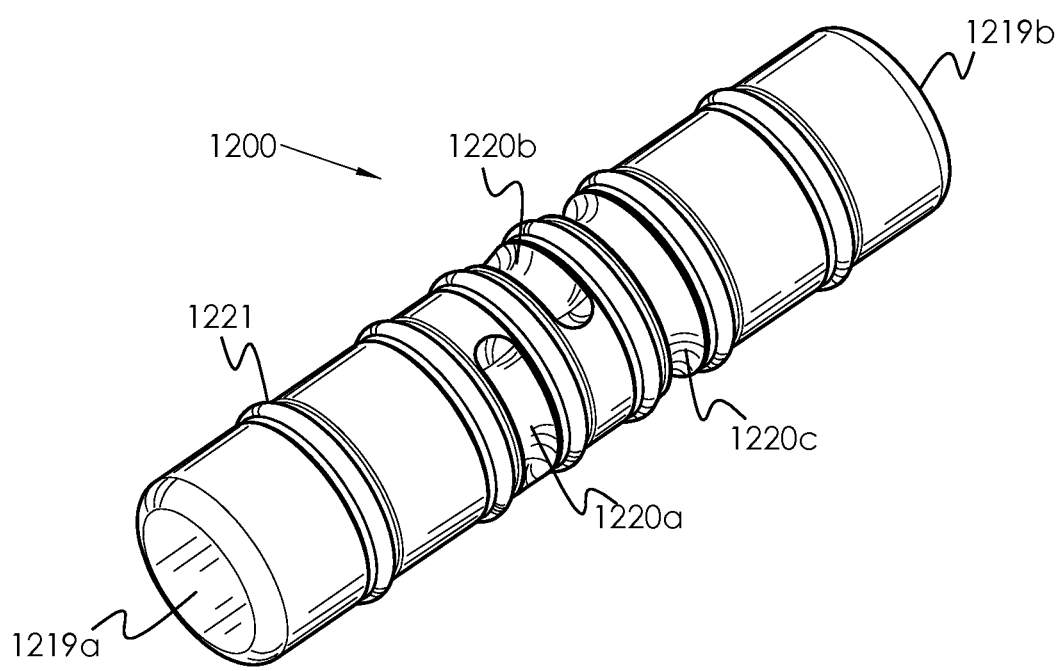
FIG. 51 is a perspective view of a user-actuated aspect as disclosed and described.

FIG. 51 is a perspective view of a user-actuated plunger (1200) which may be used in previously disclosed and described devices (600) and (700), for example, in combination with a cap covering the connector, to provide the function as described for device (800). Plunger (1200) includes flow channels (1220*a*, 1220*b*), which are positions partially about the perimeter of the plunger and positioned between plunger end (1219*a*, 1219*b*). Flow channels (1220*a*, 1220*b*) are arranged for fluid communication between either of the first or the second containers with the connector in the first or second predetermined position. Flow channel (1220*c*), is more proximal to end (1219*b*), and allows for fluid communication between the containers in the predetermined third position. Plunger (1200) includes annular seals (1221) that isolate the flow channel.

The user-actuated plunger of the fluid control devices disclosed and described herein may be of rigid construction or may be of a combination construction of rigid material and an elastomer. In particular, the user-actuated plunger is made, at least in part, of plastic with an elastomer over-molded or assembled thereon. In this respect, a fluid-tight sealing of the user-actuated plunger in relation to the housing is provided, particularly in any areas leading out from the housing. The user-actuated plunger can be optimally sealed off at one end of the housing or it may be free to extend from oppositely opposed openings of the housing. This configuration may permit a simple assembly of the plunger in the housing. The user-actuated plunger may be restricted from rotating in the housing. Any means for restricting the rotation of the user-actuated plunger may be employed. Specific examples of means for restricting or preventing rotation of the plunger may be internal, such as a keyway arrangement, or may be a sliding track-and-grove externally positioned on the housing and coupled to the plunger, for example.

In the previously described Figures and descriptions, gripping means may be provided on the outer surfaces of the fluid transfer device on any of a number of surfaces to provide effects including, but not limited to, embossed or debossed features, surface finish and over-mold/2-shot features and to improve user-tactile response and control.

In the previously described Figures and descriptions, the connector may be designed to mate with standard and non-standard, off-the-shelf, and custom syringes. This can potentially be a cost reduction measure because tooling will not be required for one or more of these components. The final device may also be affixed or pre-attached to a fluid delivery device, either permanently or reversibly.

In the previously described Figures and descriptions, the device may comprise multiple piercing members each with multiple conduits to be contained therein. Any of the piercing members may be integrated with their respective components or they may be pre-assembled. Any of the device components may be of a different material including, but not limited to, plastic, metal, and composites.

In the previously described Figures and descriptions, the device may be devoid of skirts or alternately, the device be equipped with other attachment means in place of the described skirt for securing to various containers such as but not limited to diluent bags, IV bags, and custom vials.

The previously described devices allow a user to draw in a measurable dose using an external fluid delivery device, such as a syringe so that all media from the first container is not drawn into the second container, particularly when the second container is under vacuum. The user-actuated plunger also may allow independent access to either container. Moreover, the previously described devices may allow the user to more easily manipulate the device using one-handed motions. This is an improvement over traditional stopcock-like fluid controls that require rotation, typically requiring both hands, and are structurally in contrast to the fluid control devices herein, which are essentially a linear device that allows the user to employ a squeeze-like motion allowing a more natural one handed movement.

In the previously described Figures and descriptions, the device comprises at least one vent which may increase the ease of use by relieving pressure that may build up in the media containers when adding or removing media, especially when precise metering of the fluid is desired. Thus, the incorporation of at least one vent eliminates the need to maintain pressure with the fluid delivery device.

The devices and methods of utilizing the devices as disclosed and described herein greatly reduce the number of steps typically associated with the access, preparation, and the dispensing/administration of drugs. Additionally, the devices disclosed and described herein, optimize the preparation and delivery of a drug or other solute, reducing waste by the design of the piercing member conduit dimensions and locations, reducing high-shear mechanical breakdown of the sensitive chemical or biochemical products by providing high flow fluid paths, reducing the time and complexity by eliminating steps, and/or by housing a needle within the assembly.

All of the devices and their components can be wholly or partially injection molded or molded by other methods known in the art. Design intent may be such that designs are molded with simple open/close tooling to reduce tool cost and cycle times.

Where feature definition may not be able to be achieved by single tool molding one or more of the components of the fluid transfer device may be mated or otherwise coupled together using methods known in the art, such as ultrasonic welding, adhesives or by mechanical retention means to join components. Adhesives may be employed to join components, particularly attachments that may be coupled with luer connections, where applicable. Adhesives may be, but are not limited to, cyanoacrylate, 2-part epoxy, heat-activated resin, UV cured adhesive and hot melts. Joining may also be achieved through, but not limited to, the use of a solvent bonding, ultrasonics and heat-staking means. Furthermore, where dissimilar materials may be advantageous used, a 2-shot molding technique may be utilized.

The needle safety mechanisms disclosed herein are inclusive of passively deployed or actively deployed mechanisms. The safety mechanism may be joined or otherwise integrated with the fluid delivery device.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid transfer device comprising:
    a housing comprising an elongated passage having at least one open end, the elongated passage having a longitudinal axis;
    a first piercing assembly associated with the housing projecting normal to the longitudinal axis of the elongated passage, the first piercing assembly adapted for accessing a first container, the first piercing assembly comprising a first piercing member having at least one conduit in fluidic communication with the elongated passage;
    a second piercing assembly associated with the housing projecting normal to the longitudinal axis of the elongated passage, the second piercing assembly adapted for accessing a second container, the second piercing assembly comprising a second piercing member having at least one conduit in fluidic communication with the elongated passage;
    a connector coupled to the housing, the connector adapted to receive a fluid delivery device and in fluidic communication with the elongated passage; and
    a user-actuated plunger at least partially slidably disposed in the elongated passage of the housing, linearly translatable along the longitudinal axis thereof independent of a fluid delivery device connected to the connector, the user-actuated plunger comprising:
    a first flow channel and
    a second flow channel, the second flow channel being distally separated from the first flow channel,
    wherein the user-actuated plunger is configured to slidably move without rotation during use within the passage between
    (i) a first predetermined position wherein the first flow channel provides fluid communication directly between the connector and the at least one conduit of the first piercing member, and
    (ii) a second predetermined position, wherein the second flow channel provides fluid communication directly between the connector and the at least one conduit of the second piercing member.

2. The fluid transfer device of claim 1, wherein the elongated passage is cylindrical.

3. The fluid transfer device of claim 2, wherein the user-actuated plunger provides metering of a predetermined amount of material from the first container to the connector.

4. The fluid transfer device of claim 1, wherein the user-actuated plunger includes a third flow channel, and the user-actuated plunger is further configured to move to a predetermined third position, where the third fluid channel provides fluid communication between the second container and the first container.

5. The fluid transfer device of claim 4, wherein the user-actuated plunger is prevented from moving to the predetermined third position prior to use.

6. The fluid transfer device of claim 1, wherein the at least one conduit of the first piercing member and the at least one conduit of the second piercing member are arranged so that media from the first container is not drawn into the second container whether or not the second container is under vacuum.

7. The fluid transfer device of claim 1, wherein the at least one conduit of the first piercing member or the at least one conduit of the second piercing member is selected from the group consisting of: a flow conduit, a vent conduit, a flow conduit and a vent conduit, and any of the at least one conduits in combination with a check valve or filter.

8. The fluid transfer device of claim 1, wherein the first flow channel and/or the second flow channel is positioned about the perimeter of the user-actuated plunger.

9. The fluid transfer device of claim 1, wherein the user-actuated plunger allows independent access to either container.

10. The fluid transfer device of claim 1, wherein the at least one additional conduit of the first piercing assembly and/or the second piercing assembly is a vent conduit.

11. The fluid transfer device of claim 1, wherein the housing further comprises at least one skirt of a predetermined perimeter and of a predetermined length projecting distally away from the housing and at least partially surrounding at least one of (i) the first piercing member of the first piercing assembly or (ii) the second piercing member of the second piercing assembly with a single opening extending substantially the length of the skirt.

12. A fluid transfer device comprising:
    a housing comprising an elongated passage having opposing open ends, the opening having a longitudinal axis separating the opposing open ends;
    a first piercing assembly associated with the housing projecting normal to the longitudinal axis of the elongate opening, the first piercing assembly adapted for accessing a first container, the first piercing assembly comprising a first piercing member having at least one conduit;
    a second piercing assembly associated with the housing projecting normal to the longitudinal axis of the elongated passage, the second piercing assembly adapted for accessing a second container, the second piercing assembly comprising a second piercing member having at least one conduit;
    a connector coupled to the housing, the connector adapted to receive a fluid delivery device; and
    a user-actuated plunger at least partially slidably disposed in the elongated passage of the housing, linearly translatable along the longitudinal axis thereof independent of a fluid delivery device connected to the connector, the user-actuated plunger comprising:

a first flow channel and a second flow channel, the second flow channel being distally separated from the first flow channel, wherein the user-actuated plunger is configured to slidably move without rotation during use within the passage between:

(i) a first predetermined position wherein the first flow channel provides fluid communication directly between the connector and the at least one conduit of the first piercing member, and (ii) a second predetermined position, wherein the second flow channel provides fluid communication directly between the connector and the at least one conduit of the second piercing member; and at least one skirt of a predetermined perimeter and of a predetermined length projecting distally away from the housing and at least partially surrounding at least one of (i) the first piercing member of the first piercing assembly or (ii) the second piercing member of the second piercing assembly with a single opening extending substantially the length of the skirt.

* * * * *